United States Patent
Yang et al.

(10) Patent No.: US 6,660,367 B1
(45) Date of Patent: Dec. 9, 2003

(54) SURFACE COATING FOR MICROFLUIDIC DEVICES THAT INCORPORATE A BIOPOLYMER RESISTANT MOIETY

(75) Inventors: Hua Yang, Foster City, CA (US); Steven A. Sundberg, San Francisco, CA (US)

(73) Assignee: Caliper Technologies Corp., Mountain View, CA (US)

( * ) Notice: Subject to any disclaimer, the term of this patent is extended or adjusted under 35 U.S.C. 154(b) by 18 days.

(21) Appl. No.: 10/279,670

(22) Filed: Oct. 24, 2002

Related U.S. Application Data

(63) Continuation of application No. 09/963,925, filed on Sep. 25, 2001, now Pat. No. 6,509,059, which is a continuation of application No. 09/264,519, filed on Mar. 8, 1999, now Pat. No. 6,326,083.

(51) Int. Cl.[7] .................................. B32B 3/22

(52) U.S. Cl. .................. 428/188; 428/166; 428/178; 428/195; 428/333; 428/429; 428/447

(58) Field of Search ................ 428/166, 178, 428/188, 195, 429, 333, 447

(56) References Cited

U.S. PATENT DOCUMENTS

| | | |
|---|---|---|
| 5,699,157 A | 12/1997 | Parce |
| 5,779,868 A | 7/1998 | Parce et al. |
| 5,800,690 A | 9/1998 | Chow et al. |
| 5,842,787 A | 12/1998 | Kopf-Sill et al. |
| 5,852,495 A | 12/1998 | Parce |
| 5,869,004 A | 2/1999 | Parce et al. |
| 5,876,675 A | 3/1999 | Kennedy |
| 5,880,071 A | 3/1999 | Parce et al. |
| 5,882,465 A | 3/1999 | McReynolds |
| 5,885,470 A | 3/1999 | Parce et al. |

FOREIGN PATENT DOCUMENTS

| | | |
|---|---|---|
| WO | WO-9800231 | 1/1998 |
| WO | WO-9800705 | 1/1998 |
| WO | WO-9800707 | 1/1998 |
| WO | WO-9802728 | 1/1998 |
| WO | WO-9805424 | 2/1998 |
| WO | WO-9822811 | 5/1998 |
| WO | WO-9845481 | 10/1998 |
| WO | WO-9845929 | 10/1998 |
| WO | WO-9846438 | 10/1998 |
| WO | WO-9849548 | 11/1998 |
| WO | WO-9855852 | 12/1998 |
| WO | WO-9856956 | 12/1998 |
| WO | WO-9900649 | 1/1999 |
| WO | WO-9910735 | 3/1999 |
| WO | WO-9912016 | 3/1999 |
| WO | WO-9916162 | 4/1999 |
| WO | WO-9919056 | 4/1999 |
| WO | WO-9919516 | 4/1999 |
| WO | WO-9929497 | 6/1999 |

OTHER PUBLICATIONS

Bruin et al. *J. Chromatog.* (1989) 471:429–436.
Emoto et al. *ACS Symp. Ser.*, 680(*Poly(ethylene glycol*) (1997) 374–399.
Emoto et al. *Langmuir* (1998) 14:2722–2729.
Erim et al. *J. Chromatog.* (1995) 708:356–361.
Gilges et al. *Anal. Chem.* (1991) 2038–2046.
Gordon et al. *Anal. Chem.* (1991) 63:69.
Herren et al. *J. Colloid. Interface Sci* (1987) 115:46.
Huang et al. *J. Microcol. Sep.* (1992) 4:135–143.
Ikl et al. *J. Chromag.* (1996) A731:273–282.
Katayarna et al. *Anal. Chem.* (1998) 70:2254–2260.
Mechref et al. *Electrophoresis* (1995) 16:617–624.
Nashabeh et al. *J. hish Resol. Chromatog* (1992) 15:289.
Palm et al. *Anal. Chem.* (1997) 69:4499–4507.
Strege et al. *Anal. Biochem.* (1993) 210:402–410.
Towns et al. *J. Chromatog* (1992) 599:227–237.

*Primary Examiner*—D. S. Nakarani
(74) *Attorney, Agent, or Firm*—Donald R. McKenna

(57) ABSTRACT

Hydrophilic protein adsorption resistant coatings for microfluidic devices are provided. Additionally, microfluidic devices and methods of manufacturing microfluidic devices that include the coatings are provided.

9 Claims, 32 Drawing Sheets

BSA-BODIPY-FL
PI<7.5, net - Charge

BSA-BODIPY-FL
PI<7.5, net - Charge

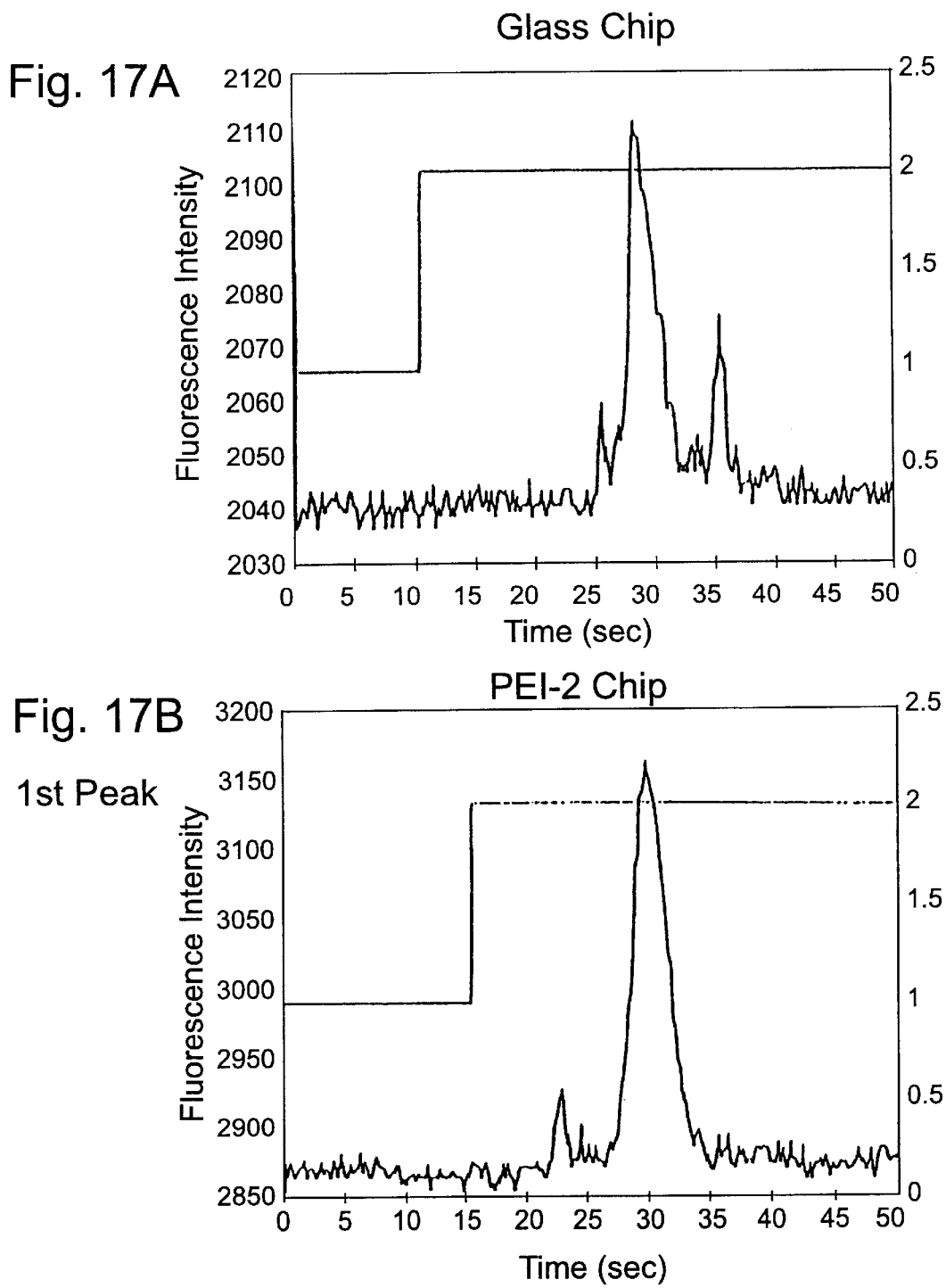
Fig. 17A Glass Chip
Fig. 17B PEI-2 Chip
1st Peak

6th Peak

Avidin-BODIPY-FL
PI>7.5, net (+) Charge

SURFACE COATING FOR MICROFLUIDIC DEVICES THAT INCORPORATE A BIOPOLYMER RESISTANT MOIETY

CROSS-REFERENCE TO RELATED APPLICATIONS

This application is a continuation of U.S. patent application Ser. No. 09/963,925, filed Sep. 25, 2001, now U.S. Pat. No. 6,509,059, which is a continuation of U.S. patent application Ser. No. 09/264,519, filed Mar. 8, 1999, now U.S. Pat. No. 6,326,083.

FIELD OF THE INVENTION

This invention relates to microfluidic devices, including biopolymer adsorption resistant coatings for microfluidic devices.

BACKGROUND OF THE INVENTION

Active capillary and channel surfaces in separation devices can create problems in virtually any separation methodology, including chromatographic, electrophoretic and electroosmotic modalities. The charged surfaces of the capillaries and channels of these separation devices are particularly problematic in the separation of charged analytes such as proteins, peptides and nucleic acids. Charged biopolymer compounds are adsorbed onto the walls of the separation device, creating artifacts such as peak tailing, loss of separation efficiency, poor analyte recovery and poor retention time reproducibility. The interaction of biopolymers with the surfaces of the device seems to be the main reason for the loss in separation efficiency compared to that predicted by theory. The adsorption is believed to be due to the electrostatic interactions between positively charged residues on the biopolymer and negatively charged groups resident on the surface of the separation device.

Silica-based capillaries utilized in capillary electrophoresis have been modified with a range of coatings intended to prevent the adsorption of charged analytes to the walls of the capillaries. Surface deactivation methods include surface derivatization with poly(ethyleneglycol) or poly (ethyleneimine). See, for example Huang et al., *J. Microcol.* Sep. 4, 135–143 (1992); and Bruin et al., *Journal of Chromatogr.*, 471, 429–436 (1989).

Poly(ethyleneglycol)-like epoxy polymers that are functionalized with pendent hydroxy groups have also been formed on the surface of a silica-based capillary. This surface was shown to impart resistance towards protein adsorption to the capillary surface. See, Towns et al., *Journal of Chromatogr.*, 599, 227–237 (1992).

Capillary surfaces have also been functionalized with poly(ethyleneimine) by etching the surface of the silica capillary with a sodium hydroxide solution followed by treating the etched surface with a poly(ethyleneimine) solution. Under acidic conditions, the polyimine coatings bear a positive charge which makes them particularly suited for the separation of basic proteins, since, at acidic pH, both the capillary surface and the proteins bear a positive charge. See, Erim, et al., *Journal of Chromatogr.*, 708, 356–361 (1995) and references therein.

Other chemical modifications of the capillary have also been employed, such as polyacrylamide (Hjerten, *J. Chromatogr.*, 347, 191 (1985)), glycol groups (Jorgenson, *Trends Anal. Chem.* 3, 51 (1984)), polysiloxanes and a glyceroglycidoxypropyl coating (McCormick, *Anal. Chem.*, 60, 2322 (1998)).

For reproducible analyses and purifications, it is desirable that the coating on an electrophoretic or electroosmotic device remain substantially stable during the useful lifetime of the device. Additionally, to prevent the adsorption of charged analytes onto the surfaces of the device, hydrophilic polymers such as poly(ethyleneglycol) and hydroxyethylated poly(ethyleneimine) are particularly useful. Furthermore, for electroosmotic devices, it is desirable to have a coating bearing a charge that can be adjusted in magnitude by manipulating the conditions inside of the device (e.g., pH). An array of coatings which allowed the direction of electroosmotic flow to be chosen based on the choice of coating would also be of use. Surprisingly, the present invention provides coatings, methods and devices which possess these and other characteristics that will be apparent upon complete review of this disclosure.

SUMMARY OF THE INVENTION

It has now been discovered that the properties of microfluidic devices can be substantially modified by coating the microchannels or chambers with a charged, hydrophilic group. Thus, the present invention provides surface coatings for microfluidic devices that effectively suppress biopolymer adsorption and provide reproducibility in the preparation of microfluidic devices. Additionally, the coatings of the present invention provide stable and reproducible electroosmotic flow. As the present invention provides both positively and negatively charged coatings, the direction of the electroosmotic flow can be selected based on the choice of coating. In addition to the coatings, the invention provides methods for ascertaining the quality, extent and utility of the coating. The invention also provides devices utilizing the coatings.

In a first aspect, the present invention provides a biopolymer adsorption resistant surface having the formula:

$$R^1-\{(R^2)_a-(R^3)_m\}_n \qquad (I)$$

wherein, $R^1$ is a member selected from glass, organic polymers, and silica-based polymers; $R^2$ is selected from amino acids and peptides; $R^3$ is a hydrophilic polymer; a is equal to or greater than zero (0); m is at least 1; and n is equal to or greater than zero (0).

In addition to the desirable properties of the above described groups, it has also been discovered that hydroxyethylated poly(ethyleneimine)-based species produce a coating which, when compared to non-hydroxyethylated poly (ethyleneimine)-based coatings, is substantially more stable over time, provides better reproducibility between analyses and demonstrates dramatically reduced protein adsorption.

Thus, in a second aspect, the present invention provides a biopolymer adsorption resistant surface having the formula:

$$R^1-(R^2)_m \qquad (II)$$

wherein, $R^1$ is selected from glass, organic polymers, and silica-based polymers; $R^2$ is a hydroxyethoxylated polyethyleneimine; and m is at least 1.

In a third aspect, the present invention provides a method of manufacturing a biopolymer adsorption resistant microfluidic device having at least one microchannel therein. The method includes derivatizing the surface of the microchannel with a first surface modifying agent. The extent of the derivatizing is monitored by establishing an electroosmotic flow of a material within the channel and measuring a property of the flow to obtain a value. The measured property is compared to a reference value for the property. The variation between the value of the measured property and the reference property provides a measure of the extent of deriviatizing.

In a fourth aspect, the present invention provides a method of manufacturing a biopolymer adsorption resistant microfluidic device having at least one microchannel therein. The microchannel has a surface coating comprising n subunits. The method of manufacturing includes derivatizing the surface of the microchannel with a surface modifying agent, after which the extent of the derivatization is monitored as described above. In order to build up a coating of n subunits, the derivatizing and monitoring steps are repeated up to n−1 times.

Other objects, features and advantages of the present invention will become apparent from the detailed description that follows.

BRIEF DESCRIPTION OF THE FIGURES

FIG. 15 is a plot of fluorescence intensity vs. time for a mobility stability test of a microfluidic devise coated by PEI-2 (80% ethoxylated polyethylenimine)

FIGS. 17A–D are a comparison of protein adsorption on a glass microfluidic device and PEI-2 coated microfluidic device by the peak shape of the BSA-Bodipy-FL injecting test.

DETAILED DESCRIPTION OF THE INVENTION AND THE PREFERRED EMBODIMENTS

Definitions

Figure 1:
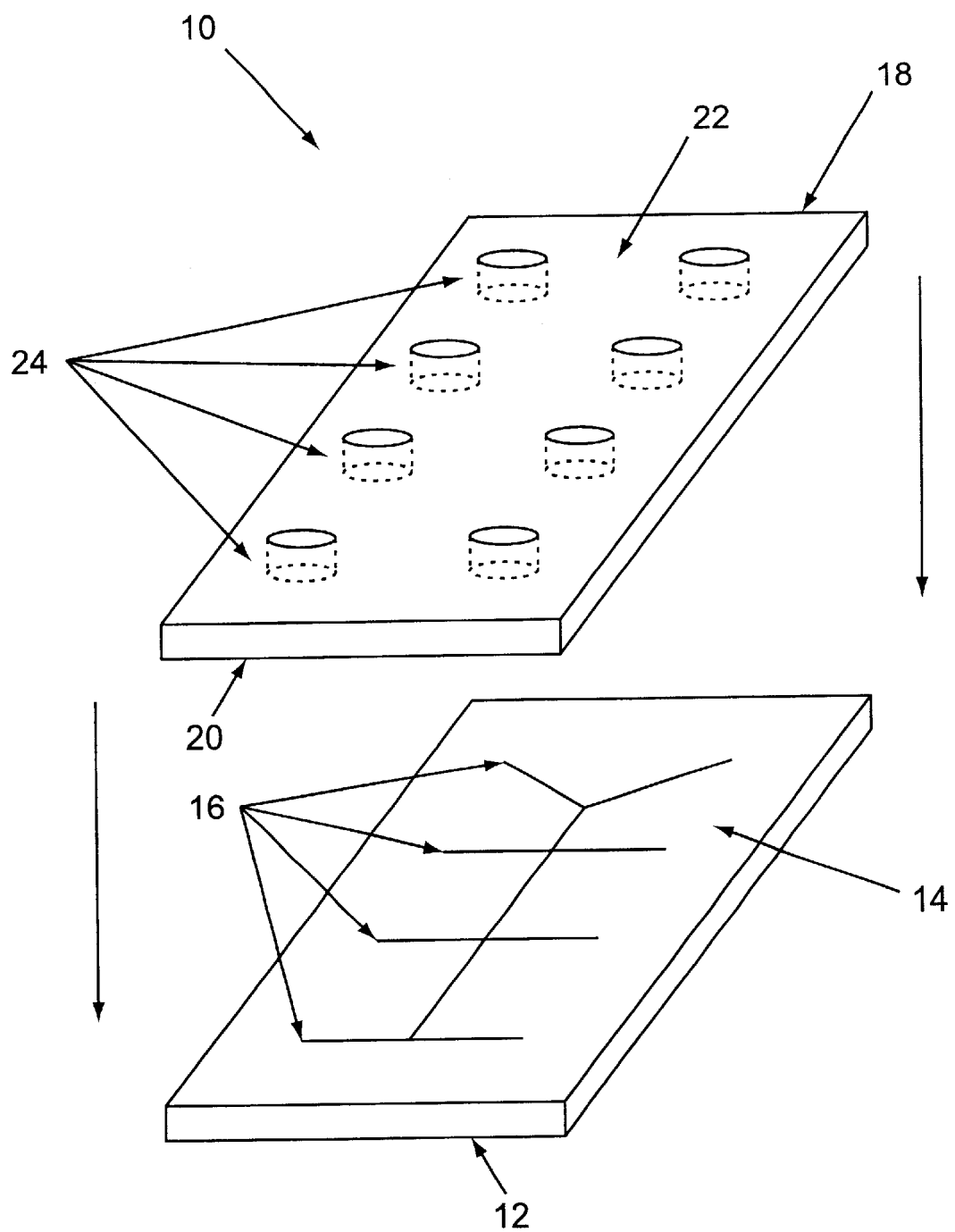
FIG. 1 is a cartoon illustrating a two layer body structure for a microfluidic device.

"Biopolymer," as used herein, refers to both oligomers and polymers of biomolecules such as amino acids, carbohydrates, nucleic acids and combinations thereof. The biopolymers can be isolated from natural sources, entirely synthetic or they can include molecules that are isolated from natural sources and are subsequently modified.

As used herein, the term "oligomer," refers to biomolecules as defined above having two to ten monomeric subunits. The subunits can be the same or different.

As used herein, the term "polymer," refers to biomolecules as defined above having more than ten monomeric subunits. The subunits can be the same or different.

The term "attached," as used herein encompasses interaction including, but not limited to, covalent bonding, ionic bonding, chemisorption, physisorption and combinations thereof.

The term "independently selected" is used herein to indicate that the groups so described can be identical or different The term "alkyl" is used herein to refer to a branched or unbranched, saturated or unsaturated, monovalent hydrocarbon radical having from 1–30 carbons and preferably, from 4–20 carbons and more preferably from 6–18 carbons. When the alkyl group has from 1–6 carbon atoms, it is referred to as a "lower alkyl." Suitable alkyl radicals include, for example, structures containing one or more methylene, methine and/or methyne groups. Branched structures have a branching motif similar to i-propyl, t-butyl, i-butyl, 2-ethylpropyl, etc. As used herein, the term encompasses "substituted alkyls."

"Substituted alkyl" refers to alkyl as just described including one or more functional groups such as lower alkyl, aryl, acyl, halogen (i.e., alkylhalos, e.g., CF$_3$), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon of the alkyl moiety. Additionally, these groups may be pendent from, or integral to, the alkyl chain.

"Chemisorption," as used herein refers to the formation of bonds between a surface and the coating molecules in contact with it. These bonds are comparable in strength to chemical bonds and are much stronger than the van der Waals interactions characterizing physical interaction.

"Physisorption," as used herein refers to a physical adsorption process in which there are van de Waals forces between the coating molecules and the substrate surface.

Abbreviations

EOF, electroosmotic flow; PTP1b, tyrosine phosphatase 1b; diFMUP, di-6-a-difluoro-4-methylumbelliferyl phosphate, PEI-1, poly(ethyleneimine); PEI-2, hydroxyethylated poly(ethyleneimine).

Introduction

The ability to control solute-surface interactions such as protein adsorption to capillary walls is extremely important for successful implementation of miniature, integrated biochemical processing systems such as the microfluidic devices contemplated in the present invention. Surface modification using hydrophilic polymer coatings is a popular approach to reducing protein adsorption onto surfaces that are important in the biotechnology industry. A variety of polymers, including poly(ethylene glycol) (PEG), poly(vinylalcohol) (PVA), polyacrylamide (PA), poly(vinylpyrrolidone) (PVP), polysaccharides such as poly (glucose), i.e., dextran, and, alkylated celluloses have been examined in this context. Because of its solubility, wettability, nontoxicity and biocompatibility. PEG-coatings have been studied and used extensively (*Poly(ethylene Glycol) Chemistry: Biotechnical and Biomedical Applications*, J. M Harris, Ed., Plenum, N.Y. (1992)). It has been demonstrated that PEG-coatings can greatly reduce protein, cell and bacterial adsorption to treated surfaces, therefore PEG-coatings is one of the best approaches to try for microfluidic device applications.

PEG molecules can localized at surfaces by modifying them with functional groups which encourage strong adsorption via hydrophobic or ionic interactions (Osterberg et al., *Colloids Surf.* A 77: 159–169 (1993); Gilges et al., *Anal. Chem.* 66: 2038–2046 (1994); Iki et al., *J. Chromatogr.* A 731: 273–282 (1996); Gordon et al., *Anal. Chem.* 63: 69 (1991) Katayarna et al., *Anal. Chem.* 70: 2254–2260 (1998); Ansari et al., Book of Abstracts, 213th ACS National Meeting, San Francisco, Apr. 13–17 (1997); Strege et al., *Anal. Biochem.* 210: 402–410 (1993). They can also be covalently grafted by reacting the surfaces with functionalized PEGS. Although most surface modification procedures used in CE, GC, HPLC and affinity chromatography can be adapted and used for preparation of microfluidic devices, for economic and manufacturing reasons the procedures used for microfluidic device applications should be both easy and simple.

Although many suitable coating procedures are encompassed by the present invention, three such procedures are preferred: 1) adsorptive modification through Van der Waals force, hydrogen bonding or electrostatic interaction; 2) direct covalent modification through a silane bond; and 3) indirect covalent modification through a silane or polymer linker.

This invention provides biopolymer adsorption resistant surfaces for microfluidic devices. These surfaces are structurally simple and they exhibit excellent operational stability. Additionally, the conditions for producing the surfaces are easily reproduced from device to device. In addition to the coatings, the invention provides methods for ascertaining the quality, extent and utility of the coating. The invention also provides microfluidic devices utilizing the coatings.

The properties of microfluidic devices can be substantially modified by coating the microchannels or chambers with a charged, hydrophilic group. Thus, the present invention provides surface coatings for microfluidic devices that effectively suppress biopolymer adsorption and provide reproducibility in the preparation of microfluidic devices. Additionally, the coatings of the present invention provide stable and reproducible electroosmotic flow. As the present invention provides both positively and negatively charged coatings, the direction of the electroosmotic flow can be selected based on the choice of coating.

Poly(ethyleneglycol)-based Coatings

In a first aspect, the present invention provides a biopolymer adsorption resistant surface having the formula:

   (I)

wherein, R$^1$ is a substrate which member selected from organic polymers, glass and silica-based polymers; R$^2$ is a spacer group which includes an amino acid or peptide. Each R$^2$ group in a plurality of R$^2$ groups can include the same amino acid or peptide. Alternatively, the amino acid or peptide in the R$^2$ groups can differ over the plurality of R$^2$ groups. R$^3$ is a hydrophilic polymer; a is equal to or greater than zero (0); m is at least 1; and n is equal to or greater than zero (0).

In a preferred embodiment, the substrate R$^1$ is a member selected from the group consisting of silica, fused silica, glass, quartz, polycarbonate, polypropylene, polystyrene, acrylic polymers, polymethylmethacrylate and its copolymers, cellulose and combinations thereof.

Many methods for functionalizing these surfaces are known in the art. A wide variety of reaction types is available for the functionalization of a substrate surface. For example, substrates constructed of a plastic such as polypropylene, can be surface derivatized by chromic acid oxidation, and subsequently converted to hydroxylated or aminomethylated surfaces. Additionally, substrates made from highly crosslinked divinylbenzene can be surface derivatized by chloromethylation and subsequent functional group manipulation.

The substrates are constructed of a siliceous material, such as silicon oxides, silicon carbide, silicon nitride, silicates, silicon and glass. The preferred material is glass.

The substrate surface can be derivatized with a silicon-based coupling reagent by reacting the surface Si—OH, SiO—H, and/or Si—Si groups with a coupling reagent. The coupling reagent can be functionalized with a hydrophilic polymer prior to the reagent being bound to the substrate. Alternatively, the surface can be assembled in multiple steps. For example, a coupling reagent bearing a reactive group can be bound to the substrate. The reactive group can be in either its free or protected form. The reactive group is subsequently reacted with the hydrophilic polymer or an active derivative of the polymer.

In a preferred embodiment, wherein the substrates are made from glass, the covalent bonding of the reactive group to the glass surface is achieved by conversion of groups on the substrate's surface by a silicon modifying reagent such as:

$$(RO)_3SiR^1X \qquad (II)$$

where R is an alkyl group, such as methyl or ethyl. $R^1$ is a linking group between silicon and X. In preferred embodiments, the linking group is an alkyl or substituted alkyl group. X is a reactive group or a protected reactive group.

The reactive groups (X) can be one or more of a number of organic functional groups including, but not limited to:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups which can be converted to disulfides or reacted with acyl halides;

(h) amine or sulfhydryl groups which can be, for example, acylated or alkylated;

(i) alkenes which can undergo, for example, cycloadditions, acylation, Michael addition, etc; and (j) epoxides which can react with, for example, amines and hydroxyl compounds.

An array of silicon-based molecules appropriate for functionalizing surfaces are commercially available. See, for example, *Silicon Compounds Registry and Review*, United Chemical Technologies, Bristol, Pa. Additionally, the art in this area is well developed and those of skill will be able, without undue experimentation, to both choose an appropriate molecule for a given purpose. Appropriate molecules can be purchased commercially, synthesized de novo, or it can be formed by modifying an available molecule to produce one having the desired structure and/or characteristics.

By way of example, the reactive groups on a number of siloxane functionalizing reagents can be converted to other useful functional groups:

1. Hydroxyalkyl siloxanes (Silylate surface, functionalize with diborane, and $H_2O_2$ to oxidize the alcohol)
    a. allyl trichlorosilane→→3-hydroxypropyl
    b. 7-oct-1-enyl trichlorchlorosilane→→8-hydroxyoctyl
2. Diol (dihydroxyalkyl) siloxanes (silylate surface and hydrolyze to diol)
    a. (glycidyl trimethoxysilane→→(2,3-dihydroxypropyloxy)propyl
3. Aminoalkyl siloxanes (amines requiring no intermediate functionalizing step)
    a. 3-aminopropyl trimethoxysilane→aminopropyl
4. Dimeric secondary aminoalkyl siloxanes
    a. bis(3-trimethoxysilylpropyl)amine→→bis(silyloxylpropyl)amine.

See, for example, Leyden et al., *Symposium on Silylated Surfaces*, Gordon & Breach 1980; Arkles, *Chemtech* 7, 766 (1977); and Plueddemann, *Silane Coupling Reagents*, Plenum. N.Y., 1982.

These examples are intended to be illustrative and do not limit the types of reactive group interconversions which are useful in conjunction with the present invention. Additional starting materials and reaction schemes will be apparent to those of skill in the art.

The reactive groups can be chosen such that they do not participate in, or interfere with, the reaction controlling the attachment of the silicon-based component onto the substrate's surface. Alternatively, the reactive group can be protected from participating in the reaction by the presence of a protecting group. Those of skill in the art will understand how to protect a particular functional group from interfering with a chosen set of reaction conditions. For examples of useful protecting groups, See Greene et al., *Protective Groups in Organic Synthesis*, John Wiley & Sons, New York, 1991.

$R^2$ Groups

Surfaces in which $R^2$ is a group bearing a permanent charge or a pH dependent charge are useful in practicing the present invention. In preferred embodiments, the charged group is a carboxylate, quaternary amine or protonated amine that is a component of an amino acid that has a charged or potentially charged side chain. The amino acids can be either those having a structure which occurs naturally or they can be of unnatural structure (i.e., synthetic).

Useful naturally occurring amino acids include, arginine, lysine, aspartic acid and glutamic acid. Surfaces utilizing a combination of these amino acids are also of use in the present invention. Further, peptides comprising one or more residues having a charged or potentially charged side chain are useful coating components and they can be synthesized utilizing arginine, lysine, aspartic acid, glutamic acid and combinations thereof. Useful unnatural amino acids are commercially available or can be synthesized utilizing art-recognized methodologies.

In those embodiments in which an amino acid moiety having an acidic or basic side chain is used, these moieties can be attached to a surface bearing a reactive group through standard peptide synthesis methodologies or easily accessible variations thereof. See, for example, Jones, *Amino Acid and Peptide Synthesis*, Oxford University Press, Oxford, 1992.

In one representative example, an aminopropylsilylated surface is reacted with a protected aspartic acid derivative. The amino acid carboxy of aspartic acid will couple to the amine derivatized surface via an amide bond. Numerous carboxy activating strategies and reagents are available. These include, but are not limited to, the use of acyl chlorides, acyl azides, carbodiimides-hydroxybenzotriazole and the like.

The aspartic acid side chain carboxy group can be protected by its conversion to, for example, a benzyl ester or t-butyl ester. The aspartic acid amino group can also be protected to prevent its interfering with the coupling reaction. Appropriate amine protecting groups include, for example, FMOC, t-Boc, chloroformates and the like. It will be apparent to those of skill in the art that this methodology is equally applicable to other natural carboxy side chain amino acids (e.g., glutamic acid) and unnatural carboxy side chain amino acids.

Hydrophilic Groups

In preferred embodiments $R^3$ is a hydrophilic radical. Preferred hydrophilic radicals include oligomeric and polymeric ethers and alcohols. In further preferred embodiments, $R^3$ is a radical of which at least a portion is comprised of a member selected from the group consisting of poly (ethyleneglycol) and substituted poly(ethyleneglycol). Poly(ethyleneglycol) moieties within a wide range of molecular weights and sizes are useful in practicing the present invention. In a preferred embodiment, the poly (ethyleneglycol) portion has a formula weight ranging from about 45 daltons to about 20,000 daltons. In a further preferred embodiment, the poly(ethyleneglycol) portion has a formula weight ranging from about 200 to about 1,000 daltons.

The hydrophilic polymer can be attached to the amino acid residue by a number of methods known to those of skill in the art. In an exemplary embodiment, a commercially available poly(ethyleneglycol) functionalized with a carboxy group at one of the hydroxyl termini is coupled to the aspartic acid residue tethered to the surface via the α-amino group of the aspartic acid. Carboxy-to-amine coupling chemistries such as those discussed above are generally useful in this step of the synthesis. During the coupling of the hydrophilic polymer, the aspartic acid side chain carboxy will generally be protected to prevent its reaction with the α-amine groups of adjacent aspartic acid moieties. Following the coupling of the polymer to the surface, the aspartic acid side chain carboxy can be deprotected, affording a charged, hydrophilic coating.

A wide range of mono-, di- and bis-functionalized poly (ethyleneglycol) molecules are commercially available and will prove generally useful in this aspect of the invention. See, for example, 1997–1998 Catalog, Shearwater Polymers, Inc., Huntsville, Ala. Additionally, those of skill in the art have available a great number of easily practiced, useful modification strategies within their synthetic arsenal. See, for example, Harris, *Rev. Macromol. Chem. Phys.*, C25(3), 325–373 (1985); Zalipsky et al., *Eur. Polym. J.*, 19(12), 1177–1183 (1983), U.S. Pat. No. 5,122,614, issued Jun. 16, 1992 to Zalipsky; U.S. Pat. No. 5,650,234, issued to Dolence et al. Jul. 22, 1997, and references therein.

In addition to those poly(ethyleneglycol) molecules having two hydroxyl termini, those derivatives having a hydroxy terminus and a methoxy terminus are also useful in this aspect of the invention. These derivatives are commercially available and can be modified by methods identical to those used in conjunction with the bis-hydroxyl poly (ethyleneglycol) molecules.

When m is greater than one, an $R^2$ moiety having more than one amine, or other functional groups, can be used for tethering the hydrophilic polymer groups ($R^3$) to the surface ($R^1$). Appropriate $R^2$ moieties can be viewed as "amplifier molecules." An exemplary amplifier molecule is a peptide containing more than one lysine residue. In this example, a peptide bond is formed between a carboxyl group of an amino acid and either the—or the -amino group of lysine, leaving a free—or -amino group, respectively. This free amino group can be used to form a bond to the hydrophilic polymer. Other suitable amplifier molecules are known in the art. See, for example, U.S. Pat. No. 5,412148, issued May 2, 1995 to Keana; Newcome et al., *J. Am. Chem. Soc.* 108:849 (1986), and references therein.

Intermediate Linking Groups $R^1$ and $R^2$ can be connected to each other either directly or, alternatively, they can be connected through an intermediate linking group. In a preferred embodiment, the surface further comprises a linking group $R^4$ adjoining $R^1$ to $R^2$. Linking groups of use in the present invention can have a range of structures, substituents and substitution patterns. They can, for example be derivatized with nitrogen, oxygen and/or sulfur containing groups which are pendent from, or integral to, the linker group backbone. Examples include, polyethers, polyacids (polyacrylic acid, polylactic acid), polyols (e.g., glycerol, ), polyamines (e.g., spermine, spermidine) and molecules having more than one nitrogen, oxygen and/or sulfur moiety (e.g., 1,3-diamino-2-propanol, taurine).

In a further preferred embodiment, the linking group has the structure:

$$X-R^5-Y \qquad (II)$$

in which $R^5$ is —$(CH_2)_s$—; X and Y are the same or different and are inert linking groups; and s is at least 3. Inert linking groups of use in the present invention include those groups which are substantially stable under the operating conditions of the microfluidic devices onto which the coatings are layered. Inert linking groups include those in which less than 20% of the groups in a particular coating are cleaved over 150 hours of operation, more preferably, less than 10%, and more preferably still, less than 5%.

In preferred embodiment, X and Y are members independently selected from Si—Si, Si—O, —NHC(O)—, —C(O)—NH, —OC(O)—NH—, HN—C(O)O—, —SO$_3$NH—, and —HN—SO$_3$—. Many synthetic routes providing access to these linkages are known to those of skill in the art and one of skill will be able to choose appropriate reaction conditions for the formation of these and other inert bonds between the different components of the surfaces of the invention. See, for example, Sandler et al. *Organic Functional Group Preparations* $2^{nd}$ Ed., Academic Press, Inc. San Diego 1983.

Amino Acid-poly(ethyleneglycol) Surfaces

In certain preferred embodiments, the surface comprises an amino acid-poly(ethyleneglycol) conjugate according to Formula (I) in which m is 1 and —$R^2$—$R^3$ has the structure according to Formula (IV):

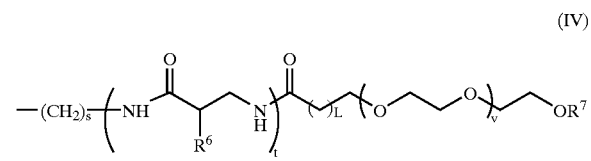

(IV)

in which, each $R^6$ is independently selected from H, —$CH_3$, —$(CH_2)_3NHC(NH)NH_2$; —$CH_2CO_2H$; —$(CH_2)_2CO_2H$ and —$(CH_2)_4NH_2$; $R^7$ is H or $CH_3$; s is an integer between 1 and 10; t is an integer between 1 and 10; u is an integer between 1 and 10; and v is and integer between 1 and 200.

By using more than one species according to Formula (IV) to form a coating, the charge density on the coating can be manipulated. For example, a coating having a 1:1 ratio of a species having $R^6$=H, and a second species having $R^6$=—$CH_2CO_2H$, the charge density of the coating will be approximately half that of a coating composed entirely of species in which $R^6=H_2CO_2H$. The intramolecular charge density can also be varied by assembling peptides using amino acids with charged side chains and amino acids with uncharged side chains.

The depth of the coating can also be systematically varied by, for example, choosing the molecular weight of the poly(ethyleneglycol) moiety. As poly(ethyleneglycol) is a predominantly linear molecule, regions in which a poly(ethyleneglycol) having a molecular weight of 100 should be approximately one-tenth as deep as those constructed with poly(ethyleneglycol) having a molecular weight of 1,000. Thus, the depth of the coating can be varied randomly, or in a patterned fashion over the device or a portion of the device. Alternatively, the depth of the coating can vary as a gradient over the length of, for example, a microchannel of a microfluidic device.

A number of synthetic routes are useful in assembling the coatings of the invention. For example, the amino acid component can be added first to the substrate in either a protected or unprotected form. The protected form is preferred. Subsequent to the addition of the amino acid, the hydrophilic polymer is attached to the amino acid by, activating the polymer, the amino acid or both the polymer and the amino acid. Alternatively, the amino acid and hydrophilic polymer can be joined into a cassette which is attached to the substrate as a unit.

Similar to those embodiments, utilizing a coating having a single amino acid within its structure, when t is greater than 1, the peptide can be synthesized directly on the surface. Alternatively, the peptide can be synthesized and subsequently attached to the surface. Moreover, the peptide can be attached to the surface and subsequently derivatized with the poly(ethyleneglycol) or the peptide-poly(ethyleneglycol) conjugate can be prepared and attached to the surface as a cassette. Other useful variations on these attachment schemes will be apparent to those of skill in the art.

Art-recognized principles of poly(ethyleneglycol) derivatization, as discussed above can be used to produce appropriate hydrophilic species. Further, generally recognized principles of peptide synthesis, particularly peptide synthesis using amino acids with carboxy and/or amino side chains are applicable in practicing this embodiment of the invention. In those embodiments, utilizing amino acids having an amino side chain, protection and deprotection strategies appropriate for the preparation of peptides with lysine and arginine are generally useful. Similarly, coupling strategies appropriate for these amino acids will find use in practicing the present invention.

In another preferred embodiment, m is equal to 1 and the amino acid fragment bears a free carboxylic acid or carboxylate. The surface of this embodiment of the invention has a structure according to Formula (V):

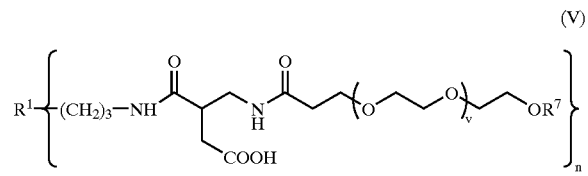

(V)

in which $R^1$ is fused silica or glass; v is an integer between 1 and 200; $R^7$ is H or $CH_3$; and n is greater than 1.

In this embodiment, the silica-based surface is derivatized with a reactive aminopropylsilyl derivative under appropriate conditions. Silylation can be performed using the pure silylation reagent or, alternatively, the silylation reagent can be used as a solution in a solvent such as alcohol, aqueous alcohol or water. In a typical silylation scenario, the silylation reagent will be contacted with the surface in a 95% ethanol-5% water solution. When aminoalkylsilanes are used, the acetic acid is omitted. The silylation reagent is generally present in an amount of from about 2% to about 10%, however, other concentrations can be used for certain applications (e.g., slow reacting silane, unstable reactive silane).

The surface is contacted with the silylating solution by dipping the plate into the solution. The silylation is followed with a rinse step in the solvent utilized for the silylation reagent. The surface, thus prepared, can then be cured at room temperature for approximately 24 hours or it can be heated at approximately 100° C. for 5–10 minutes. If necessary, the process can be repeated until a layer of the desired thickness and continuity is achieved.

In certain embodiments, a mixture of silylation reagents having different structures and/or properties will be used. This strategy allows for tuning the hydrophobicity/hydrophilicity of the coating. As discussed above, this strategy allows the depth and charge of the coating and the overall contour of the surface to be manipulated. In its simplest aspect, this embodiment includes mixing two or more different silylating reagents together in a desired ration and applying them to a surface as discussed above. In other embodiments, one or more silylating reagents can be added to a region of the device which is exposed by a mask. Following removal of the mask, a second silylating agent is added. In this manner, patterned devices can be prepared. Additional variations on these themes will be apparent to those of skill in the art.

In a preferred embodiment, the invention provides a biopolymer adsorption resistant microfluidic device comprising a glass or polymer body having at least one channel fabricated therein, the channel presenting a biopolymer adsorption resistant surface having a structure according Formula (I).

In another preferred embodiment, the present invention provides a method for reducing adsorption of charged materials in a microfluidic device having at least one microchannel therein, the method comprising, providing the microchannel having a structure according Formula (I).

In a still further preferred embodiment, the invention provides a method for producing stable-reversed flow in a microfluidic device having at least one microchannel therein, the method comprising, providing the microchannel with a surface having a structure according to Formula (I). For example, a silicon oxide anion surface of a microfluidic device channel is converted to a positively charged surface, resulting in a reversal in the direction of electroosmotic flow for a given applied electric field. This procedure is useful in some assays to keep components moving in the same direction. That is, by reversing the EO flow electrophoresis and electroosmosis act in conjunction with each other rather in opposition so that the charged molecules will move in the same direction.

Electrokinetic Material Transport

In preferred aspects, the devices, methods and systems described herein, employ electrokinetic material transport systems, and preferably, controlled electrokinetic material transport systems. As used herein, "electrokinetic material transport systems" include systems which transport and direct materials within an interconnected channel and/or chamber containing structure, through the application of electrical fields to the materials, thereby causing material movement through and among the channel and/or chambers, i.e., cations will move toward the negative electrode, while anions will move toward the positive electrode.

Such electrokinetic material transport and direction systems include those systems that rely upon the electrophoretic mobility of charged species within the electric field applied to the structure. Such systems are more particularly referred to as electrophoretic material transport systems. Other electrokinetic material direction and transport systems rely upon the electroosmotic flow of fluid and material within a channel or chamber structure which results from the application of an electric field across such structures. In brief, when a fluid is placed into a channel which has a surface bearing charged functional groups, e.g., hydroxyl groups in etched glass channels or glass microcapillaries, those groups can ionize. In the case of hydroxyl functional groups, this ionization, e.g., at neutral pH, results in the release of protons from the surface and into the fluid, creating a concentration of protons at near the fluid/surface interface, or a positively charged sheath surrounding the bulk fluid in the channel. Application of a voltage gradient across the length of the channel, will cause the proton sheath to move in the direction of the voltage drop, i.e., toward the negative electrode.

"Controlled electrokinetic material transport and direction," as used herein, refers to electrokinetic systems as described above, which employ active control of the voltages applied at multiple, i.e., more than two, electrodes. Rephrased, such controlled electrokinetic systems concomitantly regulate voltage gradients applied across at least two intersecting channels. Controlled electrokinetic material transport is described in Published PCT Application No. WO 96/04547, to Ramsey, which is incorporated herein by reference in its entirety for all purposes. In particular, the preferred microfluidic devices and systems described herein, include a body structure which includes at least two intersecting channels or fluid conduits, e.g., interconnected, enclosed chambers, which channels include at least three unintersected termini. The intersection of two channels refers to a point at which two or more channels are in fluid communication with each other, and encompasses "T" intersections, cross intersections, "wagon wheel" intersections of multiple channels, or any other channel geometry where two or more channels are in such fluid communication. An unintersected terminus of a channel is a point at which a channel terminates not as a result of that channel's intersection with another channel, e.g., a "T" intersection. In preferred aspects, the devices will include at least three intersecting channels having at least four unintersected termini. In a basic cross channel structure, where a single horizontal channel is intersected and crossed by a single vertical channel, controlled electrokinetic material transport operates to controllably direct material flow through the intersection, by providing constraining flows from the other channels at the intersection. For example, assuming one was desirous of transporting a first material through the horizontal channel, e.g., from left to right, across the intersection with the vertical channel. Simple electrokinetic material flow of this material across the intersection could be accomplished by applying a voltage gradient across the length of the horizontal channel, i.e., applying a first voltage to the left terminus of this channel, and a second, lower voltage to the right terminus of this channel, or by allowing the right terminus to float (applying no voltage). However, this type of material flow through the intersection would result in a substantial amount of diffusion at the intersection, resulting from both the natural diffusive properties of the material being transported in the medium used, as well as convective effects at the intersection.

In controlled electrokinetic material transport, the material being transported across the intersection is constrained by low level flow from the side channels, e.g., the top and bottom channels. This is accomplished by applying a slight voltage gradient along the path of material flow, e.g., from the top or bottom termini of the vertical channel, toward the right terminus. The result is a "pinching" of the material flow at the intersection, which prevents the diffusion of the material into the vertical channel. The pinched volume of material at the intersection may then be injected into the vertical channel by applying a voltage gradient across the length of the vertical channel, i.e., from the top terminus to the bottom terminus. In order to avoid any bleeding over of material from the horizontal channel during this injection, a low level of flow is directed back into the side channels, resulting in a "pull back" of the material from the intersection.

In addition to pinched injection schemes, controlled electrokinetic material transport is readily utilized to create virtual valves which include no mechanical or moving parts. Specifically, with reference to the cross intersection described above, flow of material from one channel segment to another, e.g., the left arm to the right arm of the horizontal channel, can be efficiently regulated, stopped and reinitiated, by a controlled flow from the vertical channel, e.g., from the bottom arm to the top arm of the vertical channel. Specifically, in the 'off' mode, the material is transported from the left arm, through the intersection and into the top arm by applying a voltage gradient across the left and top termini. A constraining flow is directed from the bottom arm to the top arm by applying a similar voltage gradient along this path (from the bottom terminus to the top terminus). Metered amounts of material are then dispensed from the left arm into the right arm of the horizontal channel by switching the applied voltage gradient from left to top, to left to right. The amount of time and the voltage gradient applied dictates the amount of material that will be dispensed in this manner.

Although described for the purposes of illustration with respect to a four way, cross intersection, these controlled electrokinetic material transport systems can be readily adapted for more complex interconnected channel networks, e.g., arrays of interconnected parallel channels.

Microfluidic Device Description

As used herein, the term "microscale" or "microfabricated" generally refers to structural elements or features of a device which have at least one fabricated dimension in the range of from about $0.1\mu$ to about $500\mu$. Thus, a device referred to as being microfabricated or microscale will include at least one structural element or feature having such a dimension. When used to describe a fluidic element, such as a passage, chamber or conduit, the terms "microscale," "microfabricated" or "microfluidic" generally refer to one or more fluid passages, chambers or conduits which have at least one internal cross-sectional dimension, e.g., depth, width, length, diameter, etc., that is less than $500\mu$, and typically between about $0.1\mu$ and about $500\mu$. In the devices of the present invention, the microscale channels or chambers preferably have at least one cross-sectional dimension between about $0.1\mu$ and $200\mu$, more preferably between about $0.1\mu$ and $100\mu$, and often between about $0.1\mu$ and $20\mu$. Accordingly, the microfluidic devices or systems prepared in accordance with the present invention typically include at least one microscale channel, usually at least two intersecting microscale channels, and often, three or more intersecting channels disposed within a single body structure. Channel intersections may exist in a number of formats, including cross intersections, "T" intersections, or any number of other structures whereby two channels are in fluid communication.

The body structure of the microfluidic devices described herein typically comprises an aggregation of two or more separate layers which when appropriately mated or joined together, form the microfluidic device of the invention, e.g., containing the channels and/or chambers described herein. Typically, the microfluidic devices described herein will comprise a top portion, a bottom portion, and an interior portion, wherein the interior portion substantially defines the channels and chambers of the device.

FIG. 1 illustrates a two layer body structure 10, for a microfluidic device. In preferred aspects, the bottom portion of the device 12 comprises a solid substrate that is substantially planar in structure, and which has at least one substantially flat upper surface 14. A variety of substrate materials may be employed as the bottom portion. Typically, because the devices are microfabricated, substrate materials will be selected based upon their compatibility with known microfabrication techniques, e.g., photolithography, wet chemical etching, laser ablation, air abrasion techniques, injection molding, embossing, and other techniques. The substrate materials are also generally selected for their compatibility with the full range of conditions to which the microfluidic devices may be exposed, including extremes of pH, temperature, salt concentration, and application of electric fields. Accordingly, in some preferred aspects, the substrate material may include materials normally associated with the semiconductor industry in which such microfabrication techniques are regularly employed, including, e.g., silica based substrates, such as glass, quartz, silicon or polysilicon, as well as other substrate materials, such as gallium arsenide and the like. In the case of semiconductive materials, it will often be desirable to provide an insulating coating or layer, e.g., silicon oxide, over the substrate material, and particularly in those applications where electric fields are to be applied to the device or its contents.

In additional preferred aspects, the substrate materials will comprise polymeric materials, e.g., plastics, such as polymethylmethacrylate (PMMA), polycarbonate, polytetrafluoroethylene (TEFLON), polyvinylchloride (PVC), polydimethylsiloxane (PDMS), polysulfone, polystyrene, polymethylpentene, polypropylene, polyethylene, polyvinylidine fluoride, ABS (acrylontrile-butadiene-styrene copolymer), and the like. Such polymeric substrates are readily manufactured using available microfabrication techniques, as described above, or from microfabricated masters, using well known molding techniques, such as injection molding, embossing or stamping, or by polymerizing the polymeric precursor material within the mold (See, U.S. Pat. No. 5,512,131). Such polymeric substrate materials are preferred for their ease of manufacture, low cost and disposability, as well as their general inertness to most extreme reaction conditions. Again, these polymeric materials may include treated surfaces, e.g., derivatized or coated surfaces, to enhance their utility in the microfluidic system, e.g., provide enhanced fluid direction, e.g., as described in U.S. patent application Ser. No. 08/843,212, filed Apr. 14, 1997, and which is incorporated herein by reference in its entirety for all purposes.

The channels and/or chambers of the microfluidic devices are typically fabricated into the upper surface of the bottom substrate or portion 12, as microscale grooves or indentations 16, using the above described microfabrication techniques. The top portion or substrate 18 also comprises a first planar surface 20, and a second surface 22 opposite the first planar surface 20. In the microfluidic devices prepared in accordance with the methods described herein, the top portion also includes a plurality of apertures, holes or ports 24 disposed therethrough, e.g., from the first planar surface 20 to the second surface 22 opposite the first planar surface.

The first planar surface 20 of the top substrate 18 is then mated, e.g., placed into contact with, and bonded to the planar surface 14 of the bottom substrate 12, covering and sealing the grooves and/or indentations 16 in the surface of the bottom substrate, to form the channels and/or chambers (i.e., the interior portion) of the device at the interface of these two components. The holes 24 in the top portion of the device are oriented such that they are in communication with at least one of the channels and/or chambers formed in the interior portion of the device from the grooves or indentations in the bottom substrate. In the completed device, these holes function as reservoirs for facilitating fluid or material introduction into the channels or chambers of the interior portion of the device, as well as providing ports at which electrodes may be placed into contact with fluids within the device, allowing application of electric fields along the channels of the device to control and direct fluid transport within the device.

In many embodiments, the microfluidic devices will include an optical detection window disposed across one or more channels and/or chambers of the device. Optical detection windows are typically transparent such that they are capable of transmitting an optical signal from the channel/chamber over which they are disposed. Optical detection windows may merely be a region of a transparent cover layer, e.g., where the cover layer is glass or quartz, or a transparent polymer material, e.g., PMMA, polycarbonate, etc. Alternatively, where opaque substrates are used in manufacturing the devices, transparent detection windows fabricated from the above materials may be separately manufactured into the device.

These devices may be used in a variety of applications, including, e.g., the performance of high throughput screening assays in drug discovery, immunoassays, diagnostics, genetic analysis, and the like. As such, the devices described herein, will often include multiple sample introduction ports or reservoirs, for the parallel or serial introduction and analysis of multiple samples. Alternatively, these devices may be coupled to a sample introduction port, e.g., a pipetor, which serially introduces multiple samples into the device for analysis. Examples of such sample introduction systems are described in e.g., U.S. patent application Ser. Nos. 08/761,575 and 08/760,446 each of which was filed on Dec. 6, 1996, and is hereby incorporated by reference in its entirety for all purposes.

Device Integration

Although the devices and systems specifically illustrated herein are generally described in terms of the performance of a few or one particular operation, it will be readily appreciated from this disclosure that the flexibility of these systems permits easy integration of additional operations into these devices. For example, the devices and systems described will optionally include structures, reagents and systems for performing virtually any number of operations both upstream and downstream from the operations specifically described herein. Such upstream operations include sample handling and preparation operations, e.g., cell separation, extraction, purification, amplification, cellular activation, labeling reactions, dilution, aliquoting, and the like. Similarly, downstream operations may include similar operations, including, e.g., separation of sample components, labeling of components, assays and detection operations. Assay and detection operations include without limitation, probe interrogation assays, e.g., nucleic acid hybridization assays utilizing individual probes, free or tethered within the channels or chambers of the device and/or probe arrays having large numbers of different, discretely positioned probes, receptor/ligand assays, immunoassays, and the like.

Instrumentation

The systems described herein generally include microfluidic devices, as described above, in conjunction with additional instrumentation for controlling fluid transport and direction within the devices, detection instrumentation for detecting or sensing results of the operations performed by the system, processors, e.g., computers, for instructing the controlling instrumentation in accordance with preprogrammed instructions, receiving data from the detection instrumentation, and for analyzing, storing and interpreting the data, and providing the data and interpretations in a readily accessible reporting format.

Controller

A variety of controlling instrumentation may be utilized in conjunction with the microfluidic devices described above, for controlling the transport and direction of fluids and/or materials within the devices of the present invention. For example, in many cases, fluid transport and direction may be controlled in whole or in part, using pressure based flow systems that incorporate external or internal pressure sources to drive fluid flow. Internal sources include microfabricated pumps, e.g., diaphragm pumps, thermal pumps, lamb wave pumps and the like that have been described in the art. See, e.g., U.S. Pat. Nos. 5,271,724, 5,277,556, and 5,375,979 and Published PCT Application Nos. WO 94/05414 and WO 97/02357. In such systems, fluid direction is often accomplished through the incorporation of microfabricated valves, which restrict fluid flow in a controllable manner. See, e.g., U.S. Pat. No. 5,171,132.

As noted above, the systems described herein preferably utilize electrokinetic material direction and transport systems. As such, the controller systems for use in conjunction with the microfluidic devices typically include an electrical power supply and circuitry for concurrently delivering appropriate voltages to a plurality of electrodes that are placed in electrical contact with the fluids contained within the microfluidic devices. Examples of particularly preferred electrical controllers include those described in, e.g., U.S. patent application Ser. No. 08/888,064, and International Patent Application No. PCT/US97/12930, filed Jul. 2, 1997, the disclosures of which are hereby incorporated herein by reference in their entirety for all purposes. In brief, the controller uses electric current control in the microfluidic system. The electrical current flow at a given electrode is directly related to the ionic flow along the channel(s) connecting the reservoir in which the electrode is placed. This is in contrast to the requirement of determining voltages at various nodes along the channel in a voltage control system. Thus the voltages at the electrodes of the microfluidic system are set responsive to the electric currents flowing through the various electrodes of the system. This current control is less susceptible to dimensional variations in the process of creating the microfluidic system in the device itself. Current control permits far easier operations for pumping, valving, dispensing, mixing and concentrating subject materials and buffer fluids in a complex microfluidic system. Current control is also preferred for moderating undesired temperature effects within the channels.

Typically, the controller systems are appropriately configured to receive a microfluidic device as described herein. In particular, the controller and/or detector (as described in greater detail, below), includes a stage upon which the device of the invention is mounted to facilitate appropriate interfacing between the controller and/or detector and the device. Typically, the stage includes an appropriate mounting/alignment structural element, such as a nesting well, alignment pins and/or holes, asymmetric edge structures (to facilitate proper device alignment), and the like.

Detector

In the microfluidic systems described herein, a variety of detection methods and systems may be employed, depending upon the specific operation that is being performed by the system. Often, a microfluidic system will employ multiple different detection systems for monitoring the output of the system. Examples of detection systems include optical sensors, temperature sensors, pressure sensors, pH sensors, conductivity sensors, and the like. Each of these types of sensors is readily incorporated into the microfluidic systems described herein. In these systems, such detectors are placed either within or adjacent to the microfluidic device or one or more channels, chambers or conduits of the device, such that the detector is within sensory communication with the device, channel, or chamber. The phrase "within sensory communication" of a particular region or element, as used herein, generally refers to the placement of the detector in a position such that the detector is capable of detecting the property of the microfluidic device, a portion of the microfluidic device, or the contents of a portion of the microfluidic device, for which that detector was intended. For example, a pH sensor placed in sensory communication with a microscale channel is capable of determining the pH of a fluid disposed in that channel. Similarly, a temperature sensor placed in sensory communication with the body of a microfluidic device is capable of determining the temperature of the device itself.

Particularly preferred detection systems include optical detection systems for detecting an optical property of a material within the channels and/or chambers of the microfluidic devices that are incorporated into the microfluidic systems described herein. Such optical detection systems are typically placed adjacent a microscale channel of a microfluidic device, and are in sensory communication with the channel via an optical detection window that is disposed across the channel or chamber of the device. Optical detection systems include systems that are capable of measuring the light emitted from material within the channel, the transmissivity or adsorbance of the material, as well as the materials spectral characteristics. In preferred aspects, the detector measures an amount of light emitted from the material, such as a fluorescent or chemiluminescent material. As such, the detection system will typically include collection optics for gathering a light based signal transmitted through the detection window, and transmitting that signal to an appropriate light detector. Microscope objectives of varying power, field diameter, and focal length may be readily utilized as at least a portion of this optical train. The light detectors may be photodiodes, avalanche photodiodes, photomultiplier tubes, diode arrays, or in some cases, imaging systems, such as charged coupled devices (CCDs) and the like. In preferred aspects, photodiodes are utilized, at least in part, as the light detectors. The detection system is typically coupled to the computer (described in greater detail below), via an AD/DA converter, for transmitting detected light data to the computer for analysis, storage and data manipulation.

In the case of fluorescent materials, the detector will typically include a light source which produces light at an appropriate wavelength for activating the fluorescent material, as well as optics for directing the light source through the detection window to the material contained in the channel or chamber. The light source may be any number of light sources that provides the appropriate wavelength, including lasers, laser diodes and LEDs. Other light sources may be required for other detection systems. For example, broad band light sources are typically used in light scattering/transmissivity detection schemes, and the like. Typically, light selection parameters are well known to those of skill in the art.

The detector may exist as a separate unit, but is preferably integrated with the controller system, into a single instrument. Integration of these functions into a single unit facilitates connection of these instruments with the computer (described below), by permitting the use of few or a single communication port(s) for transmitting information between the controller, the detector and the computer.

Computer

As noted above, either or both of the controller system and/or the detection system are coupled to an appropriately programmed processor or computer which functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an AD/DA converter as needed).

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation. The computer then receives the data from the one or more sensors/detectors included within the system, and interprets the data, either provides it in a user understood format, or uses that data to initiate further controller instructions, in accordance with the programming, e.g., such as in monitoring and control of flow rates, temperatures, applied voltages, and the like.

Kits

Generally, the microfluidic devices described herein, are packaged to include many if not all of the necessary reagents for performing the device's preferred function. Such kits also typically include appropriate instructions for using the devices and reagents, and in cases where reagents are not predisposed in the devices themselves, with appropriate instructions for introducing the reagents into the channels and/or chambers of the device. In this latter case, these kits optionally include special ancillary devices for filling the microfluidic channels, e.g., appropriately configured syringes/pumps, or the like. In the former case, such kits typically include a microfluidic device with necessary reagents predisposed in the channels/chambers of the device. Generally, such reagents are provided in a stabilized form, so as to prevent degradation or other loss during prolonged storage, e.g., from leakage. A number of stabilizing processes are widely used for reagents that are to be stored, such as the inclusion of chemical stabilizers (i.e., enzymatic inhibitors, microcides/bacteriostats, anticoagulants), the physical stabilization of the material, e.g., through immobilization on a solid support, entrainment in a matrix (i.e., a gel), lyophilization, or the like.

The discussion above is generally applicable to the description of the aspects and embodiments of the invention that follows. Characteristics that are specific to the aspects and embodiments described below are particularly pointed out in the discussion that follows.

Poly(ethyleneimine)-based Coatings

In addition to the desirable properties of the above described charged hydrophilic groups, it has also been discovered that hydroxyethylated poly(ethyleneimine)-based species produce a coating which, when compared to non-hydroxyethylated poly(ethyleneimine)-based coatings, is substantially more stable over time, provides better reproducibility between analyses and demonstrates dramatically reduced protein adsorption.

Thus, in a second aspect, the surface of the invention has a structure according to Formula (VI):

$$R^1-(R^2)_m \qquad (VI)$$

wherein $R^1$ is selected from organic polymers, glass and silica-based polymers; $R^2$ is a hydroxyethoxylated polyethyleneimine; and m is at least 1.

Hydroxyethylated polyethyleneimines are commercially available or they can be prepared by methods known to those of skill in the art (Aldrich Chemical Co., Milwaukee, Wis.) These molecules are generally liquid polymers that are polydisperse over a wide molecular weight range. Commercially available fractions are generally from about 40,000 daltons to about 80,000 daltons. The hydroxyethylated poly(ethyleneimines) are highly branched and have a charge density which is somewhat less than that of analogous non-hydroxyethylated polyethyleneimines.

In another preferred embodiment, the surface of the invention has a structure according to Formula (VI) and $R^1$ is selected from silica, fused silica, glass, quartz, polycarbonate, polypropylene, polystyrene, acrylic polymers, polymethylmethacrylate and its copolymers, cellulose and combinations thereof.

In a further preferred embodiment, the surface of the invention has a structure according to Formula (VI) and $R^1$ and $R^2$ are attached in a manner selected from chemisorption, physisorption, covalent bonding and combinations thereof.

In yet another preferred embodiment, the surface of the invention comprises a hydroxyethoxylated polyethyleneimine that has a formula weight ranging from about 1000 to about 140,000 daltons, more preferably from about 10,000 to about 100,000 daltons.

Linking Groups

In a still further preferred embodiment, the surface of the invention has a structure according to Formula (VI) further comprising a linking group $R^3$ adjoining $R^1$ to $R^2$. In this embodiment, $R^3$ is a group having a structure according to Formula (VII):

$$X-R^4-Y \qquad (VII)$$

in which $R^4$ is $-(CH_2)_s-$; X and Y are the same or different and are inert linking groups; and s is greater than 1. In a preferred embodiment, the inert linking groups X and Y are members independently selected from the group consisting of —NHC(O)—, —C(O)—NH, —OC(O)—NH—, HN—(O)O and —NH(CH$_2$)$_q$—, —CH(OH)—NH—, —CH(OH)—CH$_2$NH— and combinations thereof and q is greater than 1.

In another preferred embodiment, the surface of the invention has a structure according to Formula (VI) in which m is 1 and —$R^2$ has a structure according to Formula (VIII):

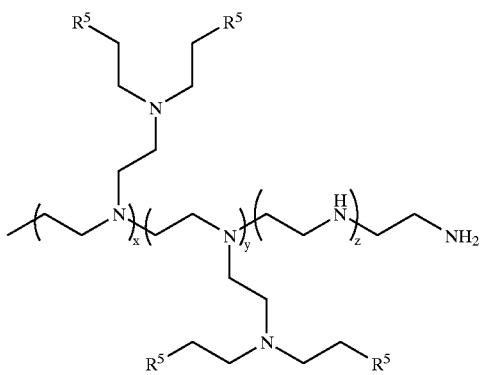
(VIII)

in which $R^5$ is a member selected from the group consisting of —$OR^6$ and $NR^6R^7$, wherein $R^6$ and $R^7$ are independently members selected from the group consisting of

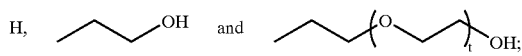

in which t is greater than 1; x is greater than 1; y is greater than 1; and z is greater than 1.

In a further embodiment, the invention provides a biopolymer adsorption resistant microfluidic device comprising a glass or polymer body having at least one channel fabricated therein, the channel presenting a biopolymer adsorption resistant surface having a structure according to Formula (VI).

In yet another preferred embodiment, the invention provides a method for reducing adsorption of charged materials in a microfluidic device having at least one microchannel therein, the method comprising, providing the microchannel with a surface having a structure according to Formula (VI).

In a still further preferred embodiment, the present invention provides a method for producing stable-reversed flow in a microfluidic device having at least one microchannel therein, the method comprising, providing the microchannel with a surface having a structure according to Formula (VI).

Method of Manufacturing

In a third aspect, the present invention provides a method of manufacturing a biopolymer adsorption resistant microfluidic device having at least one microchannel therein. The at least one microchannel has a surface. The method of the invention comprises, derivatizing the surface of the microchannel with a first surface modifying agent. The surface modifying agent can include the amino acid-poly (ethyleneglycol) and/or hydroxyethylated poly (ethyleneimine) constructs of the invention. The derivatizing can be carried out by any of the methods described herein or known to those of skill in the art. The extent of the derivitization is monitored by establishing an electroosmotic flow of a material within the channel. A property of the flow is measured and quantified. The property is then compared with a reference value for the property, thereby monitoring the extent of the derivitization.

The measured property of the electroosmotic flow can be, for example, the ability to move one or more uncharged or charged species through the microchannel. Alternatively, the property measured can be the ability of the flow to differentially move two or more charged or uncharged species through the microchannel. The ability to move the species through the channel can be quantified in units of time, liquid volume, voltage, peak separation and combinations thereof. In a preferred embodiment of this aspect of the invention, the reference value is determined by performing electroosmotic flow in a microfluidic device with a channel having a surface which is not derivatized with a surface modifying reagent.

The surface coating can be built up in a series of steps as described above. In one embodiment, a first coating subunit is added to the surface. Subsequently, a second coating subunit is added to the surface, the second subunit binding to the first. Alternatively, the overall coating can comprise more than one molecular species, each species being added to the substrate separately.

In those embodiments, in which the coating includes more than one subunit, the first subunit is attached to the substrate, as described above. Generally, any excess first subunit will be removed from the device by, for example, rinsing the device with a solvent for the first subunit. Following the attachment of the first subunit, a second subunit is added together with any reagents necessary to effect the coupling of the first and second subunits. In one exemplary embodiment, a silicon-based linker arm that terminates in an amine moiety is tethered to the substrate in a manner that leaves a free amine. The second subunit, for example, a monocarboxy poly(ethyleneglycol) is then added together with an agent suitable for condensing an amine and carboxylic acid. A wide array of appropriate condensing agents are known to those of skill in the art, including, but not limited to, carbodiimides, activated esters, carbonyldiimidazoles and the like.

In an exemplary embodiment, the coating comprises two or more distinct molecules. Thus, as discussed above, as a first coating component, a silicon-based linker arm is tethered to the substrate. An amount of a second coating component that is less than the total of available reactive amines is then added to the substrate together with any reagents necessary to couple the linker arm and the second component. At the completion of this reaction, there remains a population of available reactive amines which can then be reacted with a third coating component. This strategy can be followed to produce a wide range of structurally diverse coatings.

In yet another embodiment, the second and third coating components can be mixed together and added to the linker arm derivatized substrate. Many different variations on the strategy of building the coating up in a step-wise manner and the underlabeling strategy are available and will be apparent to those of skill in the art.

Thus, in one preferred embodiment, the method further comprises, prior to monitoring the extent of derivitization with the first subunit, derivatizing the surface with a second surface modifying agent and monitoring the extent of surface derivatization by measuring and quantifying a property of the electroosmotic flow and comparing the value with a reference value for the property, as described above.

The number of subunits is not limited to one or two, and coatings comprising a number of subunits can be used in practicing the present invention. Thus, in an additional preferred embodiment, the method of the invention further comprises, prior to monitoring the extent of derivitization with a particular subunit, derivatizing the surface with n surface modifying agents; wherein, n is a number between 1 and 100. The extent of surface derivatization is monitored by; and monitoring measuring and quantifying a property of the electroosmotic flow and comparing the value with a reference value for the property, as described above.

In a fourth aspect, the present invention provides a method of manufacturing a biopolymer adsorption resistant microfluidic device having at least one microchannel therein. In this aspect, the surface coating is monitored after the addition of each subunit and the microchannel has a surface coating comprising n subunits. The method comprises, (a) derivatizing the surface of the microchannel with a surface modifying agent; (b) monitoring the extent of the derivatizing by; (i) establishing an electroosmotic flow of a material within the channel; (ii) measuring a property of the flow to obtain a value; (iii) comparing the value with a reference value for the property, thereby monitoring the extent of the providing; and (c) repeating steps (a) and (b) n−1 times.

In the embodiments utilizing multiple coating subunits, the monitoring can be carried out substantially similarly to that described in reference to the aspect in which the coating is added as a single moiety.

The coatings, methods and devices of the invention are further illustrated by the examples that follow. These examples are offered to illustrate, but not to limit the claimed invention.

EXAMPLES

Example 1 demonstrates that microfluidic devices having a hydroxyethylated poly(ethyleneimine) coating adsorb substantially less protein than analogous microfluidic devices coated with non-hydroxyethylated poly(ethyleneimine).

Example 2 illustrates enzyme $K_m$ and inhibition assays on microfluidic devices that have been coated with hydroxyethylated poly(ethyleneimine). The hydroxyethylated poly (ethyleneimine) surfaces do not significantly adsorb proteins and, thus. eliminate the need for zwitterionic buffer additives.

Example 3 illustrates the resistance of the coatings of the invention to protein adsorption by assaying bovine serum albumin (BSA) and avidin as representative proteins.

Example 4 illustrates a synthetic strategy for coating microfluidic devices with a charged poly(ethyleneglycol) derivative wherein indirect covalent bonding via silane or polymer linkers were employed.

Example 5 illustrates an alternative synthetic strategy for coating microfluidic devices with a charged poly (ethyleneglycol) derivative via indirect covalent bonding.

Example 6 illustrates the stability of the coatings of the invention.

Example 7 demonstrates a synthetic strategy for preparing PEG coated microfluidic devices via direct covalent modification through a silane bond. Further, the resistance to protein adsorption imparted to microfluidic devices by PEG coating is demonstrated by measuring protein adsorption in a HSA-binding assay.

Example 8 illustrate a synthetic strategy for coating microfluidic devices via Van der Waals force, hydrogen bonding or electrostatic interaction.

Example 1

Example 1 provides a comparison of biopolymer adsorption in devices coated with PEI-1 and PEI-2. PEI-1 is a branched polyethyleneimine with average MW=25,000. PEI-2 is also a branched polyethyleneimine with a base polymer MW=70,000 and has 80% of the amino groups ethoxylated. Both polymers were used to coat microfluidic devices to generate stable, reversed electroosmotic flow. The PEI-2 coating was found to exhibit less protein adsorption than the PEI-1 coating, as judged by comparing electroosmotic flow measurements and PTP1b enzyme assay results for the coated devices.

1.1 Materials and Methods
1.1 a PEI Coated Devices

The microfluidic devices used for enzyme assays measuring electroosmotic mobility (EO), had the channel format shown FIGS. 9(a) and 9(b) (with 20 µm deep channels). The top surfaces of new devices were treated with Repel-Silane-ES. The microchannels were cleaned prior to coating by successive rinses with 1N NaOH, water, 1N HCl, water and ethanol, and then dried overnight at 100–120° C. The devices were coated by filling the microchannels with the coating solution (8% PEI-1/water/ethanol or 8% PEI-2/water) and leaving overnight, followed by extensive rinsing with water. The devices were stored dry after coating. The devices were conditioned by running assay buffer through the device for 10 minutes before starting the assay, and were rinsed extensively with water after running the assay.

Figure 2:
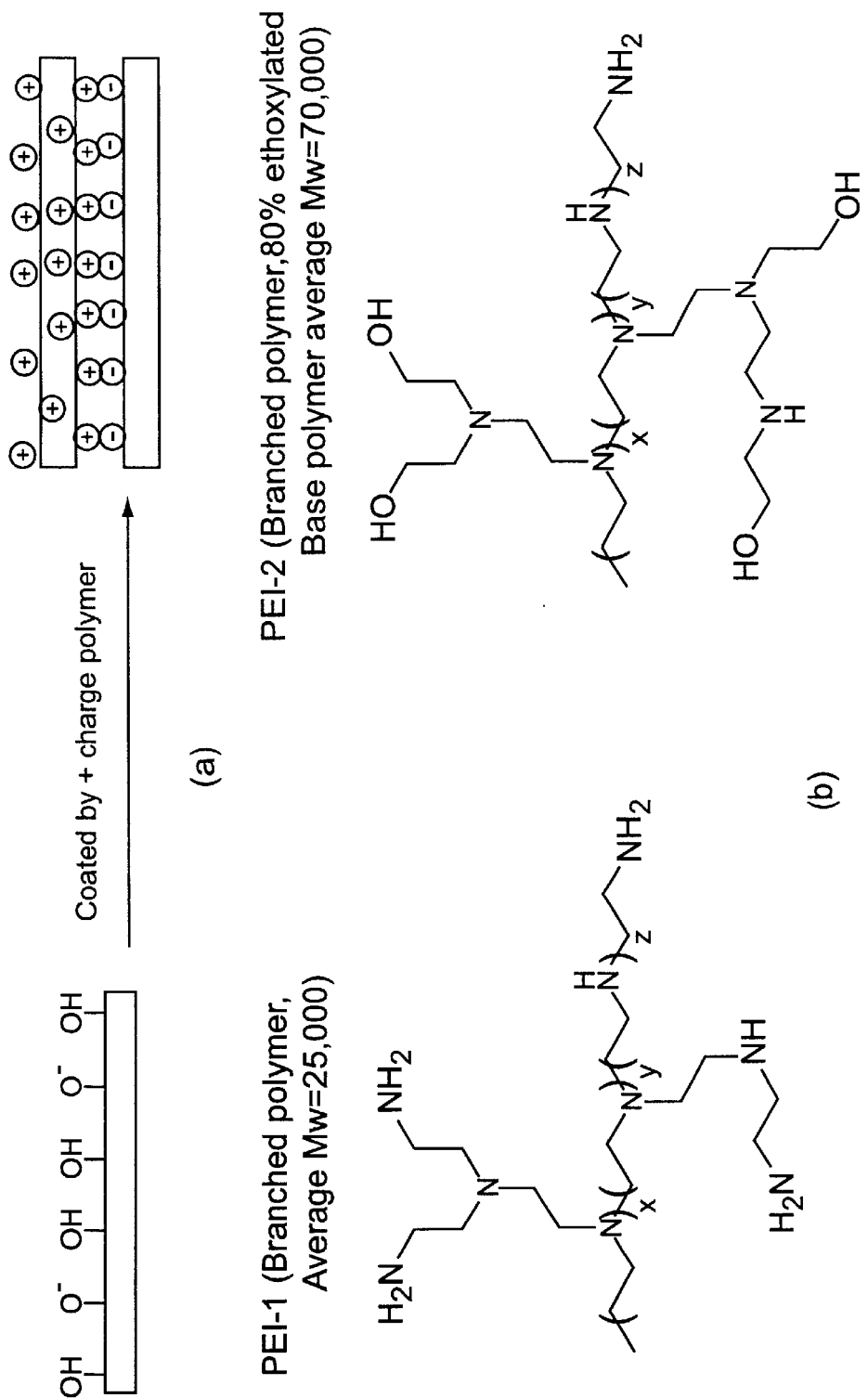
FIG. 2 (a) is a cartoon displaying a charged surface before and after coating with a charged polymer; and (b) the structural formulae of poly(ethyleneimine) (PEI-1) and hydroxyethylated (poly(ethyleneimine) (PEI-2).

A cartoon of a device having a charged surface that is coated with a charged polymer is shown in FIG. 2(a). Structural formulae for PEI-1 and PEI-2 are displayed in FIG. 2(b).

1.1b Reagents

For measurements of electroosmotic mobility in the uncoated and coated devices, Rhodamine-B (5 µM in 50 mM Hepes) was used as a neutral marker. A solution of Hepes (50 mM, pH 7.5) was used as the running buffer.

The PTP1b enzyme assays were run using an assay buffer consisting of 50 mM (Hepes, pH=7.5, conduct.=1.6mS/cm) and dithiothreitol (10 mM). The enzyme solutions were a 1:20 dilution of 1 mg/ml PTP1b (MW=65,000) in the assay buffer. The substrate for the enzyme assays was diFMUP (125 µM stock solution in the assay buffer).

1.1c Electroosmotic Mobility Measurements

Electroosmotic mobility was measured using the neutral dye injection method. A plug of Rhodamine-B was loaded in the main channel of a microfluidic device by flowing the dye from well 6 to well 3, and then injected by switching to a flow of buffer from well 1 to well 4 using the time/current profile shown in Script 1. The fluorescence signal was detected at the end of the main channel, and the mobility then calculated from the measured transit time using the relationship displayed in Equation 2.

$$\text{Mobility } (\mu eo) = v/E = (1/t)/(V/d) \qquad (2)$$

where t is the transit time in seconds, l is the distance from the injection point to the detection point in centimeters, V is the voltage applied between well 1 and well 4, and d is the length of the channel between well 1 and well 4.

The electroosmotic mobilities of PEI-1 and PEI-2 coated devices were measured before and after running the PTP1b enzyme assay.

| | Script 1 | | | | | | | | |
|---|---|---|---|---|---|---|---|---|---|
| | Wells | | | | | | | | Time |
| State # | 1 | 2 | 3 | 4 | 5 | 6 | 7 | 8 | (sec) |
| 1 | −1 | 0 | 1500 V | −1 | 0 V | −8 | 0 | 0 | 10 |
| 2 | 300 V | 0 | 0.2 | 1500 V | 0 V | 0.2 | 0 | 0 | 50 |

1.1d Measurements

The $K_m$ for the PTP1b/diFMUP reaction was determined from substrate titration studies using the time/current profile shown in Script 2. In this experiment, a 0.1 mg/ml PTP1b solution (12 µl) was placed in well 8. A 6.25 µM diFMUP solution (12 µl) was placed in well 2. A 50 mM Hepes buffer solution (12 μl) was placed in the other wells. The fluorescence signal was detected at the end of the main channel. The first 5 steps were substrate-only titration steps using well 2 and well 3, with buffer flow from well 1. The next 5 steps were the same substrate titration series with enzyme flowing from well 8. The difference between the combined enzyme and substrate signal and the substrate-only background signal was the product signal.

In order to extend the substrate concentration range in these studies, 12.5 μM and 25 μM diFMUP solutions were placed in well 2 and the same script was run again. The final concentrations of the enzyme and substrate were calculated from the known well concentration and the ratio of currents programmed in the script. Lineweaver-Burk plots of 1/(product signal per unit time) vs. 1/(substrate concentration) yield estimates of $K_m$ as determined from the slope divided by the y-intercept.

| | | | Script 2 | | | | | |
|---|---|---|---|---|---|---|---|---|
| State | | | Wells | | | | | Time |
| # | 1 | 2 | 3 | 4 | 5 | 6 | 7 | 8 | (sec) |
| 1 | 0.2 | −1.5 | 0 | 1500 V | 0 V | 0 | −2 | −3.2 | 50 |
| 2 | 0 | −1.5 | 0 | 1500 V | 0 V | −0.5 | −1.5 | −3 | 50 |
| 3 | 0 | −1.5 | 0 | 1500 V | 0 V | −1 | −1 | −3 | 50 |
| 4 | 0 | −1.5 | 0 | 1500 V | 0 V | −1.5 | −0.5 | −3 | 50 |
| 5 | 0 | −1.5 | 0 | 1500 V | 0 V | −2 | 0 | −3 | 50 |
| 6 | −0.5 | −1.5 | −1 | 1500 V | 0 V | 0 | −2 | −1.5 | 50 |
| 7 | −3 | −1.5 | −1 | 1500 V | 0 V | −0.5 | −1.5 | 0 | 50 |
| 8 | −3 | −1.5 | 0 | 1500 V | 0 V | −1 | −1 | 0 | 50 |
| 9 | −3 | −1.5 | 0 | 1500 V | 0 V | −1.5 | −0.5 | 0 | 50 |
| 10 | −3 | −1.5 | 0 | 1500 V | 0 V | −2 | 0 | 0 | 50 |

1.2 Results

Figure 3:
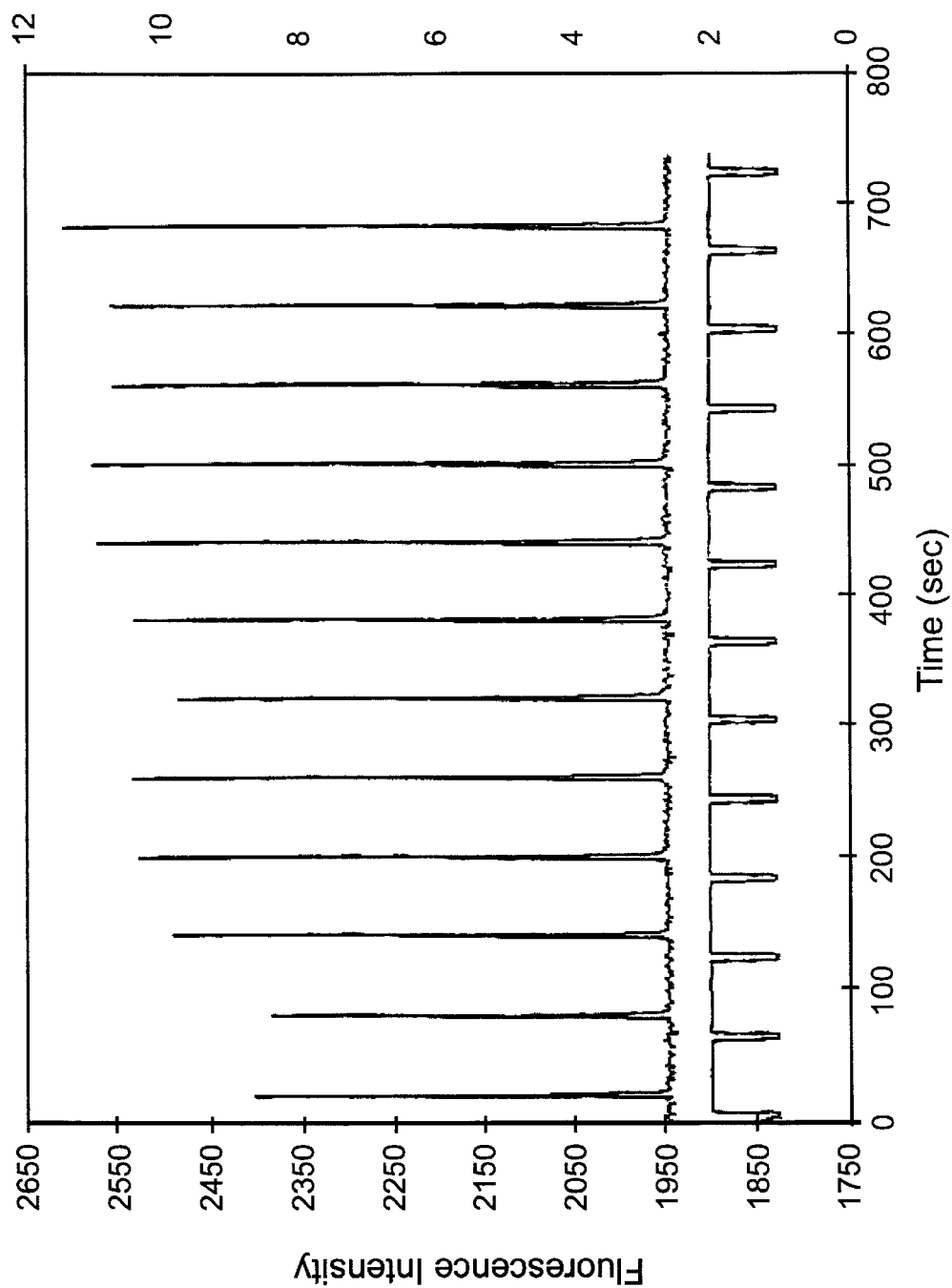
FIG. 3 is a plot of fluorescence intensity vs. time for a neutral marker in a PEI-1 coated microfluidic device prior to exposing the device to protein.
Figure 4:
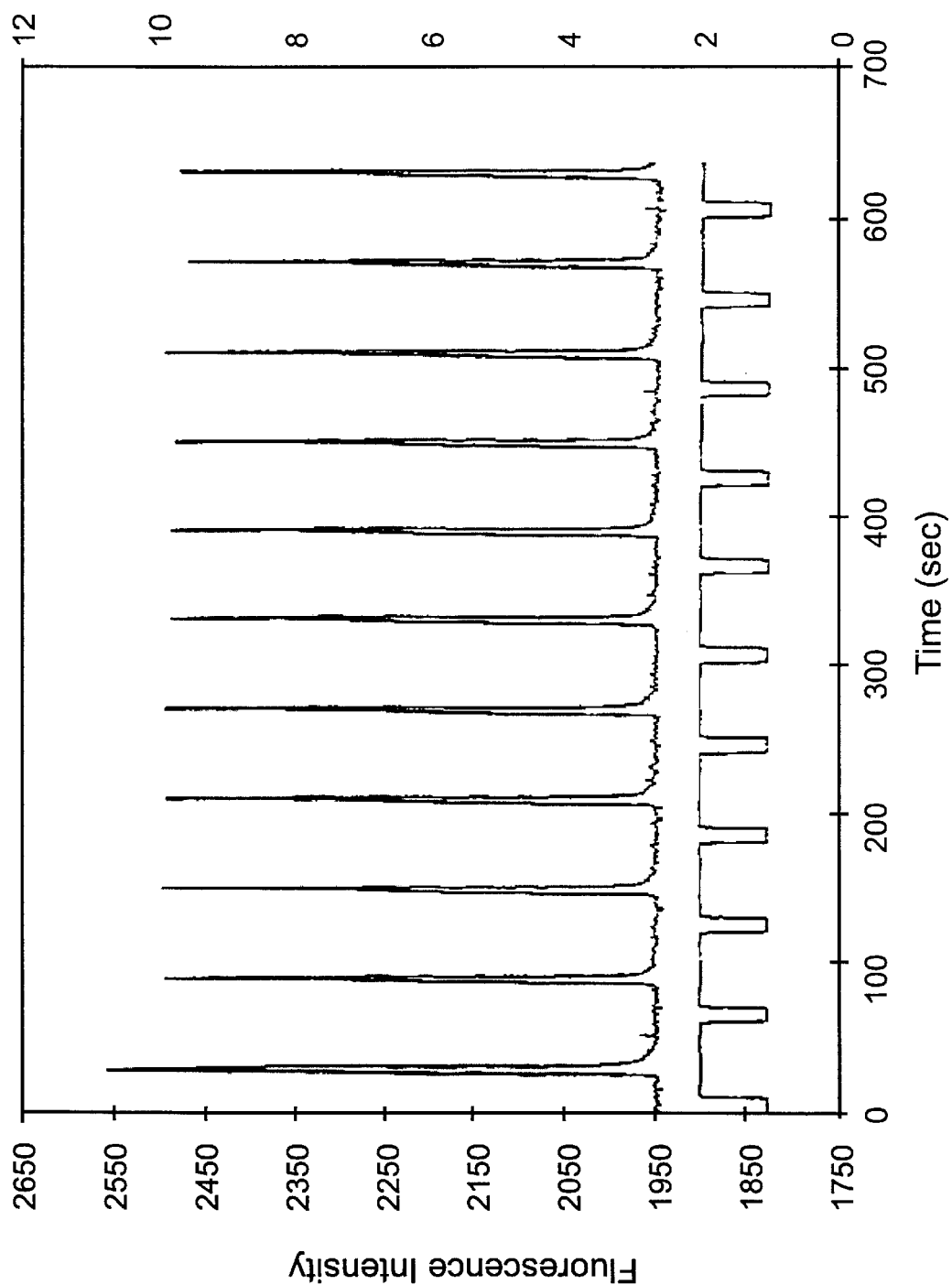
FIG. 4 is a plot of fluorescence intensity vs. time for a neutral marker in a PEI-2 coated microfluidic device prior to exposing the device to protein.
Figure 5:
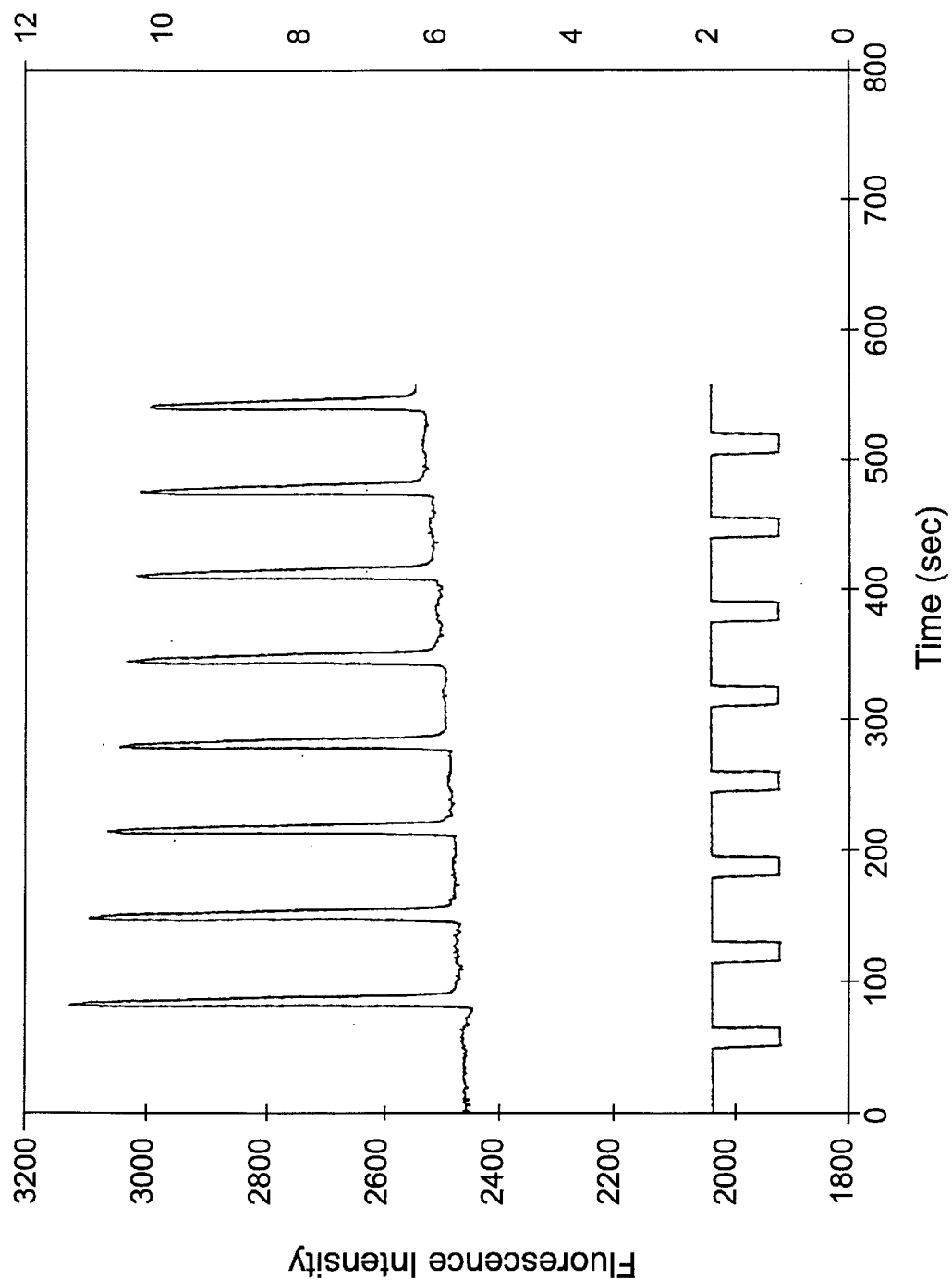
FIG. 5 is a plot of fluorescence intensity vs. time for a neutral marker in a PEI-1 coated microfluidic device after exposing the device to protein.
Figure 6:
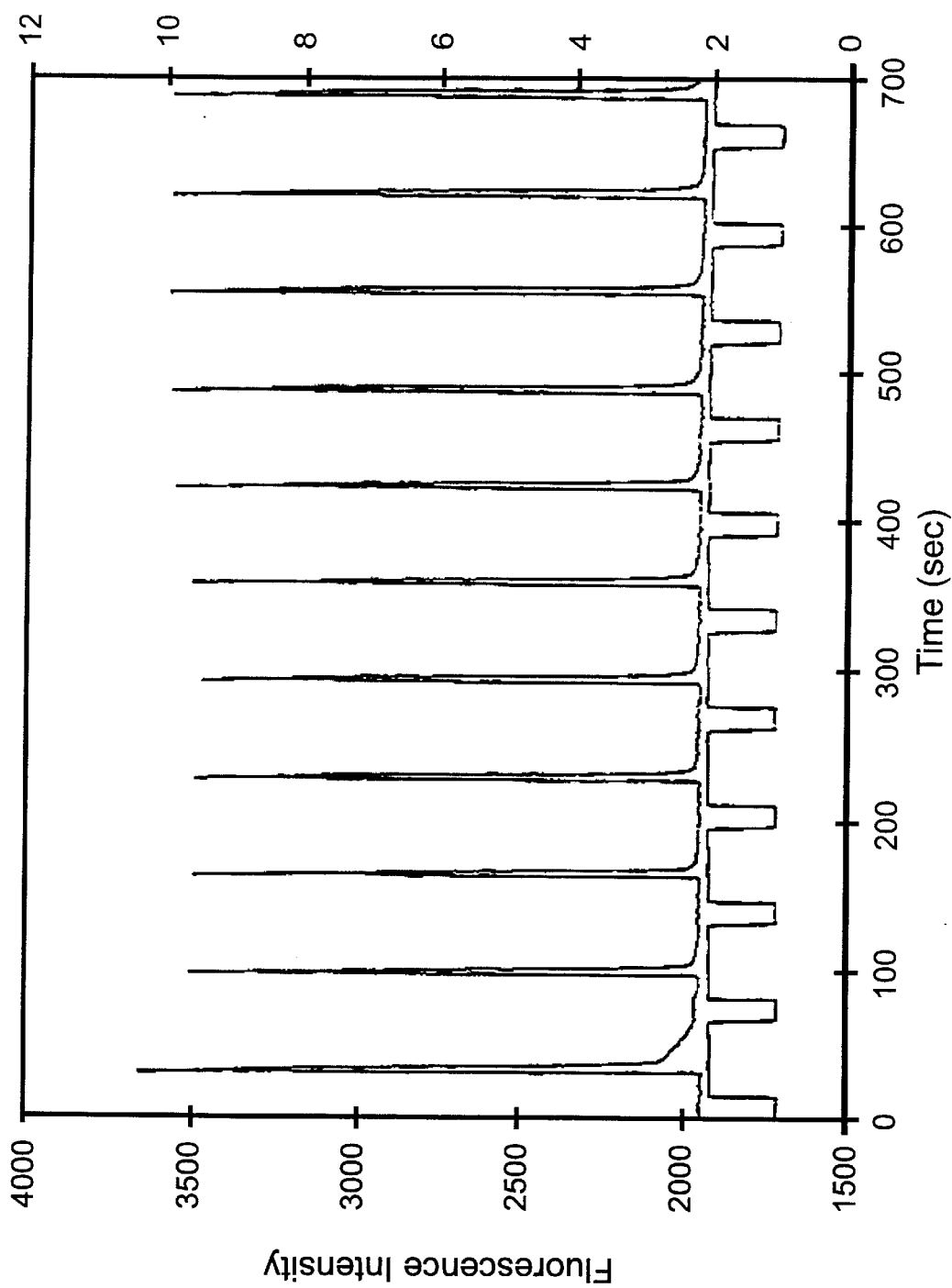
FIG. 6 is a plot of fluorescence intensity vs. time for a neutral marker in a PEI-2 coated microfluidic device after exposing the device to protein.

In electroosmotic mobility (EO) measurements using freshly prepared devices, clean dye injection peaks were observed for both PEI-1 and PEI-2 coated devices (FIG. 3 and FIG. 4). After running the PTP1b enzyme assay, the dye injection peaks became broader for the PEI-1 coated devices, while no change was observed for the PEI-2 coated devices (FIG. 5 and FIG. 6).

Table 1 summarizes the EO mobility data for PEI-1 and PEI-2 coated devices. It was found that after running the PTP1b assay for about 1 hour, the mobility of PEI-1 coated devices dropped dramatically, while the EO mobility of PEI-2 coated devices remained nearly constant. Since the EO mobility is proportional to the zeta potential of the capillary wall, larger changes in EO mobility should imply greater adsorption of protein. It is concluded that the PEI-1 coating exhibits significantly more PTP1b protein adsorption than the PEI-2 coating.

TABLE 1

| Mobility (cm$^2$/kV sec) | Before assay | After assay | Difference |
|---|---|---|---|
| PEI-1 coated device | 0.272 | 0.190 | 30.0% |
| PEI-2 coated device | 0.223 | 0.211 | 5.6% |

Figure 7:
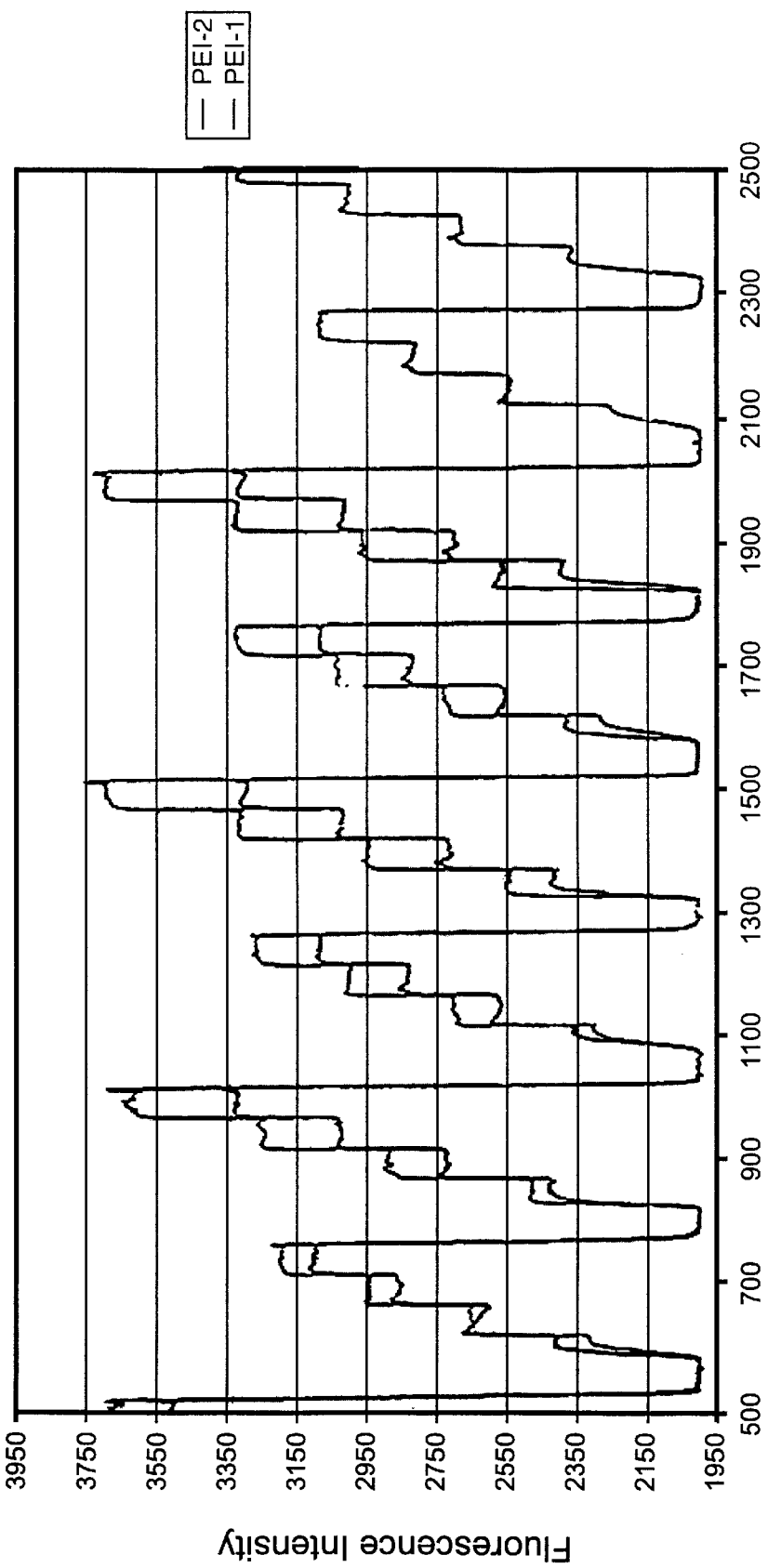
FIG. 7 is a plot of fluorescence intensity vs. time for a substrate titration experiment.
Figure 8:
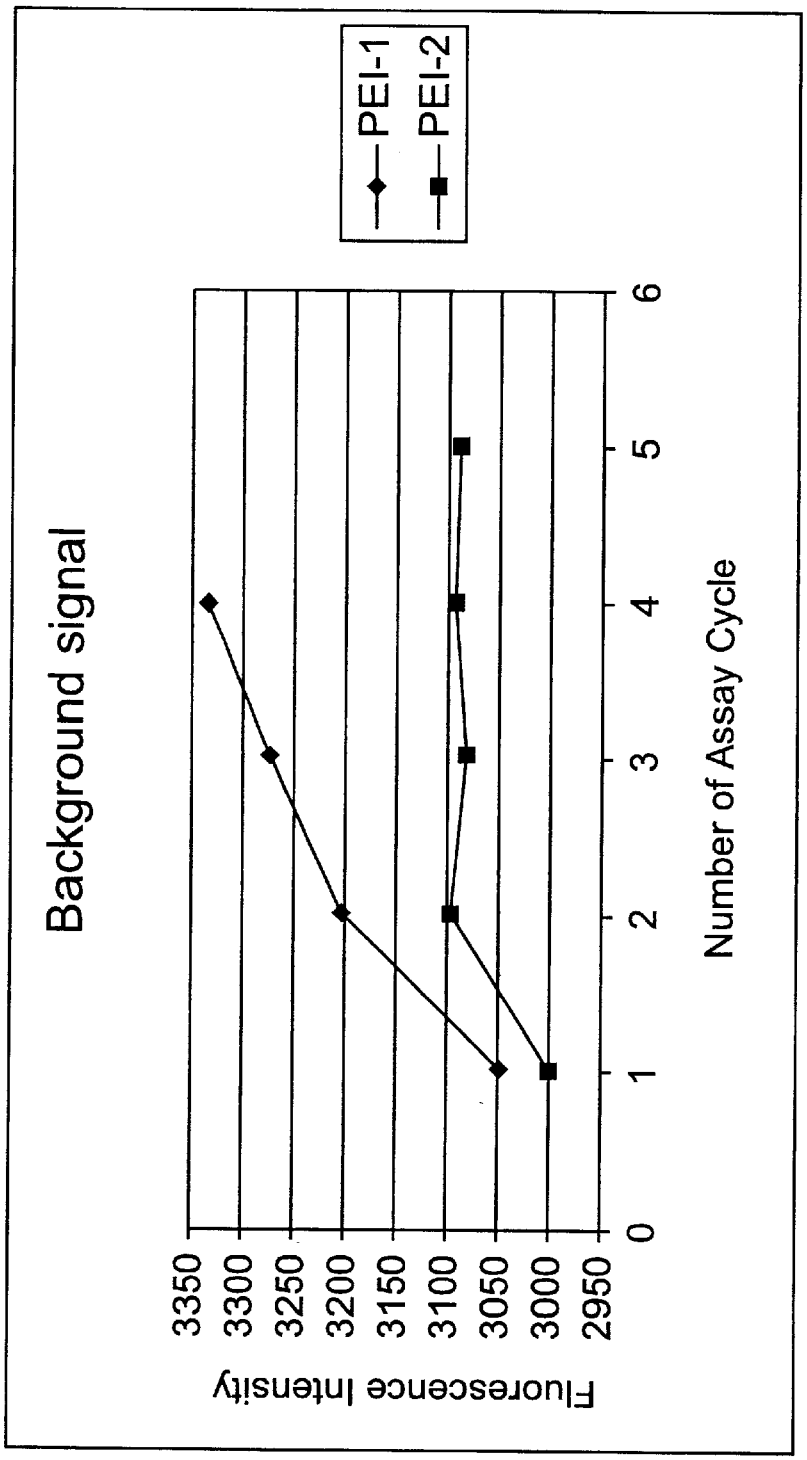
FIG. 8 is a plot of substrate only background signal vs. the cycle number for each titration experiment.

Greater protein adsorption to PEI-1 coated devices is also evident in the results of the PTP1b assay itself. FIG. 7 shows the fluorescence traces for a substrate titration experiment. FIG. 8 shows the substrate-only background signal vs. the cycle number for each titration series. It was found that the substrate-only background signal for PEI-1 coated devices kept increasing, while the substrate-only background signal for PEI-2 coated devices increased only between the first and second cycles, and then remained constant. The change in "substrate-only" signal arises from the reaction between substrate and enzyme adsorbed to the capillary wall. The larger changes observed for PEI-1 coated devices imply that more protein adsorption occurred with the PEI-1 coating than with the PEI-2 coating.

Two polyethyleneimine coatings were examined and their protein adsorption properties compared. The PEI-2 coating makes use of a polymer in which 80% of the amino groups are ethoxylated. PEI-2 coated devices showed significantly less protein adsorption than PEI-1 coated devices, as assessed by EO mobility measurements and PTP1b enzyme assay results.

Example 2

A PTP1B assay using Caliper's microfluidic device is illustrated in Example 2. The microfluidic device surface has been modified with a physically adsorbed high-molecular-mass polyethyleneimine coating. The coating provides a stable, reversed electroosmotic flow surface. Devices coated with 80% ethoxylated polyethyleneimine (PEI-2) exhibited good electroosmotic flow (reversed direction), and show much less protein adsorption for both positively and negatively charged proteins than uncoated glass devices. In uncoated glass devices, the assay is typically run with added sulfobetaine (NDSB) to prevent the adsorption of the enzyme to the walls of the microchannel. Thus, as an additional test of PEI-2 coated devices, the PTP1B assay was run using buffers which did not contain NDSB.

2.1. Materials and Methods 2.1a PEI-2 Coated Devices

The devices used for this assay had a channel format as shown in FIGS. 9(a) and 9(b) (20 μm depth). The channel surfaces of each new device's surface was treated with Repel-Silane-ES. The channels were washed with 1N NaOH, water, 1N HCl, water and ethanol, and then dried overnight at 100–120° C. before coating. The devices were coated by filling with 8% PEI/water solution and leaving overnight, then rinsed with water and stored dry. The devices were conditioned by running the assay buffer for 10 minutes before starting the assay, and washed with water after running the assay.

2.1b Reagents

The PTP1b enzyme assays were run using an assay buffer consisting of 50 mM Hepes (pH=7.5, conductivity=1.6 mS/cm) and dithiothreitol (10 mM). The enzyme solutions were a 1:10 and 1:20 dilution of 1 mg/ml PTP1b (MW=65, 000) in the assay buffer.

The substrate for the enzyme assays was diFMUP, (25 μM stock solution in assay buffer). A known inhibitor of PTP1b was used at 500 μM in the assay buffer.

2.1c. $K_m$ Measurement

The $K_m$ value for the PTP1b/diFMUP reaction was measured from substrate titration experiments using the time/current profile shown in Script 3 (all units shown are μA unless otherwise noted). A 0.1 mg/ml PTP1b solution (12 μl) was placed in well 8. A 6.25 μM diFMUP solution (12 μl) was placed in well 2, and a 50 mM Hepes buffer solution (12 μl) was placed in the other wells. The fluorescence signal is detected at the end of the main channel. The arrangement of the device used in the $K_m$ measurement experiments is shown in FIG. 9(a).

The first 5 steps are substrate-only titrations using well 2 and well 3, with buffer flow from well 1. These provide measurements of the substrate background signal. The next 5 steps are the same substrate titration steps, but with enzyme flowing from well 8. The difference between these signals and the substrate-only background signal is product signal. In order to extend the substrate concentration range, either 12.5 μM or 25 μM diFMUP were placed in well 2 and the experiment was repeated using the same script. The final concentration of the substrate was calculated from the known well concentration and the ratio of currents as programmed in the script. Plotting 1/(product signal per unit time) vs. 1/(substrate concentration) yields the Lineweaver-Burk plot with $K_m$ equal to slope divided by the y-intercept.

Script 3

| State | Wells | | | | | | | | Time |
|---|---|---|---|---|---|---|---|---|---|
| # | 1 | 2 | 3 | 4 | 5 | 6 | 7 | 8 | (sec) |
| 1 | −4 | 0 | −2 | 1500 V | 0 V | −0.1 | 0 | 0 | 75 |
| 2 | −4 | −0.5 | −1.5 | 1500 V | 0 V | −0.1 | 0 | 0 | 75 |
| 3 | −4 | −1 | −1 | 1500 V | 0 V | −0.1 | 0 | 0 | 75 |
| 4 | −4 | −1.5 | −0.5 | 1500 V | 0 V | −0.1 | 0 | 0 | 75 |
| 5 | −4 | −2 | 0 | 1500 V | 0 V | −0.1 | 0 | 0 | 75 |
| 6 | −2 | 0 | −2 | 1500 V | 0 V | −2.1 | 0 | 0 | 75 |
| 7 | 0 | −0.5 | −1.5 | 1500 V | 0 V | −0.1 | 0 | −4 | 75 |
| 8 | 0 | −1 | −1 | 1500 V | 0 V | −0.1 | 0 | −4 | 75 |
| 9 | 0 | −1.5 | −0.5 | 1500 V | 0 V | −0.1 | 0 | −4 | 75 |
| 10 | 0 | −2 | 0 | 1500 V | 0 V | −0.1 | 0 | −4 | 75 |

2.1d. Inhibition

Figure 9:
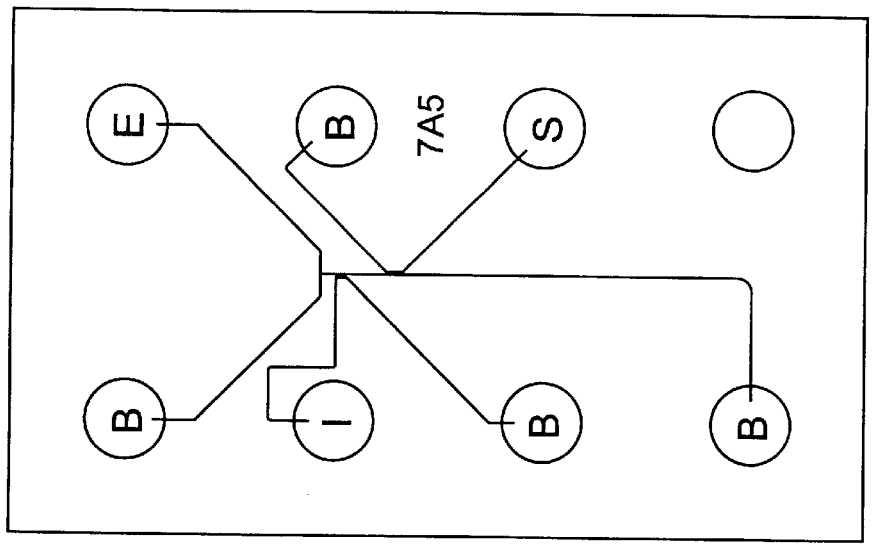
FIG. 9 (a) is a cartoon showing the layout of the microfluidic device used for a Km determination; and (b) is a cartoon showing the device layout for an enzyme inhibition study.
Figure 9:
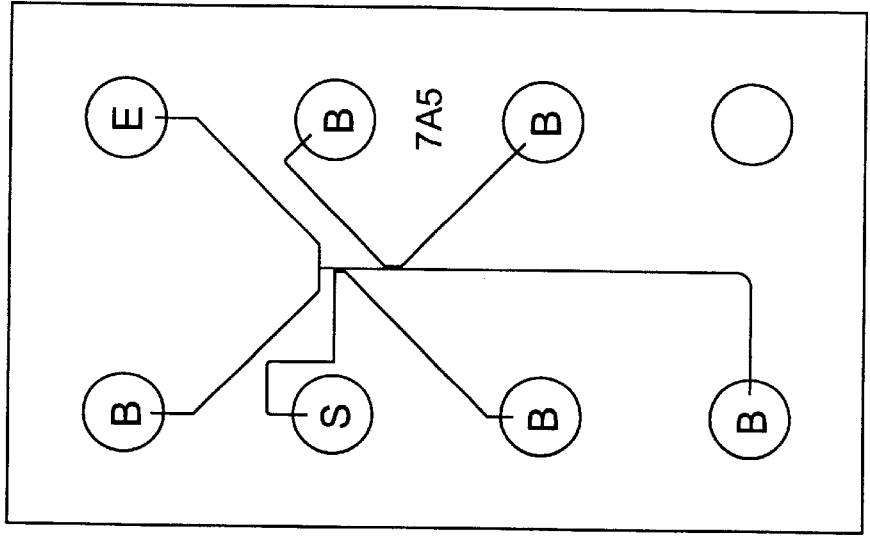

Inhibition was demonstrated using a continuous flow of enzyme and substrate, and toggling a known inhibitor on and off at different concentrations. A 0.05 mg/ml PTP1b solution (12 μl) was placed in well 8. A 250 μM diFMUP solution (12 μl) was placed in well 6. A 500 μM inhibitor solution (12 μl) was placed in well 2, and 50 mM Hepes buffer (12 μl) was placed in the other wells. The programmed flow in the device was controlled using the time/current profile shown in Script 4. The arrangement of the device used in the inhibition experiments is shown in FIG. 9(*b*).

The fluorescence signal was detected at the end of the main channel. The inhibitor tested carried a net charge of −4. No inhibition was observed in previous experiment's using non-coated glass devices, presumably because the inhibitor's electrophoretic mobility is greater than the electroosmotic mobility of glass so that it flows in the wrong direction.

Script 4

| State | Wells | | | | | | | | Time |
|---|---|---|---|---|---|---|---|---|---|
| # | 1 | 2 | 3 | 4 | 5 | 6 | 7 | 8 | (sec) |
| | 0 | 0.3 | −5 | 1500 V | 0 V | −3 | 0 | −3 | 50 |
| | 0 | −5 | 0 | 1500 V | 0 V | −3 | 0 | −3 | 15 |
| | 0 | 0.3 | −5 | 1500 V | 0 V | −3 | 0 | −3 | 50 |
| | 0 | −2.5 | −2.5 | 1500 V | 0 V | −3 | 0 | −3 | 15 |

2.2 Results

Figure 10:
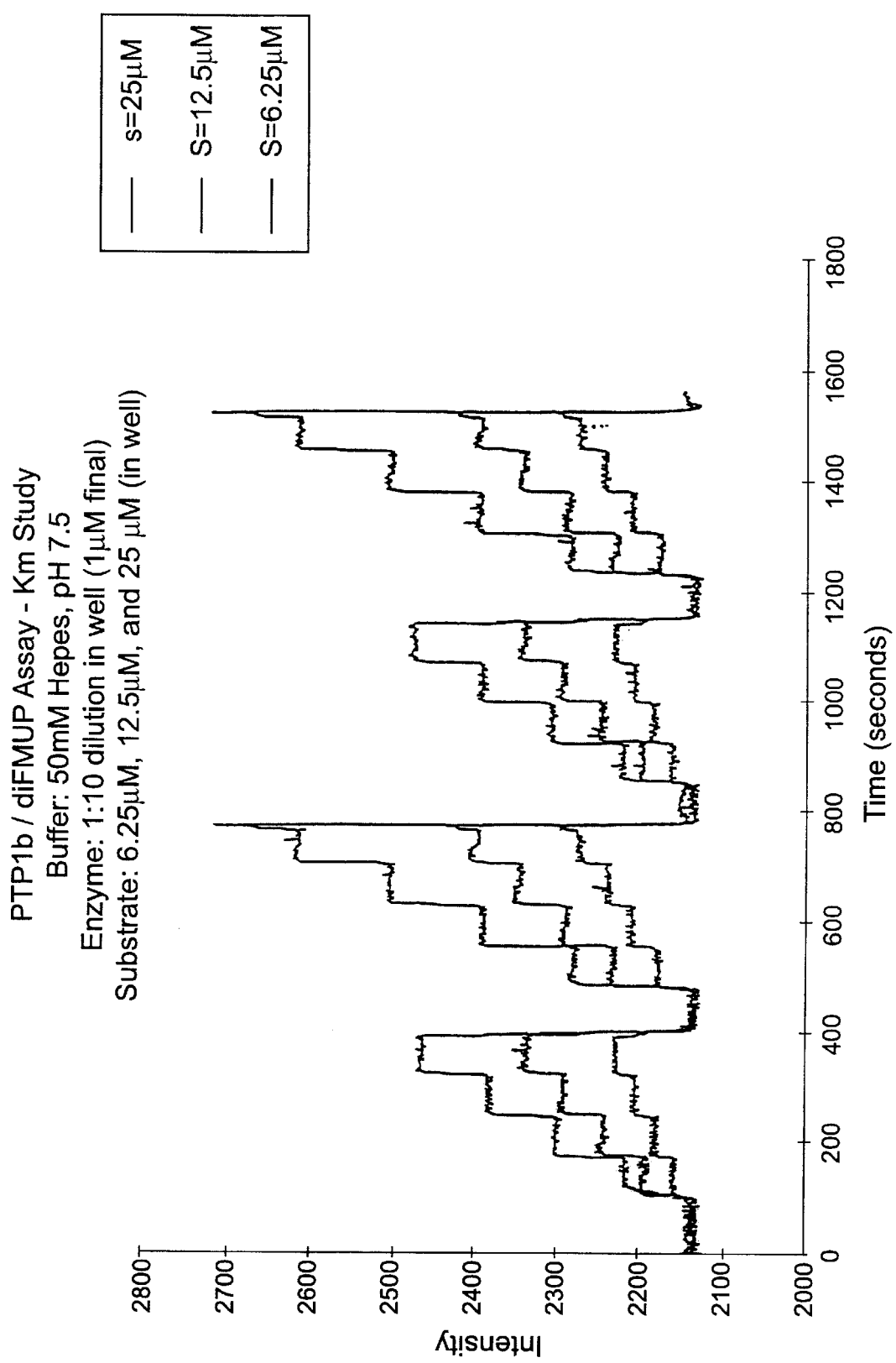
FIG. 10 is a plot of fluorescence intensity vs. time for a PTP1b $K_m$ assay in a PEI-2 coated microfluidic device

Typical fluorescence traces for the continuous-flow assay are shown in FIG. 10. The first five plateaus represent the stepped increase of substrate concentration, and correspond to the substrate-only background signal for diFMUP. The next five plateaus represent the signal for the same substrate titration series in the presence of enzyme. These signals are the sum of product (diFMU) signal and the unreacted diFMUP signal. The substrate concentration range was extended by manually refilling well 2 with different starting concentrations of diFMUP. The appearance of enzyme-dependent signal, with clean transitions between different substrate and/or enzyme levels, indicates that both the PTP1b enzyme and the diFMUP substrate can be pumped electrokinetically in PEI-2 coated devices without adding zwitterions such as NDSB to the running buffer.

Figure 11:
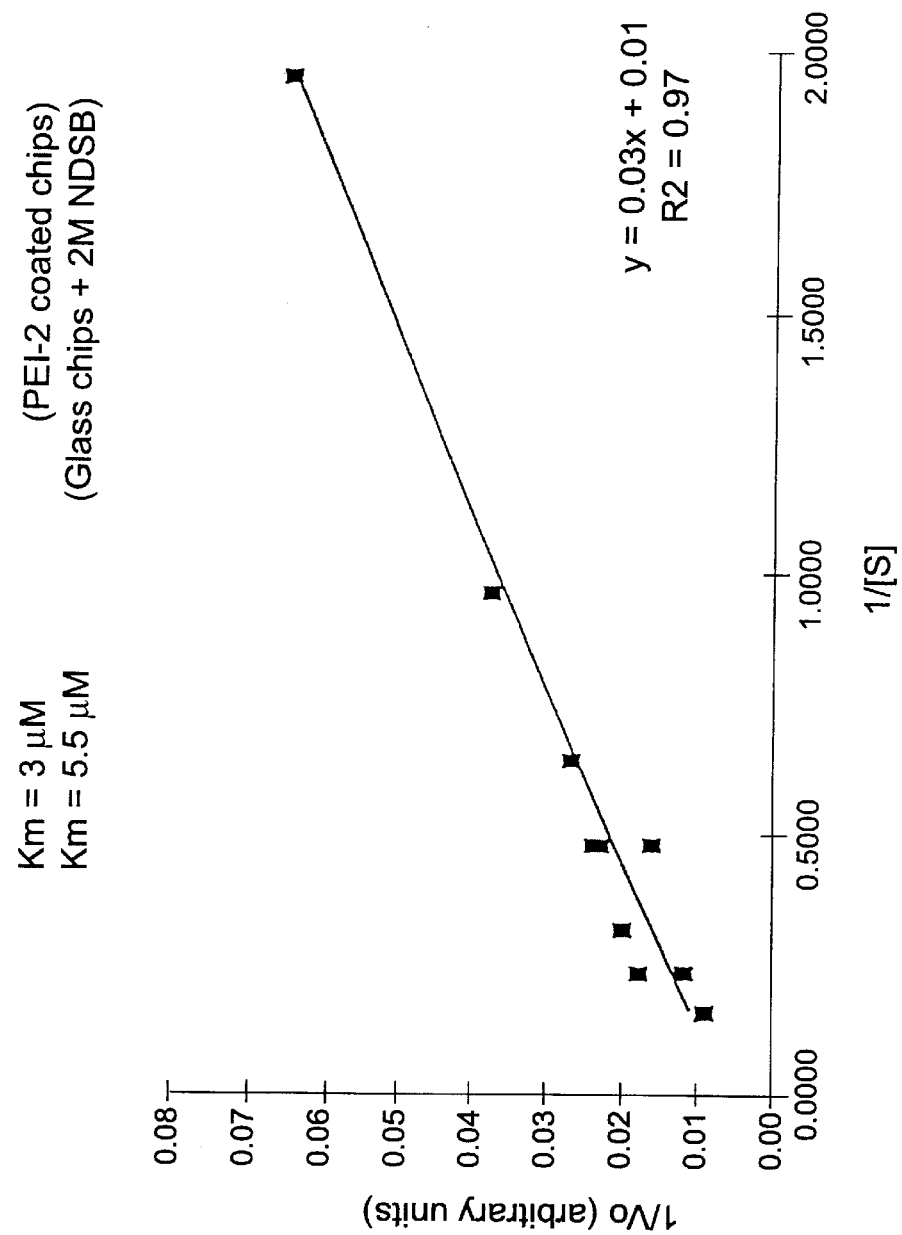
FIG. 11 is a Lineweaver-Burk plot for a PTP1b $K_m$ assay in a PEI-2 coated microfluidic device.

A Lineweaver-Burk plot, 1/(product signal per unit time) vs. 1/(substrate concentration), was used to calculate $K_m$. (FIG. 11). Product signal was determined from the difference between the diFMUP+diFMU (enzyme+substrate) signal and the diFMUP (substrate only) signal, under conditions where less than 10% of the substrate was hydrolyzed. The final substrate concentration was calculated from Equation 4.

$$\text{Final Substrate Concentration} = (SC2) \times (C2)/(TC) \quad (4)$$

where SC2 is the substrate concentration in well 2, C2 is the current from well 2 and TC is the total current which in the present Example had a value of 6.1 μA.

The value of $K_m$ (3 μM) measured from the PEI-2 coated device data with no NDSB present (buffer=50 mM HEPES+ 10 mM DTT) compares reasonably well with the $K_m$ (5.5 μM) measured in a standard glass device using 2 M NDSB (buffer=50 mM HEPES+10 mM DTT+2M NDSB).

Figure 12:
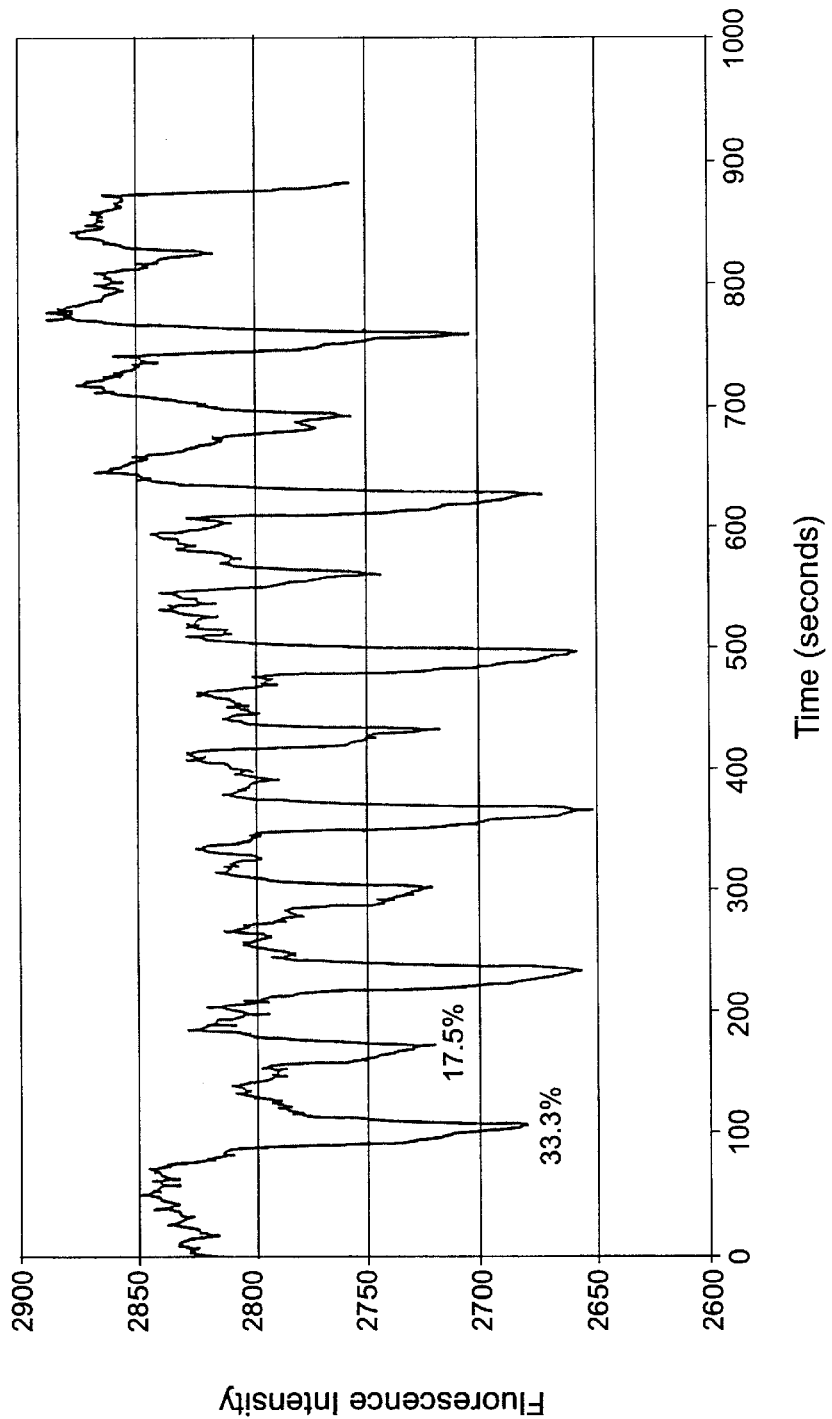
FIG. 12 is a plot of fluorescence intensity vs. time for a PTP1b inhibition assay in a PEI-2 coated microfluidic device.

Inhibition of enzyme activity was also demonstrated using a PEI-2 coated device (FIG. 12). The inhibitor has a net charge of −4 at the pH used for the PTP1b assay. No inhibition was observed in normal glass devices using this inhibitor, presumably because its electrophoretic mobility is large enough (and opposite in sign to the electroosmotic flow) that its net velocity is small or even reversed compared to that of bulk fluid flow. In the PEI-2-coated devices, electrophoresis of negatively-charged molecules and electroosmotic flow have the same direction. Inhibition of enzyme activity was detected upon toggling the flow of inhibitor on. PEI-2 coated glass surfaces exhibit much less protein adsorption than uncoated glass devices, as indicated by the ability to run a PTP1b enzyme inhibition assay without having to add the high concentrations of zwitterion required to prevent this enzyme from adsorbing to the walls of glass microchannels. The $K_m$ for the PTP1b/diFMUP reaction was measured and was in good agreement with that determined using a normal glass device with NDSB-containing assay buffer. Using a PEI-2 coated device, it was possible to detect inhibition of enzyme activity using a compound that would not flow in normal glass devices due to its −4 charge.

Example 3

Example 3 further illustrates the resistance to protein adsorption imparted to microfluidic devices by coating these devices with poly(ethyleneimine) moieties. The adsorption of BSA and avidin was assayed.

3.1 Materials and Methods 3.1a PEI-2 Coated Device

Figure 28:
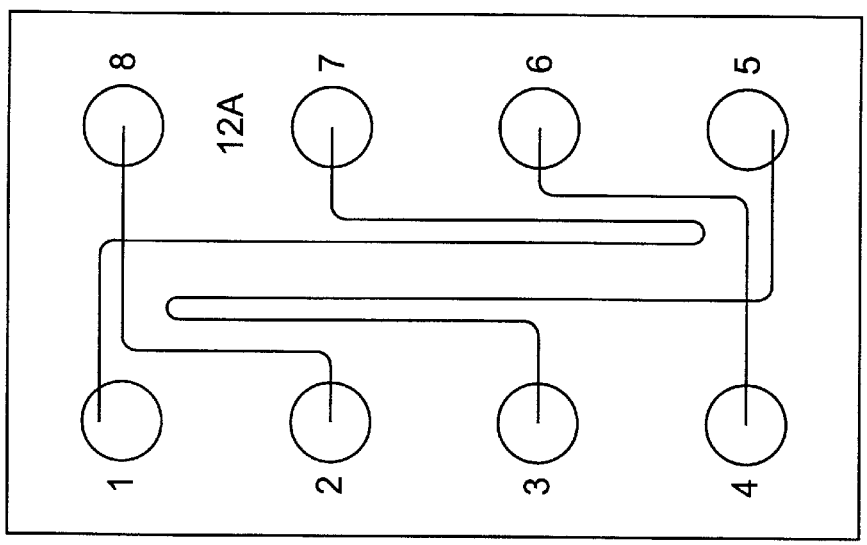
FIG. 28 is a cartoon showing the layout of the microfluidic devise used for the BSA and Avidin assays and various coating procedures.

The microfluidic devices used for enzyme assays measuring electroosmotic mobility (EO), had the channel format shown in FIG. 28 (15 micron channel depth). The top surfaces of new devices were treated with Repel-Silane-ES. The microchannels were cleaned prior to coating by successive rinses with 1N NaOH, water, 1N HCl, water and ethanol, and then dried overnight at 100–120° C. The devices were coated by filling the microchannels with the coating solution (8% PEI-2/water) and left overnight, followed by extensive rinsing with water. The devices were stored dry after coating. The devices were conditioned by running assay buffer through the device for 10 minutes before starting the assay, and were rinsed extensively with water after running the assay.

3.1b Reagents

The protein assays were run using an assay buffer consisting of 50 mM (Hepes, pH=7.5, conduct.=1.6 mS/cm). The labeled protein solutions employed were 0.02 mg/ml labeled protein, BSA-Bodipy-FL or Avidin-Bodipy-FL, in the Hepes buffer.

3.2 Assays

In the microfluidic device, well 2 was filled with labeled protein solution, wells 1, 7 and 8 were filled with Hepes buffer solution. Plugs of fluoresence labeled protien solution were injected from the cross section to well 7 and were detected downstream with the time/current profile shown in Script 4. The mobility of the protein was then calculated by Equation 2 (see section 1.1c). Protein adsorption was indicated by the change in peak shape, change of the apparent mobility and an increase in the fluorescence background signal.

| State | Script 4 Wells | | | | | | | | Time |
|---|---|---|---|---|---|---|---|---|---|
| # | 1 | 2 | 3 | 4 | 5 | 6 | 7 | 8 | (sec) |
| 0 | 0.3 | −5 | 1500 V | 0 V | −3 | 0 | −3 | | 50 |
| 0 | −5 | 0 | 1500 V | 0 V | −3 | 0 | −3 | | 15 |
| 0 | 0.3 | −5 | 1500 V | 0 V | −3 | 0 | −3 | | 50 |
| 0 | −2.5 | −2.5 | 1500 V | 0 V | −3 | 0 | −3 | | 15 |

3.3 Results

The data (FIGS. 16A–18C) from the protein adsorption assays show that PEI-2 coated microfluidic devices adsorb substantially less protein on channel surfaces than non-coated devices. When the protein was negatively charged, such as BSA, protein plugs were detected in both PEI-2 coated and non-coated devices. However, the change in peak shape and the change in apparent mobility were much lower for PEI-2 coated devices than for non-coated devices. Additionally, the background increase was much higher than for non-coated devices. PEI-2 coated surfaces adsorbed very little positively charged proteins (i.e. avidin).

Example 4

Figure 13:
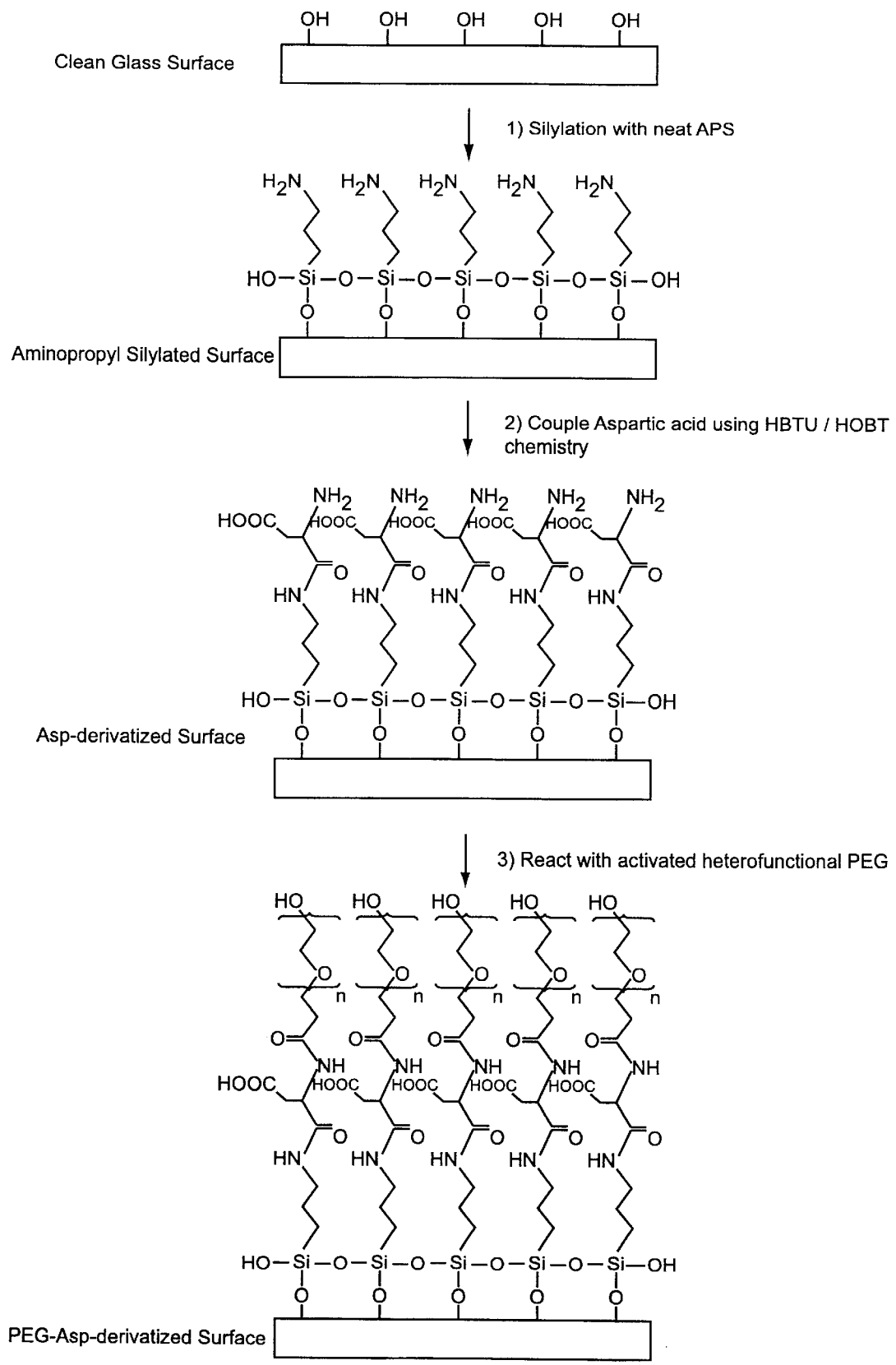
FIG. 13 is a synthetic scheme for assembling an amino acid-poly(ethyleneglycol) coating.
Figure 14A:
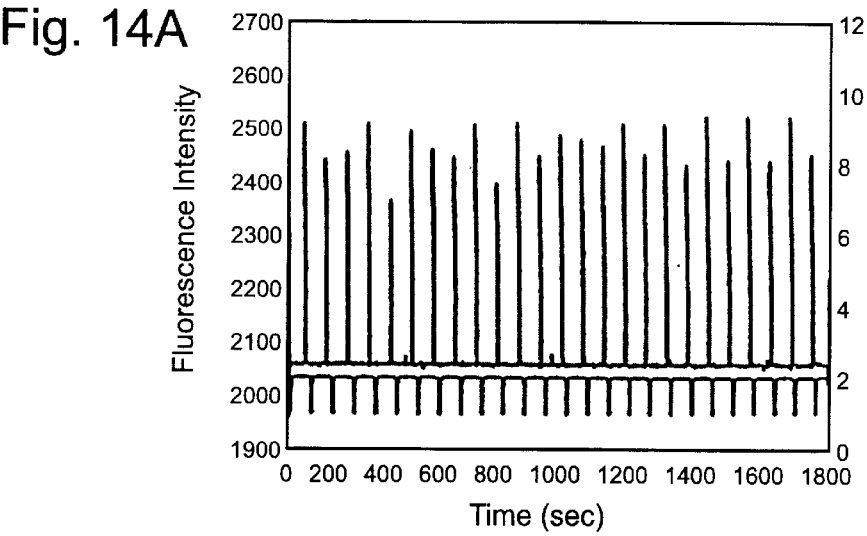
FIGS. 14A–F are plots of fluorescence intensity vs. time for a mobility stability test of a microfluidic devise coated by PEI-1 (polyethylenimine).
Figure 14B:
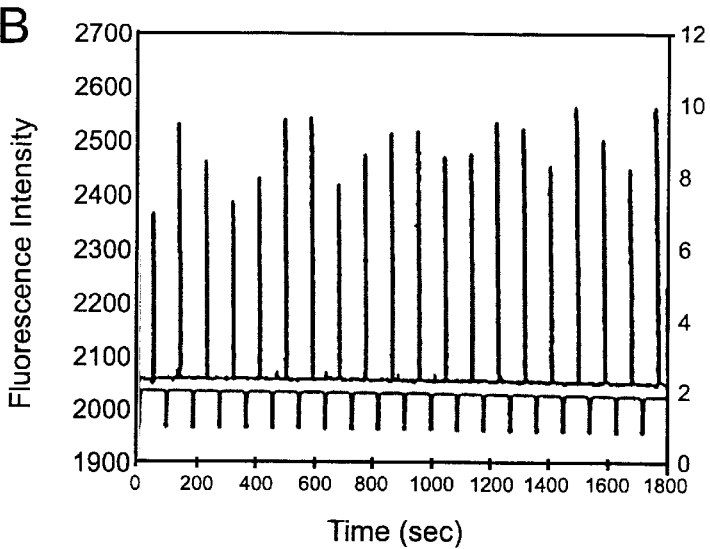
Figure 14C:
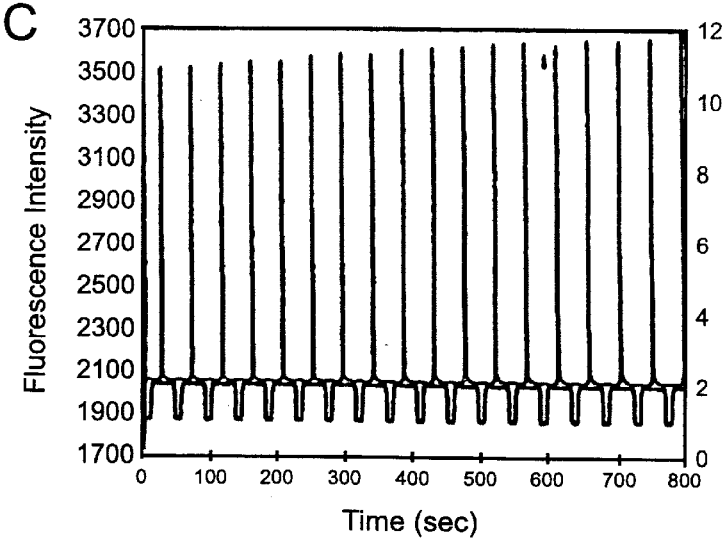
Figure 14D:
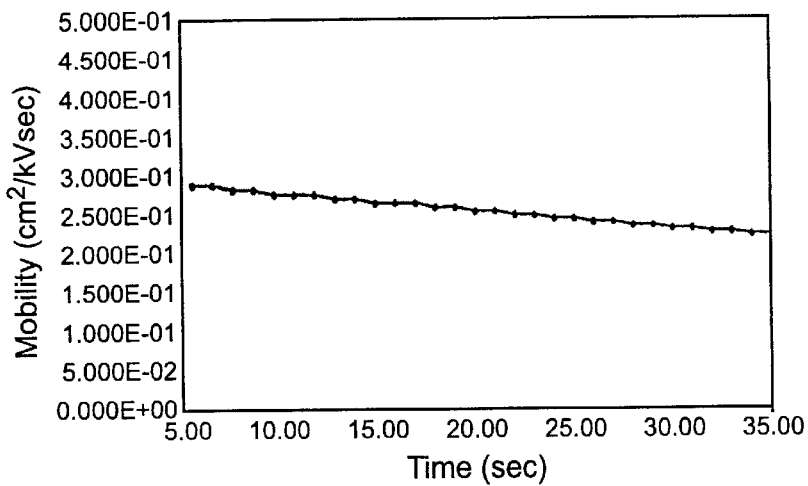
Figure 14E:
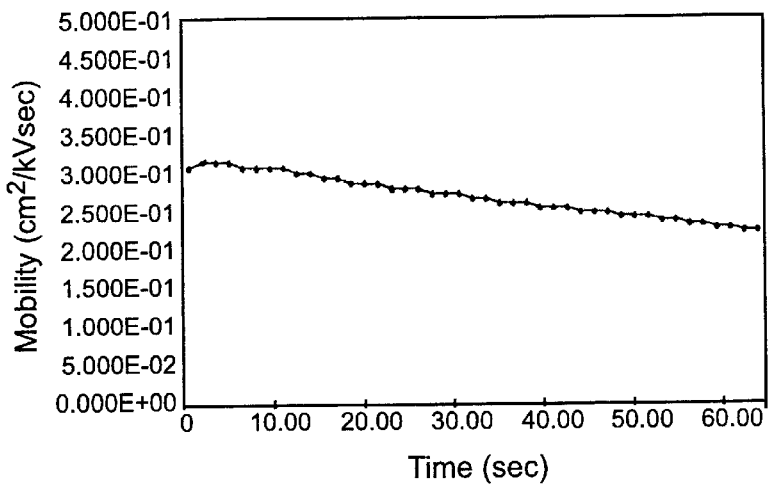
Figure 14F:
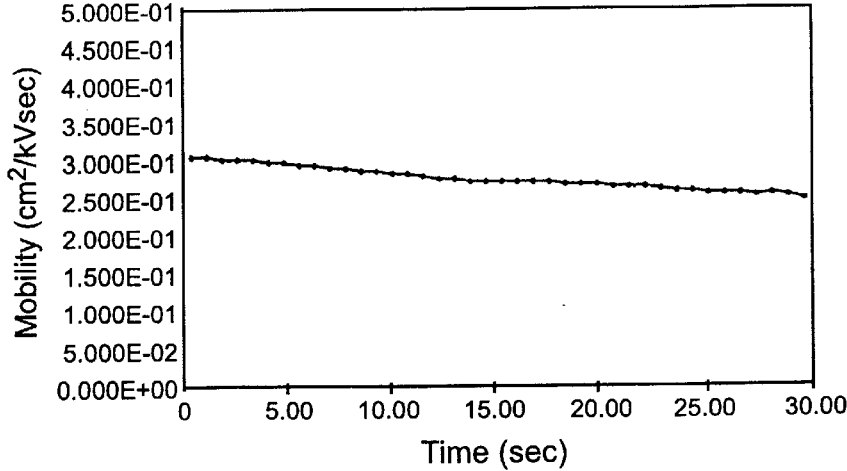
Figure 15A:
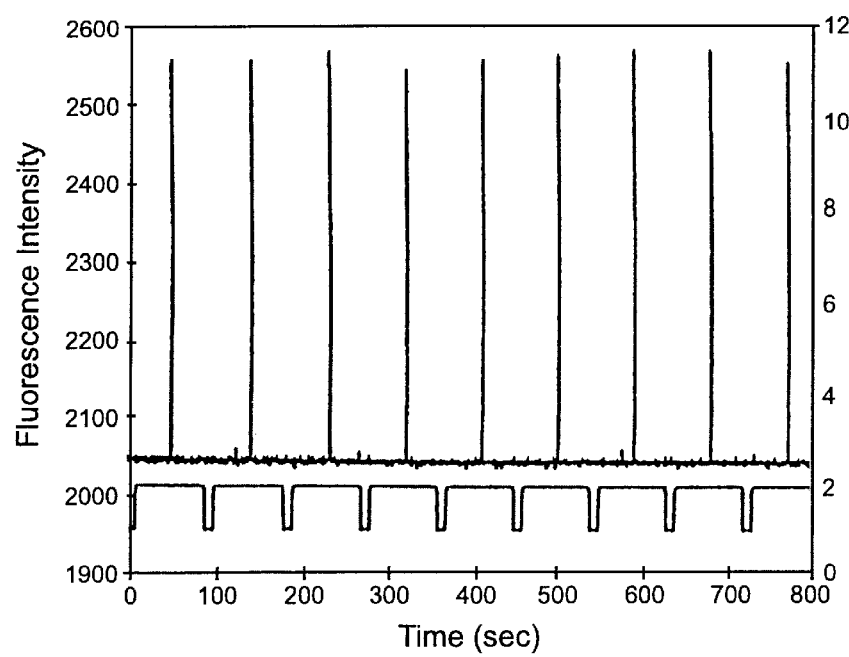
FIGS. 15A–D are plots of fluorescence intensity vs. time for a mobility stability test of a microfluidic devise coated by PEI-2 (80% ethoxylated polyethylenimine).
Figure 15B:
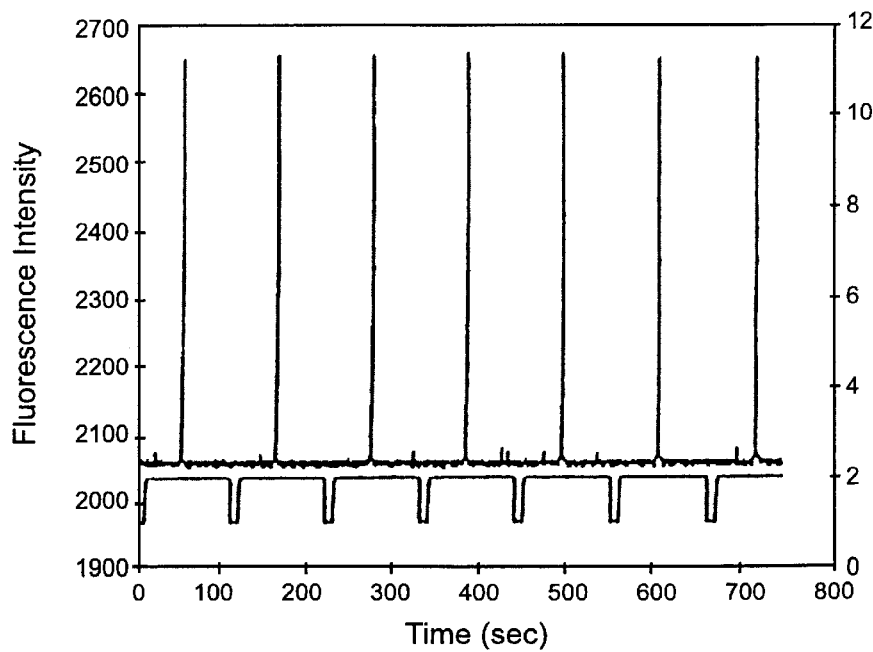
Figure 15C:
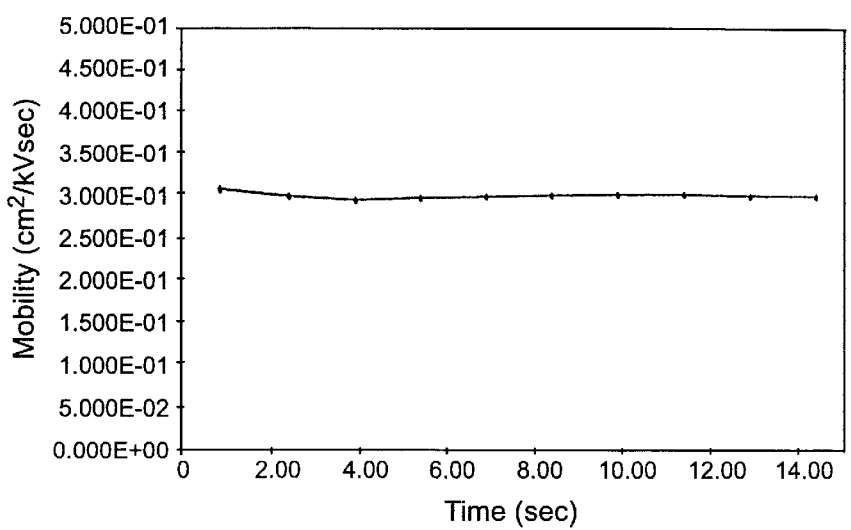
Figure 15D:
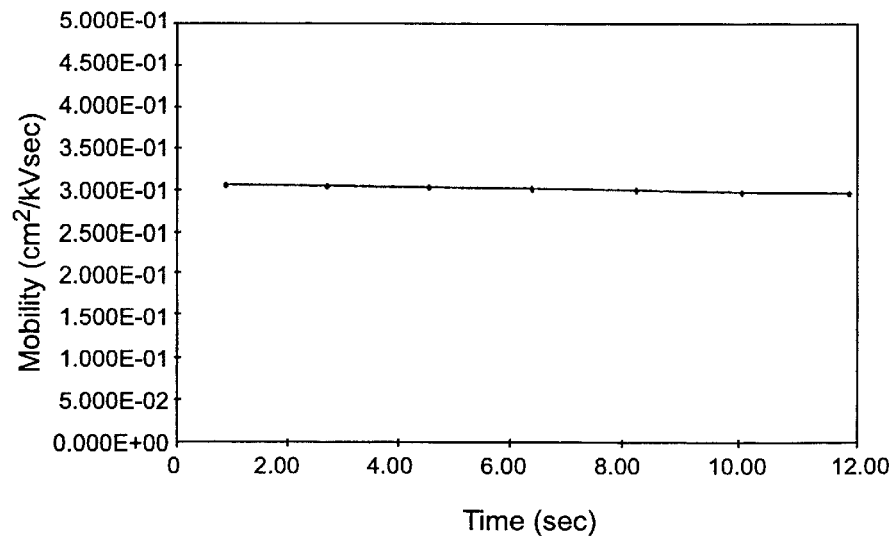
Figure 16A:
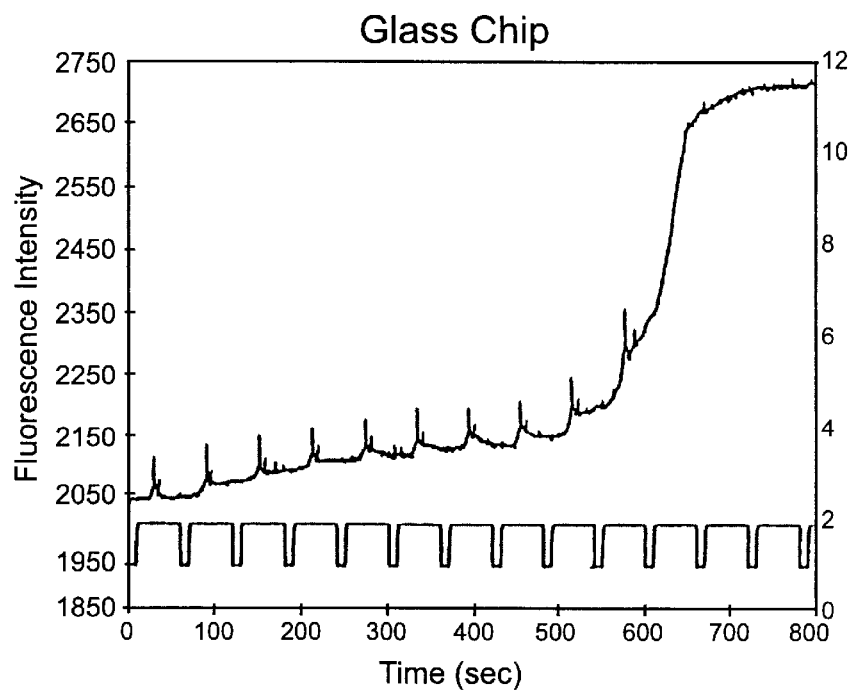
FIGS. 16A–C are a comparison of protein adsorption on a glass microfluidic device and PEI-2 coated microfluidic device via the BSA-Bodipy-FL injecting test (pH<7.5).
Figure 16B:
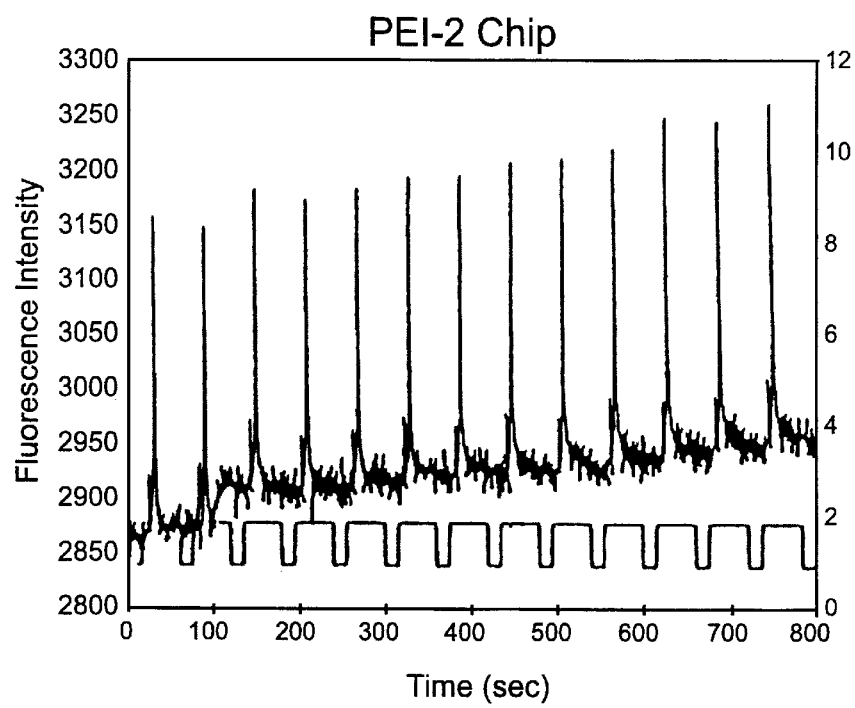
Figure 16C:
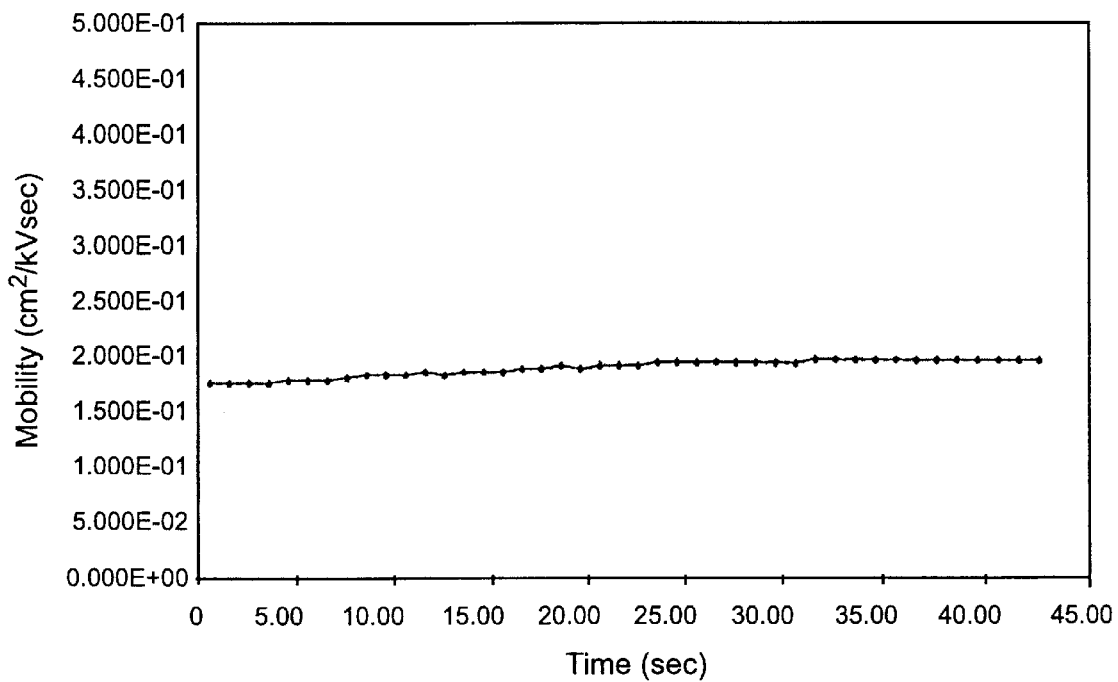
Figure 17C:
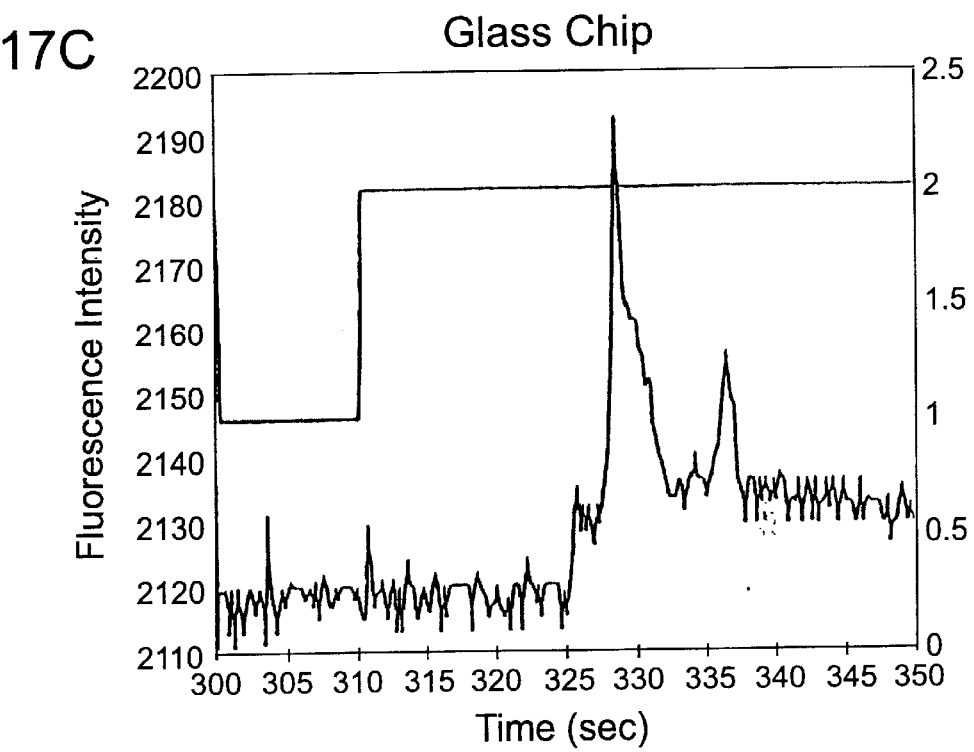
Figure 17D:
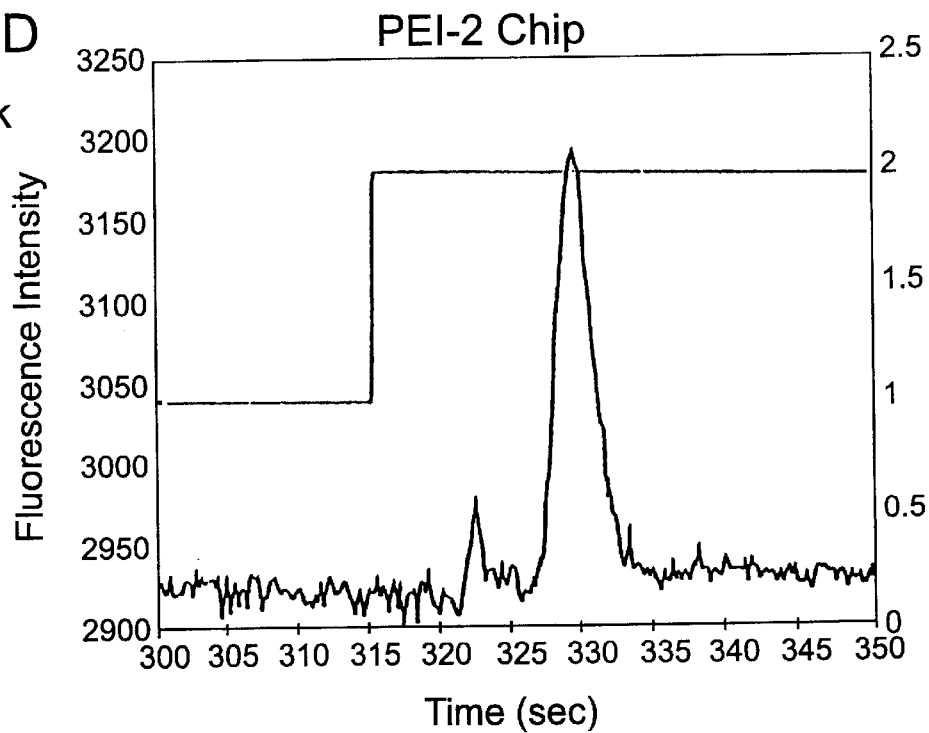
Figure 18B:
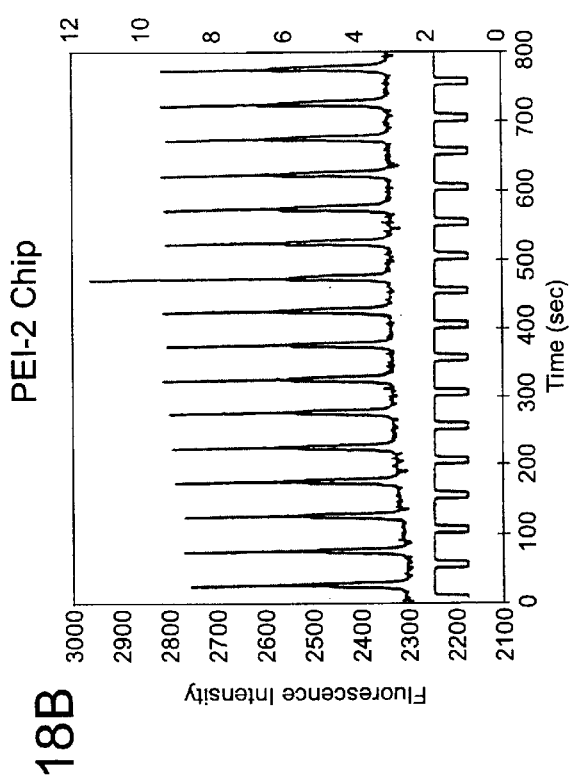
FIGS. 18A–C are a comparison of protein adsorption on a glass microfluidic device and PEI-2 coated microfluidic device via the Avidin injecting test (pH>7.5).
Figure 18C:
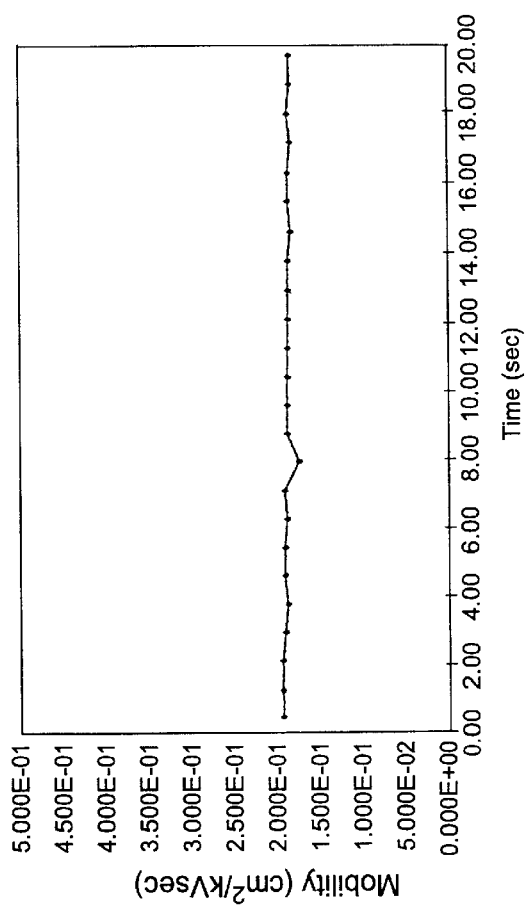
Figure 18A:
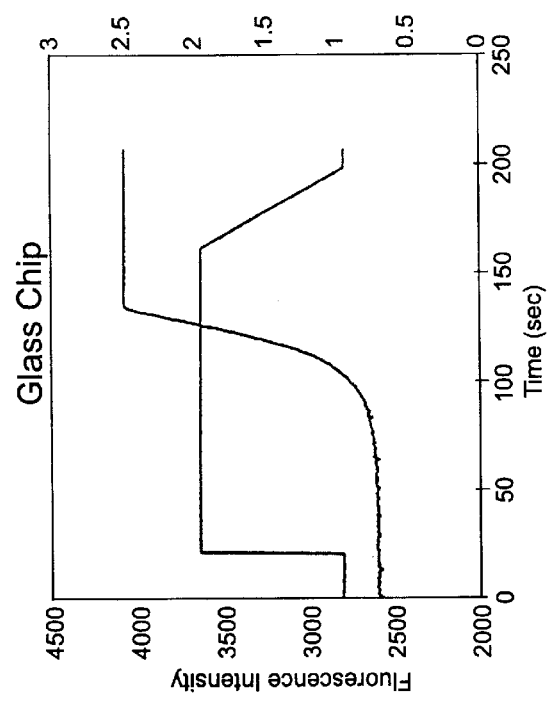
Figure 19:
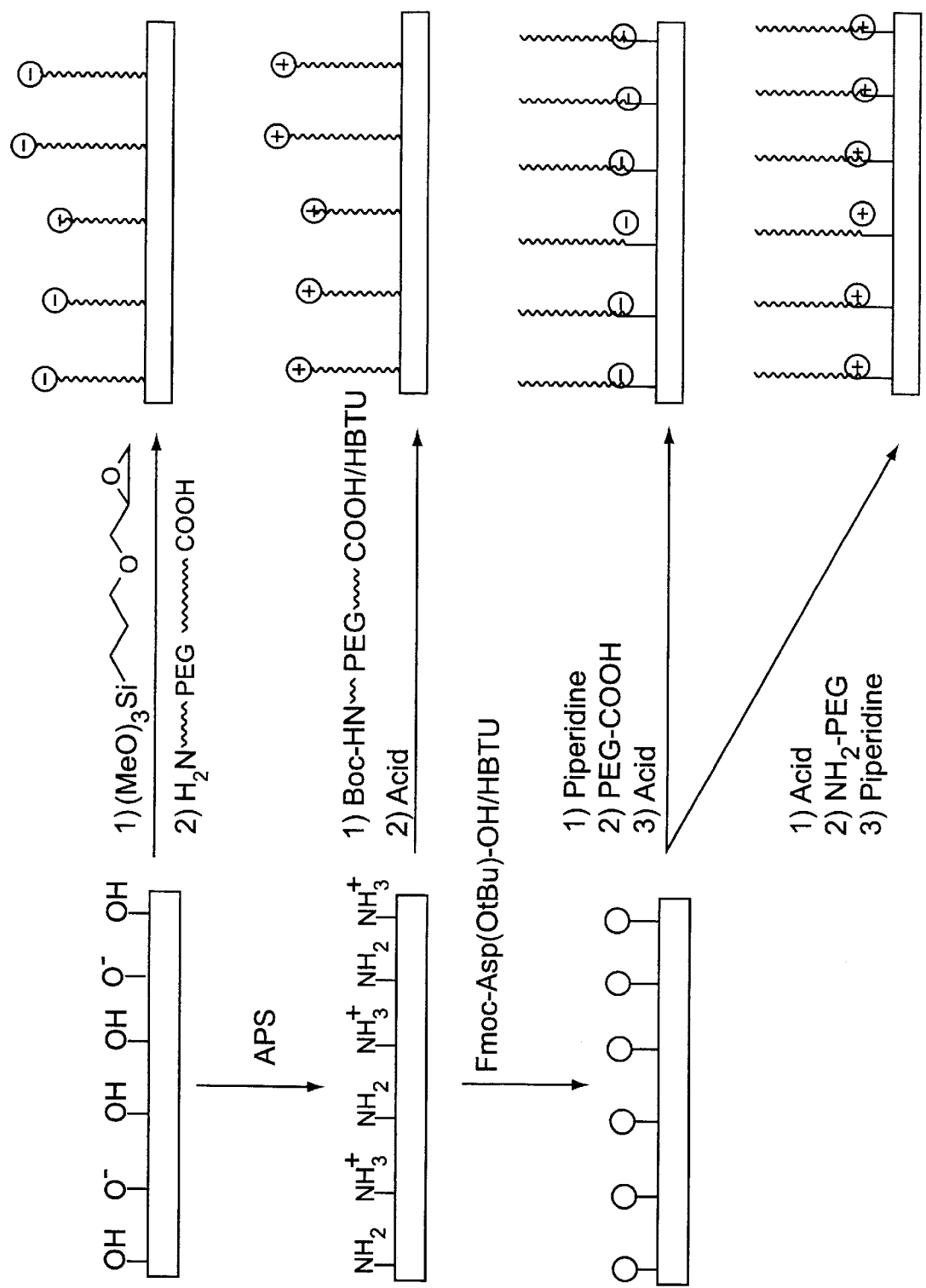
FIG. 19 is a reaction scheme for modifying the surface of a microfluidic device with a silylating agent, followed by reaction with a bifunctional poly(ethyleneglycol).

Example 4 details the preparation of amino acid conjugated poly(ethyleneglycol) surface coatings for microfluidic devices. PEG molecules were indirectly covalently grafted by reacting the surfaces of microfluidic devices with functionalized PEGs via silane or polymer linker. This preparation is also outlined in FIG. 13.

A multi-step reaction processes was used for preparing covalently attached PEG coatings on the glass surfaces (Herren, et al., *J. Colloid Interface Sci.* 115: 46 (1987); Bruin et al., *J. Chromatogr.* 471:429 (1989); Townes et al., *J. Chromatogr.* 599: 227 (1992); Nashabeh et al., *J. High Resol. Chromatogr.* 15: 289 (1992); Emoto et al., *ACS Symp. Ser.*, 680 (*Poly(ethylene glycol)* 374: 399 (1997); Mechref et al., *Electrophoresis* 16: 617–624 (1995); Emoto et al., *Langmuir*, 14: 2722–2729 (1998); Palm et al., *Anal. Chem.* 69: 4499–4507 (1997). In the first step, the silica surface of the microfluidic device was activated by the functional silane 3-aminopropyltriethoxysilane (APS). A positively-charged polymer such as PEI would also work. The activated surface is then reacted with the functional group on a derivatized PEG molecule.

4.1 Materials and Methods 4.1a Surface Activation

An activating solution was used for activating the microfluidic device surface (see, FIG. 28) for coupling with functionalized PEGs. The activating solution comprised a mixture of water, APS (Aldrich) and ethanol (2:2:100). The solution was mixed and filtered 2 hours prior to coating.

The microfluidic devices were cleaned and dried (see, Example 1.1), rinsed and filled with one of the two coating solution, and allowed to react for 20 minutes to 1 hour. The devices were then extensively rinsed with solvent and anhydrous ethanol (Aldrich), and cured at 120° C. in a vacuum oven overnight. The activated microfluidic devices were visually inspected by microscope and kept in a desiccator if they were not used immediately for the next step of the reaction.

4.1b PEG Coating by Covalent Reaction With APS-activated Surfaces

The activated surface of the microfluidic device was then coupled with Fmoc-Asp(OtBu)-OH (Novabiochem) and then with heterobifunctional PEG molecules which had either an amino group or a carboxyl group at one end. The differentiated PEG molecule were employed to produce coatings with either a positive or negative charge.

4.1b(i) Reaction With Fmoc-Asp(OtBu)-OH to Create a Positively Charged PEG-coating:

Fmoc-Asp(OtBu)-OH (Novabiochem) was coupled onto the microchannel walls of an APS-activated microfluidic device through an amide bond linkage. Following the APS reaction, the microchannels were filled with activated Fmoc-Asp(OtBu)-OH solution (a mixture of Fmoc-Asp(OtBu)-OH, (51 mg, 0.125 mmol), HBTU (Novabiochem, 52 mg, 137 mmol), HOBT (Novabiochem, 1.9 mg, 0.012 mmol), DIEA (Aldrich, 21 µl, 0.125 mmol) and DMF (0.5 ml)), and allowed to react for 2 hours, followed by extensive rinsing with DMF and ethanol.

Heterobifunctional PEG molecules with an amino group at one end (Shearwater Polymers) were then coupled onto the modified surface, again through an amide linkage. The t-butyl protecting group of the Asp residue side-chain was removed by treatment with 5N HCl for 2 hours. After deprotection, the microchannel was filled with activated $NH_2$-PEG solution (a mixture of $NH_2$-PEG (0.125 mmol), HBTU (Novabiochem, 52 mg, 0.137 mmol), HOBT (Novabiochem, 1.9 mg, 0.012 mmol), DIEA (Aldrich, 21 µl, 0.125 mmol) and DMF (0.5 ml)), and allowed to react for 2 hours. The reaction solution was then removed and the microchannel rinsed extensively with DMF.

Finally, the Fmoc protecting group was removed from the Asp residue amino group by treatment with 20% piperidine (Aldrich)/DMT for 2 hours, followed by extensive rinsing with DMT and ethanol.

4.1b(ii) Reaction With Fmoc-Asp(OtBu)-OH to Create a Negatively Charged PEG Coating:

Fmoc-Asp(OtBu)-OH (Novabiochem) was coupled onto the microchannel walls of APS-activated microfluidic devices as described above. Heterobifunctional PEG molecules with a carboxyl group at one end (Shearwater Polymers) were then coupled onto the modified surface. The Fmoc protecting group of the Asp residue amino group was removed by treatment with 20% piperidine(Aldrich)/DMF for 2 hours. After deprotection, the microchannel was filled with activated PEG-COOH solution (a mixture of PEG-COOH (0.125 mmol), HBTU (Novabiochem, 52 mg, 0.137 mmol), HOBT (Novabiochem, 1.9 mg, 0.012 mmol), DIEA (Aldrich, 21 µl, 0.125 mmol) and DMF (0.5 ml)), and allowed to react for 2 hours. The reaction solution was then removed and the microchannel rinsed extensively with DMF.

Finally, the t-butyl protecting group was removed from the Asp residue side chain by treatment with 5N HCl for 2 hours, followed by extensive rinsing with DMF and ethanol.

The extent to which reactions were successfully carried out was monitored qualitatively by making electroosmotic mobility measurements as described in Example 1.1 to observe the expected changes in sign and/or magnitude.

4.1c Electroosmotic Mobility Measurements

Electroosmotic mobility was measured using the neutral dye injection method. Rhodamine-B was placed in well 2 and then loaded to the main channel by flowing to well 8. A plug of Rhodamine-B was then injected by switching buffer flow from well 1 to well 7. The fluorescence signal can be detected anywhere down the channel and mobility then calculated from the measured transit time using the relationship displayed in Equation 2 (see, section 1.1c).

4.2 Results

Figure 20:
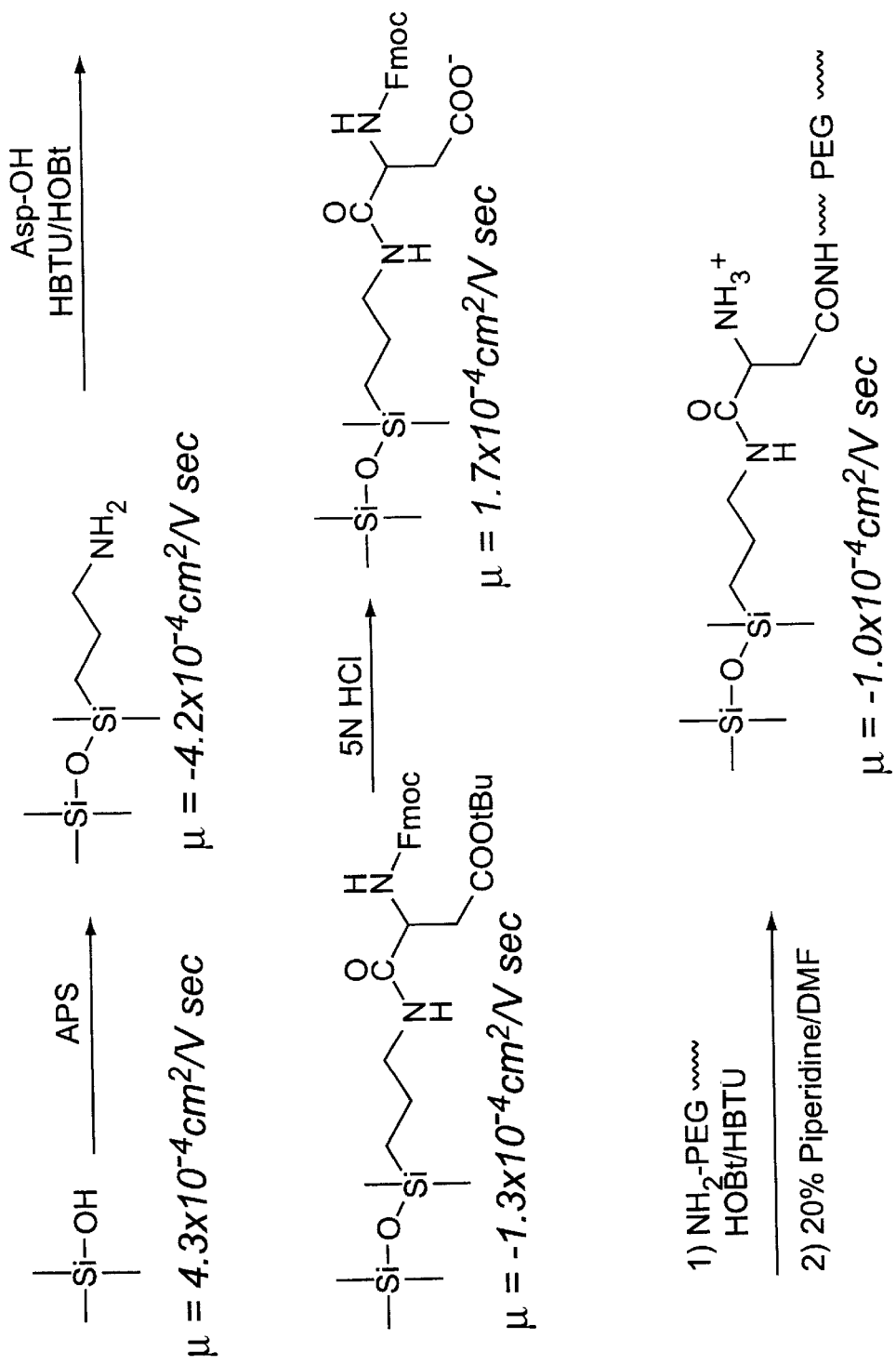
FIG. 20 is a reaction scheme for modifying the surface of a microfluidic device with a positively charged poly (ethyleneglycol) moiety.
Figure 21:
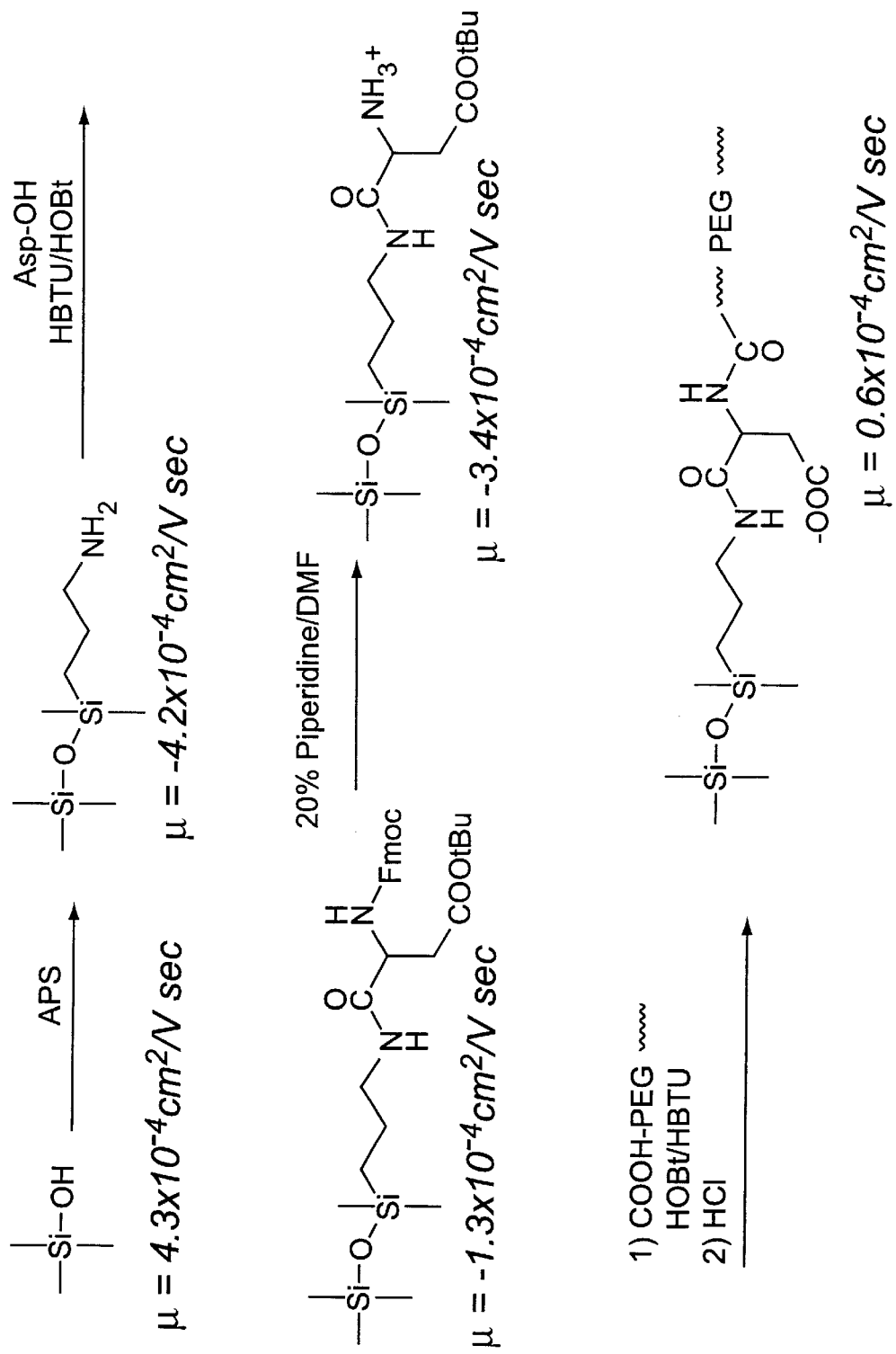
FIG. 21 is a reaction scheme for modifying the surface of a microfluidic device with a negatively charged poly (ethyleneglycol) moiety.

Coupling of heterobifunctional PEG molecules to APS-activated glass surfaces was used to generate a PEG coating with a charged group at one end of the PEG chain (FIGS. 20 and 21). The EOF mobility ($\mu_{eo}$) was observed to change following each reaction step. This change provided a qualitative indication that the chemistry was taking place successfully. Treatment with APS replaced the negative silanol groups of the glass surface with positive amino groups, and changed the sign of $\mu_{eo}$. Coupling Fmoc-Asp(OtBu)-OH to the surface reduced the number of available amino groups, and resulted in suppression of $\mu_{eo}$. Cleavage of the Fmoc protecting group by piperidine yielded a positively-charged amino group, increasing $\mu_{eo}$. Cleavage of t-butyl protecting groups by HCl yielded a negatively-charged carboxyl group, changing the sign of $\mu_{eo}$. After PEG coupling and deprotection, $\mu_{eo}$ changed sign and was reduced in magnitude. The overall-decrease in magnitude of the EOF mobility is most likely due to incomplete reaction at one or more steps of the derivatization process.

Example 5

An alternative to Example 4 for preparing an amino acid conjugated poly(ethyleneglycol) surface coating for microfluidic devices via indirect covalent bonding is illustrated in Example 5. PEG molecules were indirectly covalently grafted by reacting the surfaces of microfluidic devices with functionalized PEGs via a silane or polymer linker. A similar multistep reaction process to Example 4 was used but an alternative activation solution, 3-glycidoxypropyl trimethoxysilane, was employed rather than APS in this synthetic strategy for coating a microfluidic device.

5.1 Materials and Methods 5.1a Surface Activation

Figure 22:
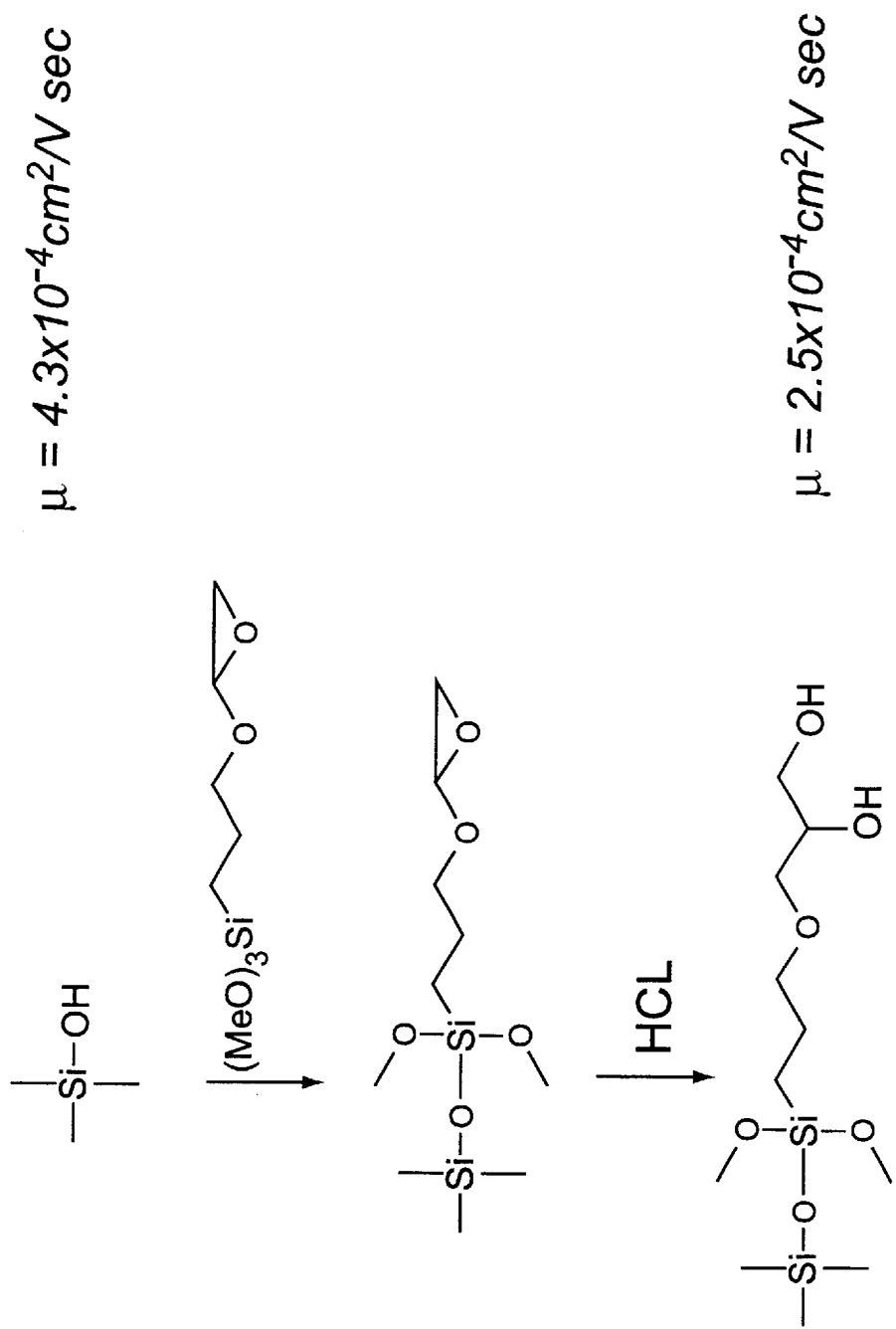
FIG. 22 is a reaction scheme for modifying the surface of a microfluidic device with a neutral hydrophilic moiety.

In this example an alternative activating solution was used for activating a microfluidic device (having the format shown in FIG. 28) surface for coupling with functionalized PEGs. The alternative activating solution 3-glycidoxypropyl trimethoxysilane consisted of an 8% w/v 3-glycidoxypropyltrimethoxysilane (Aldrich) in toluene. The solution was mixed and filtered 10 to 20 minutes before use in coating (FIG. 22).

The microfluidic devices were cleaned and dried (see, Example 1.1), rinsed and filled with one of the two coating solutions, and allowed to react for 20 minutes to 1 hour. The devices were then extensively rinsed with solvent and anhydrous ethanol (Aldrich), and cured at 120° C. in a vacuum oven overnight. The activated microfluidic devices were visually inspected by microscope and kept in a desiccator if they were not used immediately for the next step of the reaction.

5.1b "PEG Like" Coating by Covalent Reaction With 3-Glycidoxypropyltrimethoxysilane Activated Surfaces The activated surface of the microfluidic device was then coupled with Fmoc-Asp(OtBu)-OH (Novabiochem) and then with heterobifunctional PEG molecules which had either an amino group or a carboxyl group at one end. The differentiated PEG molecules were employed to produce coatings with either a positive or negative charge.

5.1b(i) Reaction With PEI and Ethylene Glycol Diglycidyl to Create a Positively-charged "PEG-like" Coating.

Figure 23:
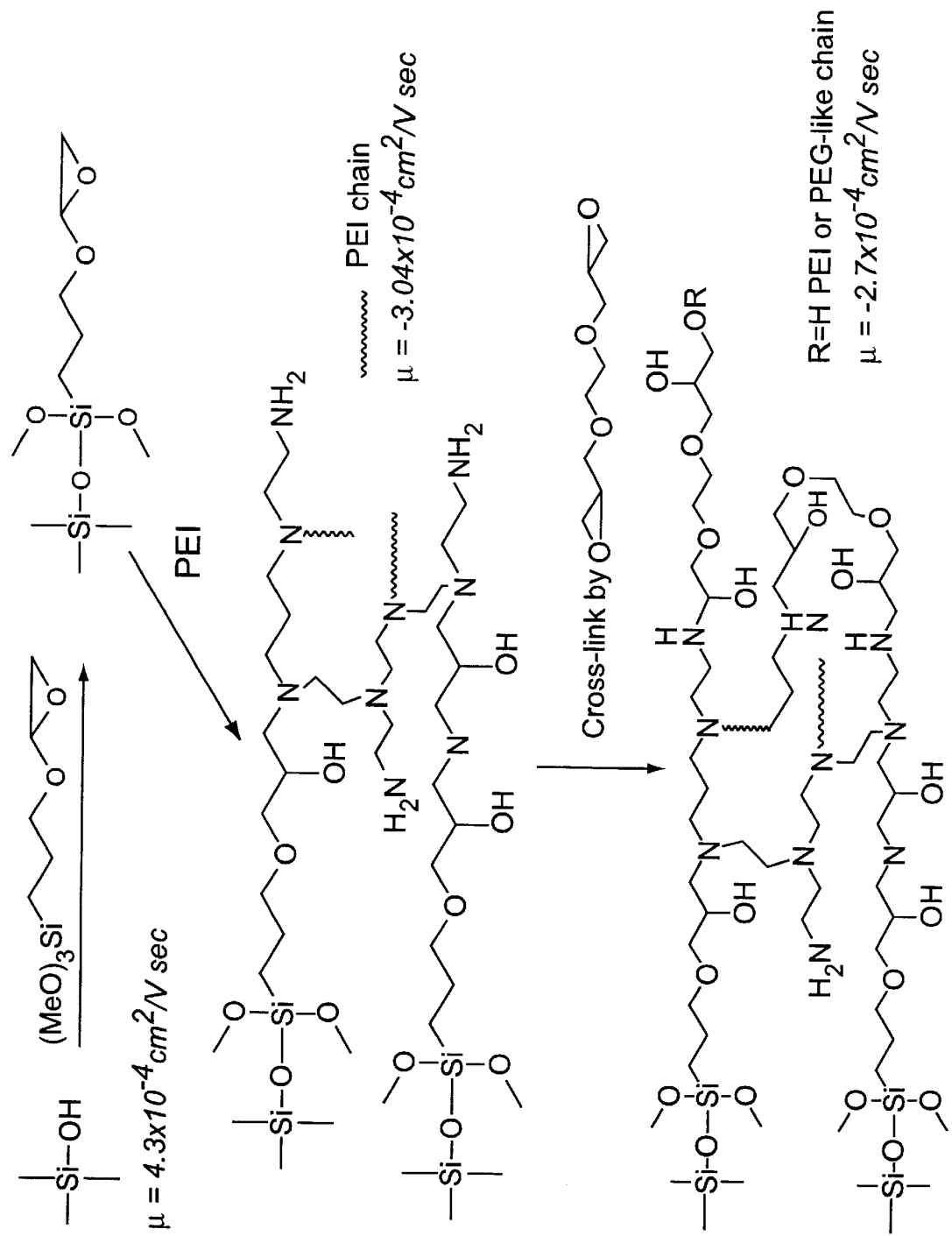
FIG. 23 is a reaction scheme for modifying the surface of a microfluidic device with a covalently cross-linked "poly (ethyleneglycol)-like" moiety.

After activation with 3-glycidoxypropyltrimethoxysilane, the microfluidic device was rinsed and filled with 8% PEI (polyethylenirnine, Mw=25,000, Aldrich)/ethanol, allowed react for 1.5 hours, rinsed with ethanol, and then cross-linked with 0.5M ethylene glycol diglycidyl (0.686 g, 4.0 mmol in 8 ml DMF) for 15 minutes. The device was then rinsed with DMF and ethanol, and dried at 100° C. for 2 hours (FIG. 23).

Figure 24:
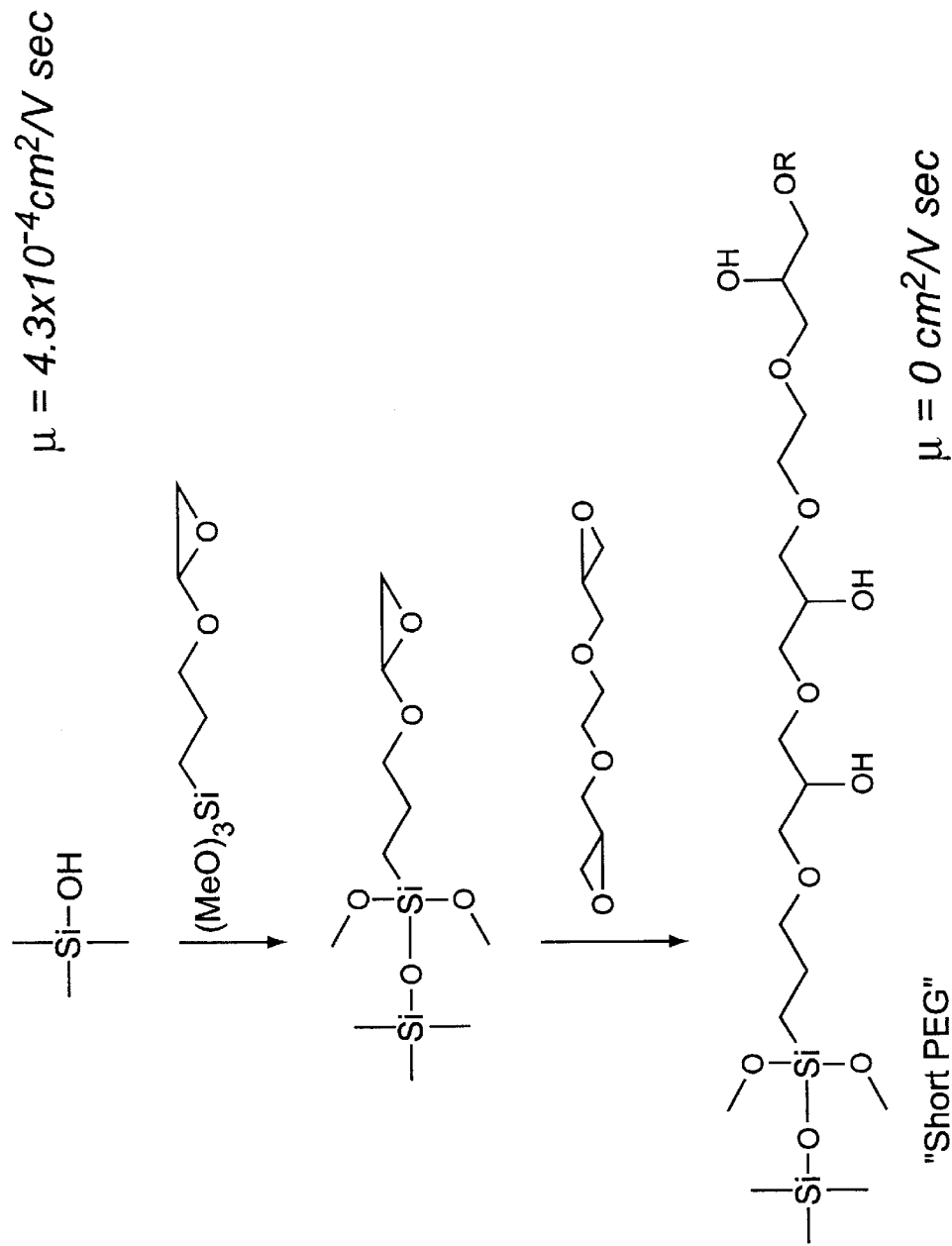
FIG. 24 is a reaction scheme for modifying the surface of a microfluidic device with a "short poly(ethyleneglycol)" moiety.

5.1b(ii) Reaction With Ethylene Glycol Diglycidyl to Create a Neutral "PEG-like" Coating After activation with 3-glycidoxypropyltrimethoxysilane, the microfluidic device was rinsed and filled with 0.5M ethylene glycol diglycidyl (0.686 g, 4.0 mmol in 8 ml DMF) and allowed to react for 1.5 hours. The device was then rinsed with DMF and ethanol, and dried at 100° C. for 2 hours (FIG. 24).

5.1b(iii) Reaction With Diglycolic Anhydride to Create a Negatively-charged "PEG-like" Coating.

Figure 25:
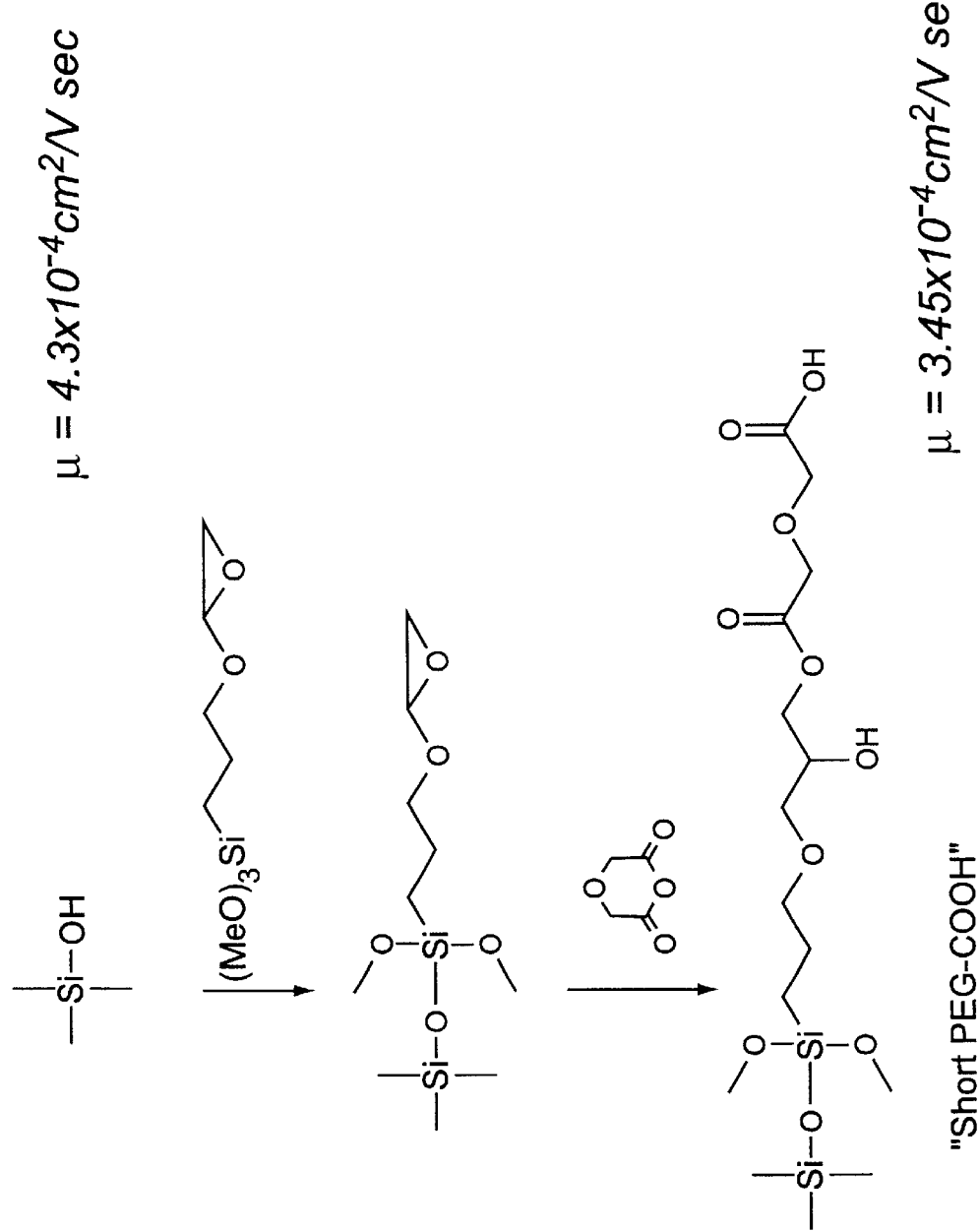
FIG. 25 is a reaction scheme for modifying the surface of a microfluidic device with a "short poly(ethyleneglycol)-COOH" moiety.

After activation with 3-glycidoxypropyltrimethoxysilane, microfluidic device was rinsed and filled with 0.5M diglycolic anhydride (Aldrich) in DMF, and then allowed to react for 1.5 hours. The device was then rinsed with DMF and ethanol, and dried at 100° C. for 2 hours (FIG. 25).

The extent to which reactions were successfully carried out was monitored qualitatively by making electroosmotic mobility measurements as described in Example 1.1 to observe the expected changes in sign and/or magnitude.

5.1c THP-1 Cell Flow Test

The THP-1 cell flow test comprises loading a cell/buffer in the well and letting the cell flow to the waste well. Observations are made on how the cells flow and how many cells stick onto the surface of the microfluidic device channels. From these observation the surface adsorption tendencies of PEG-coated and non-coated are compared.

5.2 Results

EOF mobility measurements showed that positive, negative and neutral "PEG-like" coatings were generated by reacting 3-glycidoxypropyltrimethoxysilane activated surfaces with PEI/ethylene glycol diglycidyl ($\mu_{eo}$=−0.27 cm$^2$/kV-s), diglycolic anhydride ($\mu_{eo}$=0.35 cm$^2$/kV-s), and ethylene glycol diglycidyl ($\mu_{eo}$ cm$^2$/kV-s). The THP-1 cell flow test showed that all three coatings, and especially the neutral one, demonstrated reduced cell adsorption to the walls of the microchannels.

Example 6

The stability of the PEG-coated microfluidic devices is shown in Example 6. Microfluidic devices of the format shown in FIG. 28 were used in these experiments.

Surfaces modified through silanation are usually stable up to pH 7.5. At higher pH, hydrolysis occurs and the surface coating may be damaged (Dougherty, A., et al., *J. Liquid. Chromatogr.* 14:907 (1997); Caravajal, S. G. et al., *Anal. Chem.* 60:1776 (1988); Burns, N. L. et al. *Langmuir* 11:2768 (1995); Nashabeh, W. et al., *J. Chromatogr.* 559:367 (1991).

The stability of the PEG coatings illustrated in Example 7 under basic conditions was studied (Table 2). The extent to which the PEG coating maintained its integrity was monitored qualitatively by making electroosmotic mobility measurements as described in Example 1.1 to observe the expected changes in sign and/or magnitude. The microfluidic devices were exposed to water and 1N NaOH. The EO mobility was compared before and after treatment with a base and the coated surfaces remained fairly stable. Surprisingly, the PEG coated surface tolerated hot Master Mix for more than 4 hours. When the devices were treated with 10N NaOH, however, the PEG coating was apparently removed completely because the electroosmotic mobility increased to the level observed for untreated glass devices. This property can be used for generating partially-coated chips.

TABLE 2

| Coating Condition | Curing condition | EO Mobility (fresh device) $cm^2/kV\text{-}s$ | Treatment | EO Mobility (after treat.) $cm^2/kV\text{-}s$ |
| --- | --- | --- | --- | --- |
| 5% in Toluene overnight | 120° C. overnight | 0.05 | 10 N NaOH 10–20 minutes | 0.34 0.43 |
| 10% in Toluene 4 hours | 100° C. overnight | 0.08 | DI-water 2 days | 0.16 |
| 10% in Toluene 4 hours | 100° C. overnight | 0.09 | DI-water 2 days and IN NaOH 0.5 hour | 0.21 |
| 10% in Toluene | 120° C. | 0.18 | Master Mix for PCR | 0.23 |
| Overnight | overnight | 0.19 | 4 hour, pH 8.3 T = 65–95° C. | 0.25 |

The aging of covalently modified (via a silane bond) PEG coated microfluidic devices was also studied by measuring the electroosmotic mobilities immediately after preparation and following storage at room temperature in air (Table 3). The coating was stable for more than 3 weeks.

TABLE 3

| Chip preparation conditions | EO Mobility (fresh device) $cm^2/kV\text{-}s$ | EO Mobility* (after 23 days) $cm^2/kV\text{-}s$ | EO Mobility (after 64 days) $cm^2/kV\text{-}s$ |
| --- | --- | --- | --- |
| 1.0% PEG-Silane/Toluene 3 hours, cured at 120° C. overnight | 0.14 | 0.17 | 0.17 |
| 5.0% PEG-Silane/Toluene 3 hours, cured at 120° C. overnight | 0.08 | 0.15 | 0.14 |
| 10% PEG-Silane/Toluene 3 hours, cured at 120° C. overnight | 0 | 0.03 | 0.06 |
| 1.0% PEG-Silane/Toluene overnight, cured at 120° C. overnight | 0.12 | 0.12 | 0.13 |
| 5.0% PEG-Silane/Toluene overnight, cured at 120° C. overnight | 0.12 | 0.13 | 0.13 |
| 10% PEG-Silane/Toluene overnight hours, cured at 120° C. overnight | 0.09 | 0.11 | 0.13 |

*Average of data for two microchannels

Example 7

Figure 26:
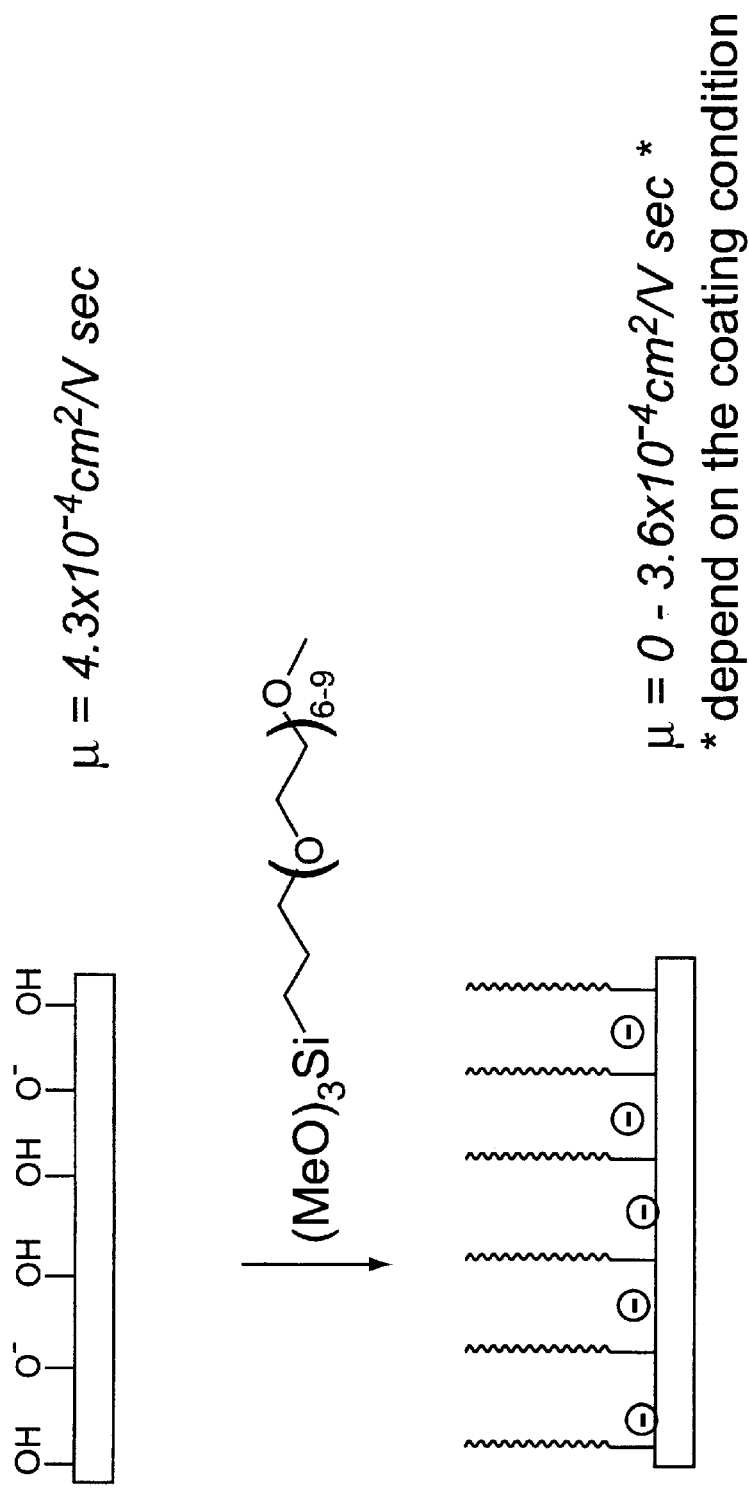
FIG. 26 is a reaction scheme for modifying the surface of a microfluidic device with a poly(ethyleneglycol)-silylating moiety.

Example 7 illustrates the preparation of a PEG coated microfluidic device via direct covalent modification through a silane bond (FIG. 26). Further, the resistance to protein adsorption imparted to microfluidic devices by coating these devices with poly(ethyleneimine) moieties is shown by measuring protein adsorption by a HSA-binding assay.

Direct covalent modification of glass surfaces through a silane bond is a simple one step reaction. The use of functional silanes for surface modification has been well-established in GC, HPLC and affinity chromatography applications. The silanol groups on silica surfaces are reacted with alkoxy or chlorosilanes, the reaction normally being carried out in dry solvent. The properties of the resulting modified surface depend on the functional group of the silane. Use of a PEG-silane allows PEG-coated surfaces to be created through this simple silylation reaction.

PEG-coated devices were prepared by several different procedures (see, Table 4), and characterized by electroosmotic mobility measurements, the THP-1 cell flow test (see, section 5.1c for procedure), and protein adsorption tests (see, HAS binding Assay information below).

7.1 Materials and Methods
  7.1a PEG Coated Devices

The microfluidic device used for coating and testing procedures had the channel format shown in FIG. 28. The coating solutions were prepared by dissolving 0.5–20% w/v of PEG-silane (2-(Methoxy(polyethyleneoxy)propyl) trimethoxysilane, $CH_3O\text{—}(CH_2CH_2O)_{6\text{-}9}\text{—}(CH_2)_3Si(OCH_3)_3$, from Gelest) in anhydrous toluene (Aldrich). Solutions were prepared from 10 minutes up to 22 hours prior to use for coating. The microfluidic devices were cleaned and dried (see, Example 1.1), the microchannels were filled with the coating solution and the devices were then immersed in the solution for the times specified in Table 4, followed by extensive rinsing with toluene and anhydrous ethanol (Aldrich), and curing at 120° C. in a vacuum oven for times ranging from 3 hours to overnight. The coated devices were visually inspected using a microscope, characterized by mobility measurements as detailed in Example 1.1.

7.2 HSA Binding Assay

The protein adsorption tests chosen for the PEG-coated microfluidic devices consisted of the signal baseline shift as a function of time in a HSA-binding assay. A dye molecule was used to bind HSA, which then became fluorescent. Change in signal baseline are an indication of HSA adsorption to the wall of the microchannel. Concentration of HSA (Mw=66,5000) and the dye are 5 $\mu$M and 20 $\mu$M respectively, in PBS buffer (pH 7.4). The background signal (B) is the measure with PBS buffer in the channel. $F_0$ and $F_f$ are the initial and final signals of the HSA-dye complex after it has flowed for a specified time in the channel.

% increase=$((F_f\text{-}B)\text{-}(F_0\text{-}B))/(F_0\text{-}B) \times 100\%$

The stability of the coating was studied by carrying out electroosmotic mobility measurements before and after prolonged exposure to DI-water, 1N NaOH, 10N NaOH, Master Mix, which is a mixture for TaqMan PCR containing all the kit components except the Control DNA, pH=8.3, temperature=65 to 95° C. (Protocol for TaqMan PCR Reagent Kit, Applied Biosystems) and afterwards, storage in air for up to 2 month. The extent to which reactions were successfully carried out was monitored qualitatively by making electroosmotic mobility measurements as described in section 1.1 to observe the expected changes in sign and/or magnitude.

7.3 Results

Use of toluene rather than ethanol as solvent gave more consistent results in mobility measurements and cleaner surfaces by visual inspection. It was also found that different batches of coated chips all exhibited reduced cell sticking, even though their electroosmotic mobilities were different. The results of these experiments are displayed in Table 4.

TABLE 4

| Coating solution | Coating time | Curing time | EO Mobility cm$^2$/kV-s | Cell sticking? |
|---|---|---|---|---|
| 1.3% in EtOH | 2 hours | 120° C. overnight | 0.23 0.058 | No |
| 5% in Toluene | Overnight | 120° C. overnight | 0.026 0.26 0.25 0.25 | No |
| 8% in Toluene | 6.5 hours | 100° C. overnight | 0.116 0.171 0.121 | No |
| 10% in Toluene | 4 hours | 100° C. overnight | 0.083 0.093 | No |
| 1.0% in Toluene | 2.5 hours | 100° C. overnight | 0.16 0.19 | No |
| 5.0% in Toluene | 2.5 hours | 100° C. overnight | 0.10 0.10 | No |
| 10% in Toluene | 2.5 hours | 100° C. overnight | 0.37 0.36 | No |
| 20% in Toluene | 2.5 hours | 100° C. overnight | 0.12 0.12 | No |
| 1.0% in Toluene | 3 hours | 120° C. overnight | 0.18 0.10 | No |
| 5.0% in Toluene | 3 hours | 120° C. overnight | 0.15 0 | No |
| 10% in Toluene | 3 hours | 120° C. overnight | 0 0 | No |
| 1.0% in Toluene | overnight | 120° C. overnight | 0.10 0.13 | No |
| 5.0% in Toluene | overnight | 120° C. overnight | 0.10 0.10 | No |
| 10% in Toluene | overnight | 120° C. overnight | 0.10 0.08 | No |

The PEG coated chips were found to vary somewhat from batch to batch. However, all of the PEG-coated microfluidic devices were better than glass devices in term of reducing the nonspecific adsorption of proteins and cells, and enhancing the wetting of the surface (Table 5).

TABLE 5

|  | % increase in 1 hour | % increase in 2 hour |
|---|---|---|
| Glass chip | 27.5 + 3.5 (N = 2) | — |
| PEG-coated chip | 9.5 + 4.1 (N = 3) | 17 |

Example 8

Figure 27:
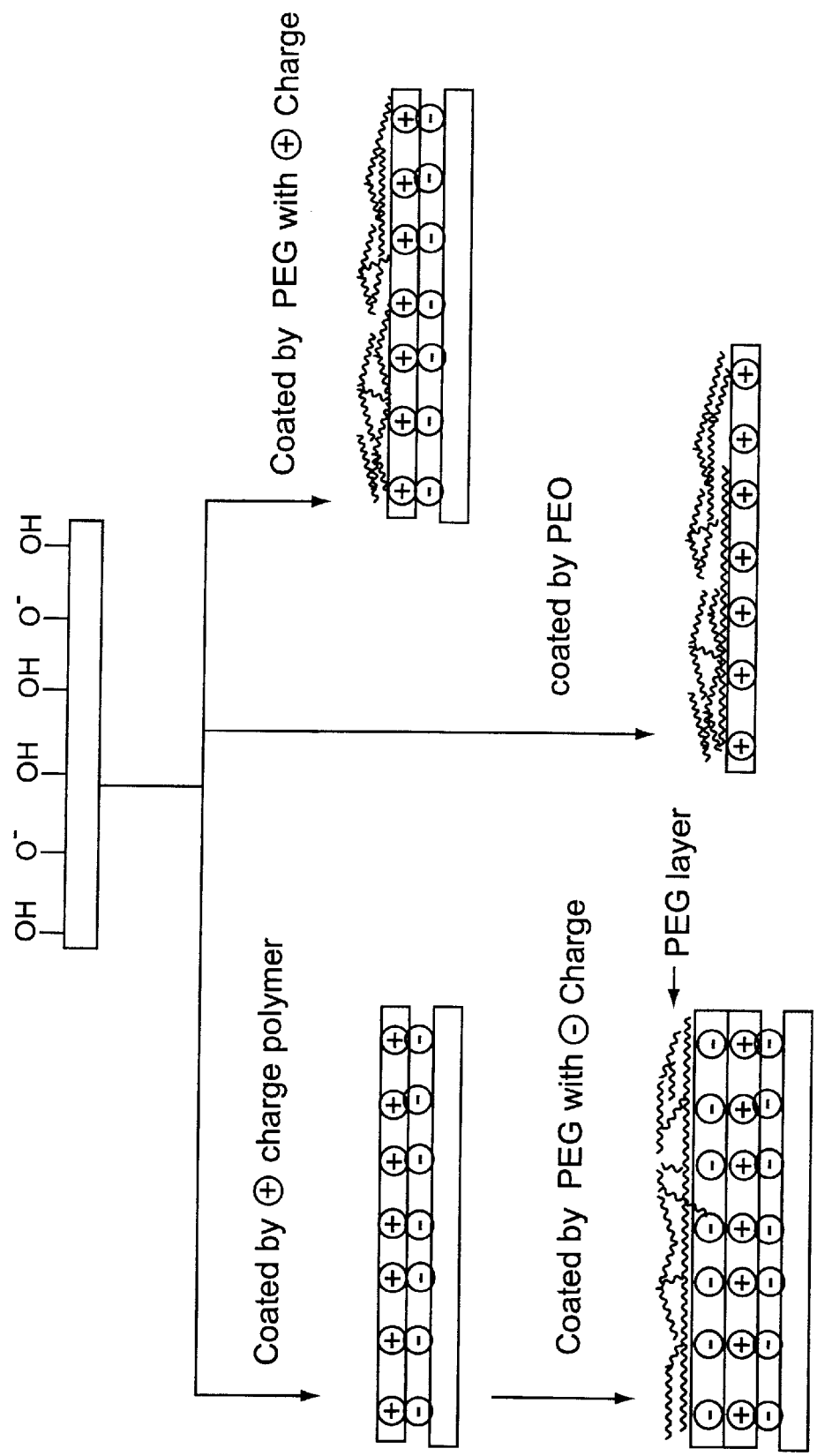
FIG. 27 is a reaction scheme for modifying the surface of a microfluidic device by a van der Waals adsorption methodology.

The preparation of PEG coated microfluidic devices by adsorptive coating methods taking advantage of Van der Waals force, hydrogen bonding and electrostatic interaction are demonstrate in Example 8 (FIG. 27). Two techniques, the simple adsorptive modification method and the successive multiple ionic-polymers (SMIL) coating method, were used to illustrated PEG coating of microfluidic devices.

The simple adsorptive modification methods is based on non-covalent interactions between PEO and the silica surface. Hydrogen bonding and hydrophobic interactions have been successfully utilized for coating the silanol surface with PEG in CE applications (Iki N. and Yeung E. S., *J. Chromatogr. A* 731: 273–282 (1996); Gordon et al., *Anal. Chem.* 63: 69 (1991). According to E. S. Yeung, basic proteins can be separated in PEO coated capillaries at pH 3–7 with much better peak shapes than in bare fused-silica capillaries, and higher separation efficiencies that are comparable to more sophisticated column treatment methods.

The SMIL coating procedure used poly(ethylene imine) (PEI) and HOOC-PEG-COOH. The idea was adopted from Katayarna et al., *Anal. Chem.* 70: 2254–2260 (1998), which reports a negatively charged dextran sulfate (DS) immobilized to the inner surface of glass capillaries by sandwiching cationic polymer Polybrene(PB) between the capillary wall and the DS without covalent bonding. The capillary coated by the SMIL procedure was tolerant to organic solvent, 1 M NaOH and a surfactant.

8.1 Materials and Methods

The microfluidic device used for coating and testing procedures had the channel format shown in FIG. 28 (with 15 μm deep channels). The top surfaces of the devices were treated with Repel-Silane-ES. The microchannels were cleaned prior to coating by successive rinses with 1N NaOH, water, in HCl, water, and ethanol, and then dried overnight at 100–120° C.

8.1a Simple Adsorptive Modification Method

The PEO (high molecular weight PEG which is also called poly(ethylene oxide)) coating solution was prepared by adding polymer powder (PEO, from Polyscience) to hot water while stirring vigorously. After complete dissolution and cooling, concentrated HCl and DI-water were added and adjusted to final concentration. The microchannels of clean, dried devices were treated with HCl for one hour, filled with the coating solution overnight, and then rinsed with DI-water.

8.1b Successive Multiple Ionic-polymer Layers (SMIL) Coating Method

This approach used a cationic polyethylene imine (PEI) layer followed by the PEG layer. The cationic PEI polymer solution was 8% polyethylene imine (PEI, Mw=25,000, from Aldrich) in 1:1 water/EtOH. The PEG solution was 20% w/v polyethylene glycol bis(carboxymethyl) ether (HOOC-PEG-COOH, Mw=250, from Aldrich). The microfluidic devices were first coated with PEI by filling the microchannel with the PEI solution and allowing the polymer to adsorb for 2 hours. This followed by vacuum removal of unadsorbed material and rinsing with DI-water. The devices were then coated with PEG by filling the microchannel with the PEG solution and allowing the polymer to adsorb for 1 hour, again followed by vacuum removal of unadsorbed material and rinsing with DI-water.

8.2 Results

In comparison to covalent modification, adsorptive coating methods are less difficult for preparing coated microfluidic devices. Both coating procedures described above were performed at room temperature, and required only the specified solutions and a vacuum pump to carry out. In order to adsorb the coating material, the solution must be introduced and passed through the microchannels of the microfluidic device. Normally, high molecular weight polymers are employed as coating materials because these are strongly adsorbed onto the silica surface by means of electrostatic, hydrogen bonding, or Van der Waals forces through multi-site interactions. However, the higher the molecular weight, the more viscous the solution.

8.2a Simple Adsorptive Modification Method Results

In microfluidic devices coated with PEO, it was observed that the electroosmotic mobility was suppressed by the PEO coating so that neutral dyes could not be electrokinetically pumped out of the reagent well. The mobility of the neutral dye in an uncoated glass device was 0.43 cm$^2$/KVS, while in a PEO coated device, the mobility was not measurable. This result indicates that the silanol groups were well covered by PEO.

8.2b Successive Multiple Ionic-polymer Layers (SMIL) Coating Results

Microfluidic devices coated with the cationic polymer PEI produced anodal electroosmotic flow ($\mu_{eo}$=0.30 cm$^2$/kVs compared to that of $\mu_{eo}$=0.43 cm$^2$/kVs for glass surfaces). Treatment of the PEI-coated devices with HOOC-PEG-COOH resulted in a novel double layer surface having near zero EOF ($\mu_{eo}$=0.11 cm$^2$/kVs), and showed much lower adsorption of THP-1 cells compared to bare glass chips.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A microfluidic device comprising:
   a body comprising a first region and a second region,
   a network of microchannels extending through the first and second regions of the body, the network of microchannels having a surface,
   a first coating covering the portion of the surface in the first region, forming a first coated surface,
   a second coating covering the portion of the surface in the second region, forming a second coated surface, and
   wherein the properties of the first and second coated surfaces are different.

2. The microfluidic device of claim 1, wherein the different properties comprise charge density.

3. The microfluidic device of claim 1, wherein the different properties comprise thickness.

4. The microfluidic device of claim 1, wherein the first and second coatings comprise hydrophilic polymers.

5. The microfluidic device of claim 4, wherein the hydrophilic polymers are selected from the group consisting of oligomeric ethers, oligomeric alcohols, polymeric ethers, and polymeric alcohols.

6. The microfluidic device of claim 1, wherein the formula for the first and second coated surfaces is:

$$R^1\text{---}\{(R^2)_a\text{---}(R^3)_m\}_n$$

wherein,
   $R^1$ is a member selected from organic polymers, glass or silica-based polymers;
   $R^2$ is selected from amino acids or peptides;
   $R^3$ is a hydrophilic polymer;
   $\alpha$ is greater than 0;
   m is at least 1; and
   n is $\geq 1$.

7. The microfluidic device of claim 6, wherein $R^3$ is different in the first and second coated surfaces.

8. The microfluidic device of claim 7, wherein the chain length of the polymer $R^3$ is different in the first and second coated surfaces.

9. The microfluidic device of claim 1, wherein the formula for the first and second coated surfaces is:

$$R^1\text{---}R^4\text{---}\{(R^2)_a\text{---}(R^3)_m\}_n$$

wherein,
   $R^1$ is a member selected from organic polymers, glass or silica-based polymers;
   $R^2$ is selected from amino acids or peptides;
   $R^3$ is a hydrophilic polymer;
   $R^4$ is a group having the formula:

$$X\text{---}R^5\text{---}Y$$

wherein,
   $R^5$ is ---(CH$_2$)$^s$---
   X and Y are the same or different and are inert linking groups, and s is at least 3;
   $\alpha$ is greater than 0;
   m is at least 1; and
   n is $\geq 1$.

* * * * *